United States Patent
Denney, Jr. et al.

(10) Patent No.: US 10,893,809 B2
(45) Date of Patent: Jan. 19, 2021

(54) METHOD AND SYSTEM FOR EVALUATING BLOOD VESSEL

(71) Applicants: Auburn University, Auburn, AL (US); The UAB Research Foundation, Birmingham, AL (US)

(72) Inventors: Thomas S. Denney, Jr., Auburn, AL (US); Himanshu Gupta, Birmingham, AL (US); Ankur Gupta, Boston, MA (US)

(73) Assignees: Auburn University, Auburn, AL (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/808,891

(22) Filed: Nov. 10, 2017

(65) Prior Publication Data

US 2018/0125376 A1 May 10, 2018

Related U.S. Application Data

(60) Provisional application No. 62/420,366, filed on Nov. 10, 2016.

(51) Int. Cl.
  *A61B 5/02* (2006.01)
  *A61B 5/021* (2006.01)
  (Continued)

(52) U.S. Cl.
  CPC .......... *A61B 5/02007* (2013.01); *A61B 5/022* (2013.01); *A61B 5/0215* (2013.01);
  (Continued)

(58) Field of Classification Search
  None
  See application file for complete search history.

(56) References Cited

U.S. PATENT DOCUMENTS

| 5,715,826 A | 2/1998 | Horrocks et al. |
| 2009/0018449 A1 | 1/2009 | Raju |

(Continued)

FOREIGN PATENT DOCUMENTS

| JP | 2005124815 A | 5/2005 |
| JP | 2008246010 A | 10/2008 |

(Continued)

OTHER PUBLICATIONS

Lu et al. ( "A new algorithm for linear and nonlinear ARMA model parameter estimation using affine geometry"; IEE transaction on biomedical engineering, vol. 48, No. 10, Oct. 2001).*

(Continued)

*Primary Examiner* — Oommen Jacob
*Assistant Examiner* — Shahdeep Mohammed
(74) *Attorney, Agent, or Firm* — Junjie Feng

(57) ABSTRACT

A method and system for evaluating physiological properties of a segment of blood vessel is provided. The method includes: acquiring a first measurement and a second measurement respectively at the first point and the second point; obtaining a transfer function configured to produce an output given an input, using the first measurement and the second measurement as the input and the output respectively; and determining the physiological properties of the section of the blood vessel based on the transfer function. The transfer function can be a velocity transfer function based on the blood velocity waveforms, or can be a pressure transfer function based on the blood pressure waveforms. The method and system can be used to non-invasively diagnose PH, COPD, and PA impedance in a pulmonary artery, and to detect a stenosis in a coronary artery.

20 Claims, 35 Drawing Sheets

(51) Int. Cl.
*A61B 5/0215* (2006.01)
*A61B 5/022* (2006.01)
*A61B 5/026* (2006.01)
*A61B 5/00* (2006.01)
*A61B 5/085* (2006.01)
*A61B 8/08* (2006.01)

(52) U.S. Cl.
CPC ........ *A61B 5/0263* (2013.01); *A61B 5/02108* (2013.01); *A61B 5/085* (2013.01); *A61B 5/681* (2013.01); *A61B 5/6852* (2013.01); *A61B 5/6876* (2013.01); *A61B 5/7225* (2013.01); *A61B 5/7246* (2013.01); *A61B 5/7282* (2013.01); *A61B 8/0891* (2013.01); *A61B 8/488* (2013.01); *A61B 8/5223* (2013.01); *A61B 2503/40* (2013.01)

(56) References Cited

U.S. PATENT DOCUMENTS

| | | | |
|---|---|---|---|
| 2009/0154784 A1* | 6/2009 | Igarashi | A61B 5/0073 382/131 |
| 2010/0121204 A1 | 5/2010 | Utsuno et al. | |
| 2011/0103665 A1 | 5/2011 | Gulsun et al. | |
| 2013/0121545 A1* | 5/2013 | Feng | G06T 7/0014 382/128 |
| 2014/0086461 A1 | 3/2014 | Yao et al. | |
| 2014/0114184 A1* | 4/2014 | Klaiman | A61B 6/507 600/431 |
| 2014/0163403 A1* | 6/2014 | Lenox | A61B 5/026 600/504 |
| 2016/0000341 A1 | 1/2016 | Rotman et al. | |
| 2016/0302672 A1* | 10/2016 | Kuri | A61B 8/04 |
| 2017/0088897 A1* | 3/2017 | Rowlands | C12Q 1/6883 |
| 2017/0325783 A1* | 11/2017 | White | A61B 8/0883 |

FOREIGN PATENT DOCUMENTS

| | | |
|---|---|---|
| WO | 2012021765 A2 | 2/2012 |
| WO | 2016081517 A2 | 5/2016 |

OTHER PUBLICATIONS

Schack et al. (Methods of dynamic spectral analysis by self exciting autoregressive moving average models and their application to analyzing biosignals; Med. and Biol. and Comput., 1995, 33, 492-498).*

Schack ( "Methods of dynamic spectral analysis by self-exciting autoregressive moving average models and their application to analysing biosignais"; Med. & Biol. Eng. & Comput., 1995, 33, 492-498).*

International Search Report and Written Opinion in PCT/US2017/060979 dated Feb. 14, 2018.

Corrected European Search Opinion for European Patent Application No. 17869538.3 (National Entry Application of PCT/US2017/060979, related to this instant US application), dated Dec. 17, 2019.

Simone Balocco et al. "Estimation of viscoelastic properties of vessel walls using a computational model and Doppler ultrasound", Physics in Medicine and Biology, Institute of Physics Publishing, Bristol GB, vol. 55, No. 12, May 28, 2010 (May 28, 2010), pp. 3557-3575, XP020192470; ISSN: 0031-9155, DOI: 10.1088/0031-9155/55/12/019.

Xiao Hanguang et al: "A novel method of artery stenosis diagnosis using transfer function and support vector machine based on transmission line model:A numerical simulation and validation study", Computer Methods and Programs in Biomedicine, Elsevier, Amsterdam, NL, vol. 129, Mar. 14, 2016 (Mar. 14, 2016), pp. 71-81, XP029504938, ISSN: 0169-2607, DOI: 10.1 016/J.CMPB.2016.03.005.

Notice of Reasons for Refusal for Japanese Patent Application No. 2019-522389 (National Entry Application of PCT/US2017/060979, related to this instant US application), dated Jun. 23, 2020.

* cited by examiner

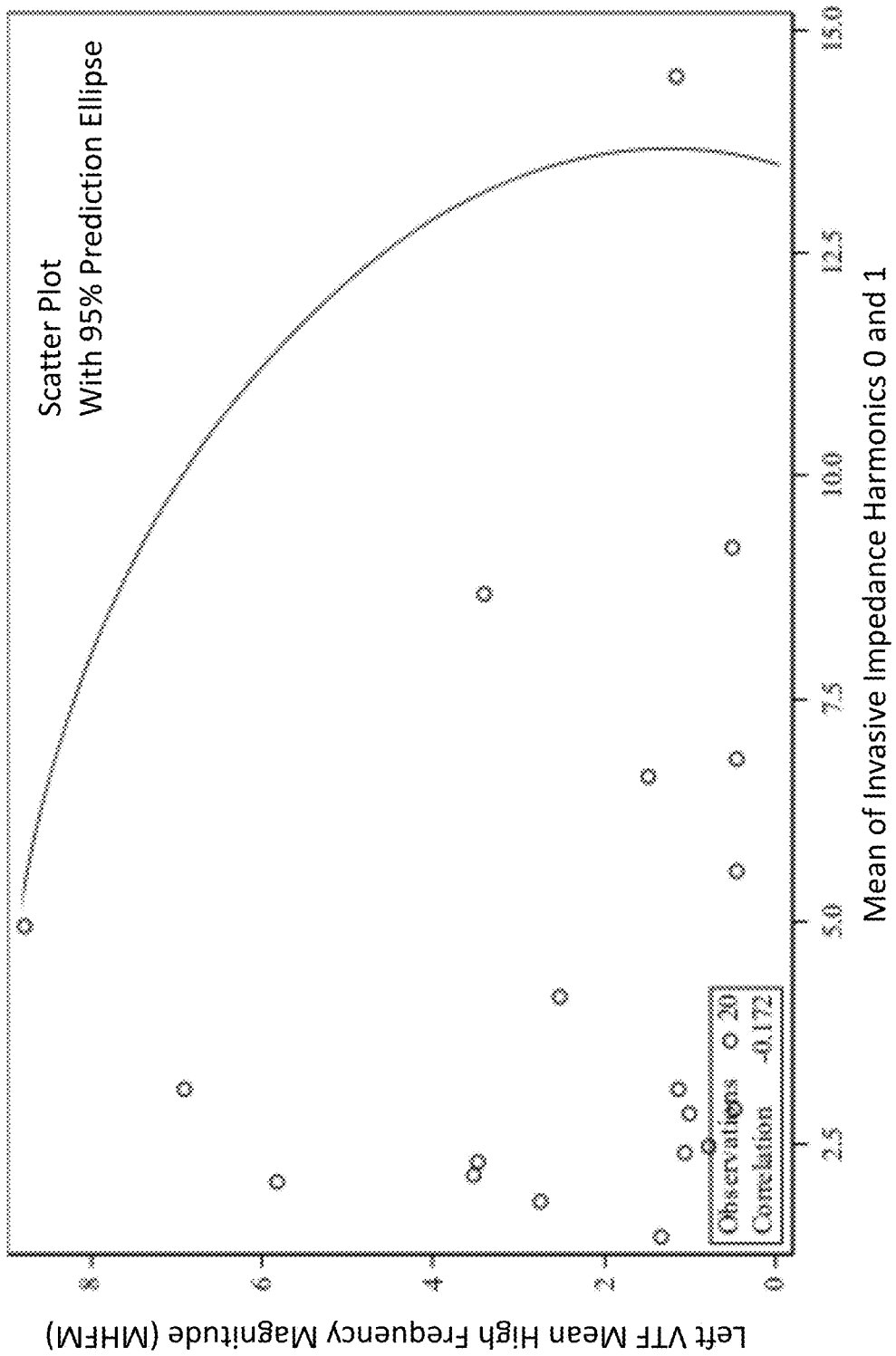

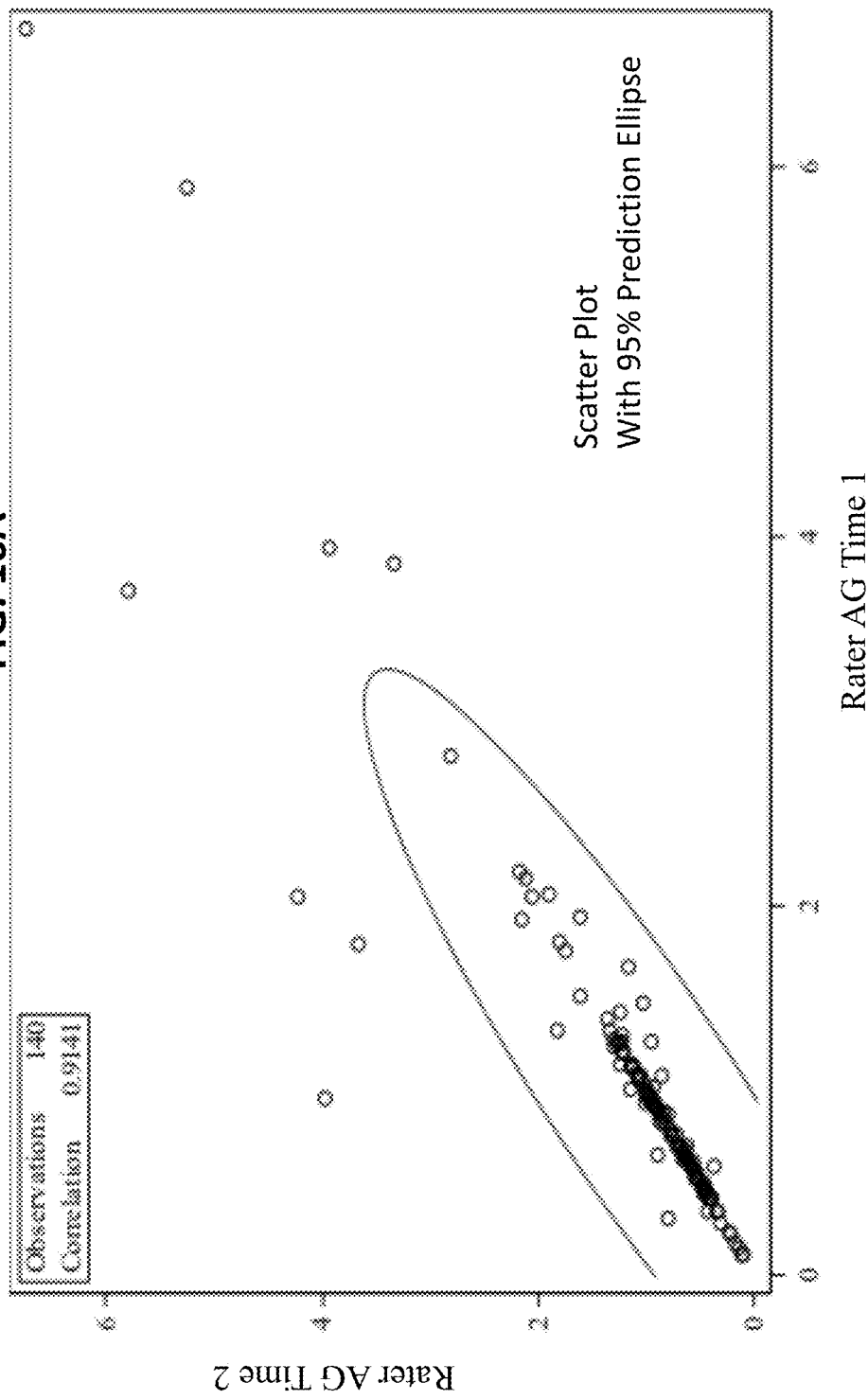

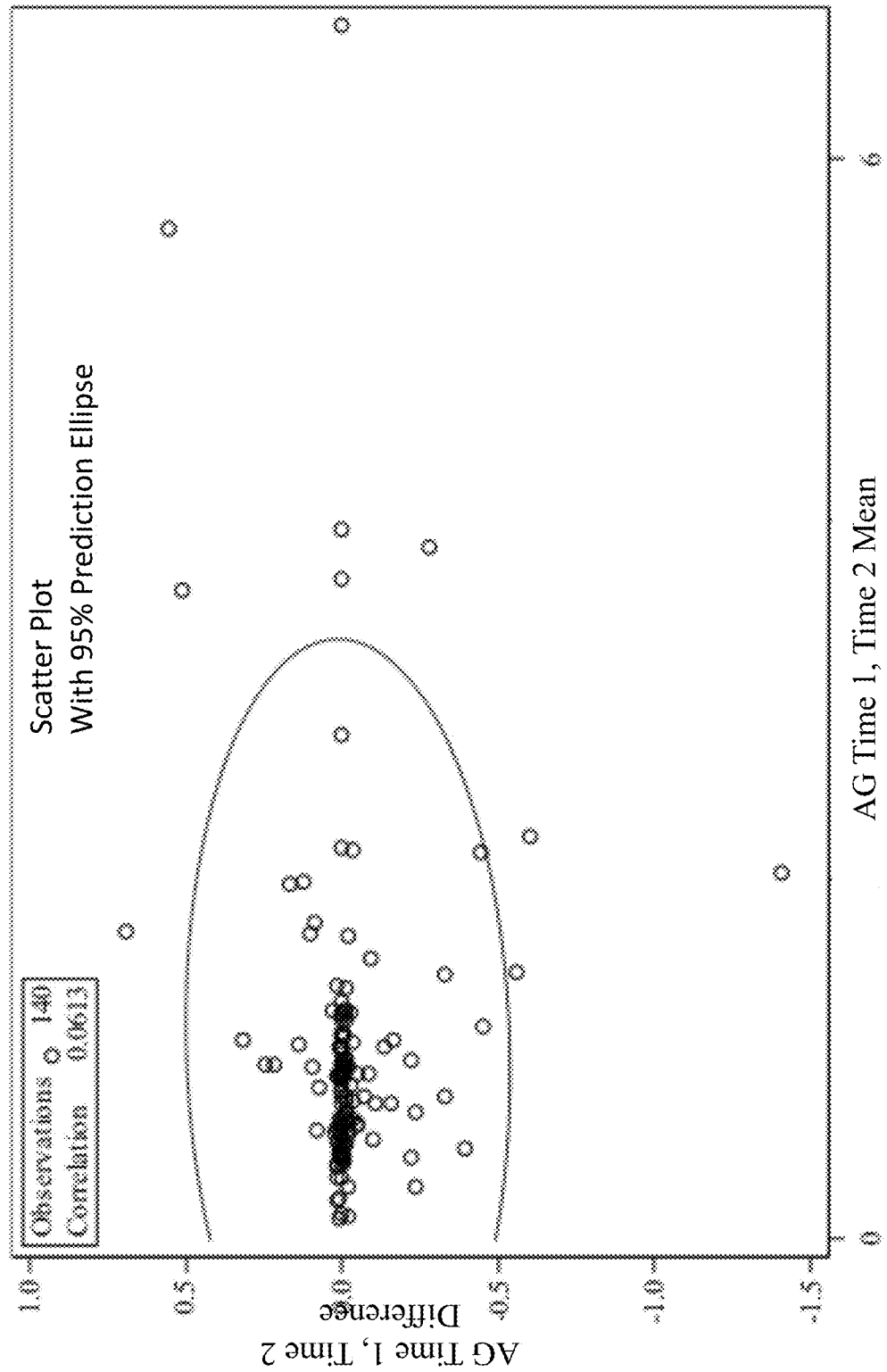

METHOD AND SYSTEM FOR EVALUATING BLOOD VESSEL

CROSS-REFERENCE TO RELATED APPLICATION

The present application claims priority to U.S. Patent Application No. 62/420,366 filed on Nov. 10, 2016, the disclosure of which is hereby incorporated by reference in its entirety.

STATEMENT REGARDING FEDERALLY SPONSORED RESEARCH

This invention was made with government support under HL104018 awarded by the National Institutes of Health. The government has certain rights in the invention.

TECHNICAL FIELD

The present invention relates generally to the field of medical diagnostic and therapeutic devices, specifically to a method and system for evaluating blood vessel, and in more particular to a method and system for determining the material properties of arteries such as compliance and the presence of lesions.

BACKGROUND

Normal arteries are elastic and expand during ventricular systole in response to increased blood flow and then recoil to their original state. Many diseases result in changes to the compliance and other arterial material properties. For example, arteries can become stiff due to atherosclerosis or increased blood pressure, as in pulmonary hypertension (PH), or become occluded with lesions, as in coronary artery disease. In addition, changes to arterial material properties can be an early physiological manifestation of disease. Measuring arterial material properties can provide physicians with important information for making clinical decisions and managing patients with arterial diseases.

In clinical situations, PH is defined based on elevated pulmonary artery (PA) pressure and/or pulmonary vascular resistance (PVR) measured with a right heart catheterization (RHC) procedure. However, PVR measurements provide spurious physiologic information in PH because its derivation based on assumptions of uniform pulmonary conduits with static and not pulsatile pressure-volume relationships.

Pulmonary Impedance, Z(f), is a measure of the opposition to PA flow and is defined as the ratio of Fourier transform of the blood pressure, P(f) to blood flow Q(f) at a point in an artery. Compared to PVR, it is a more accurate measure of afterload in pulmonary circulation. The pulmonary impedance magnitude has the same units as resistance, but it also describes the opposition to pulsations in the pulmonary vascular bed. Impedance is frequency dependent and is modulated by a) heart rate b) vessel stiffness or viscoelastic properties of the vessel and c) wave reflections. Pulmonary impedance is also closely coupled to ventricular geometry, function and chamber pressures.

Animal experiments have indicated that hypoxia in its early stages leads to vasoconstriction of the predominantly distal pulmonary arterial bed and increased stiffness of proximal vessels. These effects become pronounced with disease progression and lead to: a) elevated mean PA pressure due to increased distal pulmonary arterial bed tone and b) increased pulse pressure with decreased pulmonary distensiblity, increased arterial pulse wave velocity, and abnormal reflected waves in the proximal pulmonary arterial system. A recent study in humans using a combination of MRI approach and right heart catheterization (RHC) has demonstrated that PA stiffness increases early in the course of PH (even when PH is detectable only with exercise and before overt pressure elevations occur at rest).

Pulse wave velocity (PWV) is another measure of arterial stiffness. Under certain ideal assumptions, PWV is related to the Young's modulus (E) of the artery by a square root:

$$PWV = \sqrt{\frac{Eh}{2r\rho}}$$

where $\rho$=density of blood (approx. 1.05 g/ml) and h/2r is the wall thickness/diameter. PWV is measured as the difference between 2 recording sites in the line of pulse travel divided by the delay between corresponding points on the wave (of pressure or of flow), which are not affected by the wave reflection. One major difficulty in measuring PWV is related to the change in the shape of pressure and flow waves with distance that makes it difficult to assign a single value that is definitive for the entire wave.

Impedance calculations are based on an analogy with alternating current (AC) electrical circuit analysis, where a time-varying voltage across a network of resistors, inductors, and capacitors causes a time-varying current to flow through the network (FIG. 1A). The voltage across the network and the current flowing through the network are related by a frequency-dependent quantity called impedance. Time-varying voltage can be decomposed into frequency components using Fourier analysis. In electrical circuits, the impedance describes how each frequency component in the voltage is related to its counterpart in the current in terms of magnitude and phase. The impedance magnitude describes how each frequency component is amplified (magnitude>1) or attenuated (magnitude<1) by the circuit. The impedance phase describes how the circuit shifts each frequency component in time.

In the PA system, impedance describes the frequency dependent relationship between pressure (analogous to voltage) and flow (analogous to current). The compliance/stiffness of the pulmonary arteries and the resistance from blood viscosity and the distal capillary bed determine the frequency-dependent way pressure and flow are related (analogous to the resistor, capacitor, inductor network). Impedance therefore considers the pulsatile nature of blood flow. At a frequency of 0 Hertz, the impedance describes the relationship between mean PA pressure and mean PA flow and is equal to pulmonary vascular resistance (PVR). At low frequencies, resistive terms dominate due to changes in PA radius and to a lesser extent blood viscosity dominate the impedance magnitudes. With increased arterial stiffness, the zero frequency magnitude increase, there is decreased rate of decline of magnitude with corresponding increase in frequency when the first minimum of magnitude occurs (Nichols, W. and M. O'Rourke, *McDonald's Blood Flow in Arteries.* 5th ed. 2005, London: Hodder Arnold.). Also at low frequencies, the impedance phase is negative because the onset of flow occurs before the onset of pressure with the low-frequency slope being proportional to the time delay between the two onsets. Terms related to PA compliance dominate the higher-frequency impedance magnitudes. As a result, impedance magnitudes in animal studies under serotonin or induced hypoxia which increase vascular resistance and PA stiffness are larger than controls (Nichols, W. and M. O'Rourke, *McDonald's Blood Flow in Arteries*. 5th ed. 2005, London: Hodder Arnold.). Similar results have been shown in humans with PH, where impedance magnitudes in these patient groups are larger than in controls (Nichols, W. and M. O'Rourke, *McDonald's Blood Flow in Arteries*. 5th ed. 2005, London: Hodder Arnold; Yin, F., *Ventricular/Vascular Coupling. Clinical, physiological and engineering aspects*. 1987, New York: Springer-Verlag.).

PA stiffness and pulmonary impedance is altered early in the evolution of pulmonary hypertensive vascular disease. Currently pulmonary impedance is not measured routinely as it requires invasive measurements. The ability to measure pulmonary impedance non-invasively using VTF can provide fundamental insights in the evaluation of patients with normal PA pressures or mild PH such as in patients with COPD and chronic left sided heart failure. Once validated, it has the potential to become the non-invasive tool of choice in detection of early PA stiffness. The ability to non-invasively evaluate the right ventricle (RV)-PA axis and detect patients who could develop RV dysfunction will therefore provide a mechanistic rationale for therapeutic interventions that target early changes in cardiac structure and function in otherwise mild PH.

Impedance and PWV can also be used to evaluate the material properties of systemic arteries, such as the aorta, with a left heart catheterization (LHC). However, there are relatively lower pulsatile energy losses within the systemic circulation because of a higher overall resistance and lower distensibility of the systemic vessels. In dogs, the ratio of pulsatile to total external ventricular work is 25% in the pulmonary vascular bed and 10% in the systemic circulation.

Lesions, such as those in coronary artery disease, also affect arterial material properties. In coronary artery disease, it is important to know where the stenoses are, how many there are, and the extent of the blockages. This information, along with other factors, is used by a cardiologist to decide if the disease should be treated medically, with a stent, or with coronary by-pass surgery. Information on the stenosis is traditionally obtained with an angiogram, which uses an invasive catheter to introduce a dye into the artery while it is being imaged with a fluoroscope. However, this procedure only provides information on the geometry of the stenosis and does not evaluate how much blood is flowing through it. More recently, the fractional flow reserve (FFR) is used to evaluate stenoses. The FFR is the ratio of mean pressure measurements obtained at two points during hyperemia: one proximal to the stenosis and one distal to the stenosis. The FFR can be used to assess how much the stenosis affects functioning of the artery, but stenoses can not only change in the amplitude of the pressure waveform, but also the shape of the waveform, which contains important information about the functional capacity of the artery. The instantaneous free-wave ratio (iFR) provides an instantaneous pressure ratio during the wave-free period when the resistance is constant and minimized in the cardiac cycle. The iFR, however, only looks at a portion of the pressure wave and can potentially miss characteristics of the pressure waves that can provide useful information on the functional capacity of the stenosis.

SUMMARY OF THE INVENTION

In light of the issues associated with current technology, the present disclosure provides a method and system for evaluating blood vessel.

In a first aspect, the disclosure provides a method for evaluating physiological properties of a blood vessel at a segment thereof between a first point and along a direction of blood flow a second point in a subject. The method comprises the steps of:

acquiring a first measurement and a second measurement respectively at the first point and the second point;

obtaining a transfer function configured to produce an output given an input, using the first measurement and the second measurement as the input and the output respectively; and determining the physiological properties of the section of the blood vessel based on the transfer function.

Herein in the method, each of the first measurement and the second measurement can be one of blood velocity waveform, blood flow waveform, or blood pressure waveform.

According to some embodiments of the method, each of the first measurement and the second measurement is blood velocity waveform or blood flow waveform, and the acquiring a first measurement and a second measurement respectively at the first point and the second point is by means of a phase-contrast magnetic resonance imaging, a Doppler ultrasound, or an invasive catheter. It is noted that besides these conventional means, other devices and approaches capable of obtaining the blood velocity waveform or blood flow waveform are also possible.

According to some other embodiments of the method, each of the first measurement and the second measurement is blood pressure waveform, and the acquiring a first measurement and a second measurement respectively at the first point and the second point is by means of an invasive catheter, a tonometric device, or a fitness wristband capable of measuring blood pressure. It is noted that besides these conventional devices, other devices and approaches capable of obtaining the blood pressure waveform are also possible.

In the method disclosed herein, the transfer function can be linear or non-linear, but is preferably linear.

According to some embodiments of the method, the transfer function is implemented in a time domain as an autoregressive moving average (ARMA) model:

$$Y_k = X_k + \sum_{i=1}^{p} b_i Y_{k-i} + \sum_{i=1}^{q} a_i X_{k-i};$$

where k is a sample index, $X_k$ are samples of the first measurement, $Y_k$ are samples of the second measurement, p is a number of moving average terms, q is a number of autoregressive terms, and $a_i$ and $b_i$ are coefficients. Accordingly, the step of determining the physiological properties of the section of the blood vessel based on the transfer function comprises:

determining the physiological properties of the section of the blood vessel based on parameters p, q, $a_i$, and $b_i$.

According to some other embodiments of the method, the transfer function is implemented in a frequency domain, and is expressed as:

$$S_M(f) = M_{output}(f) / M_{input}(f);$$

where f is frequency, $M_{output}(f)$ is the second measurement, and $M_{input}(f)$ is the first measurement.

In some embodiments of the method as described above, each of the first measurement and the second measurement is a blood velocity waveform, and the transfer function is a blood velocity function expressed as:

$$S_V(f)=V_{output}(f)/V_{input}(f);$$

where $V_{output}(f)$ is the second measurement, and $V_{input}(f)$ is the first measurement.

In some other embodiments of the method as described above, each of the first measurement and the second measurement is a blood pressure waveform; and the transfer function is a blood pressure function expressed as:

$$S_P(f)=P_{output}(f)/P_{input}(f);$$

where $P_{output}(f)$ is the second measurement, and $P_{input}(f)$ is the first measurement.

In yet some other embodiments of the method as described above, each of the first measurement and the second measurement is a single heartbeat pressure waveform; and the transfer function is a single heartbeat pressure function expressed as:

$$S_P(f)=P_{output}(f)/P_{input}(f);$$

where $P_{output}(f)$ is the second measurement, and $P_{input}(f)$ is the first measurement.

In some embodiments of the method where the transfer function is expressed as:

$$S_M(f)=M_{output}(f)/M_{input}(f);$$

the determining the physiological properties of the section of the blood vessel based on the transfer function comprises the following sub-steps:

decomposing the first measurement into a series of first harmonic components and the second measurement into a series of second harmonic components, wherein the series of first harmonic components and the series of second harmonic components correspond to one another at each harmonic number;

forming a series of transfer function harmonics, each obtained by dividing each second harmonic magnitude by a corresponding first harmonic magnitude; and determining the physiological properties of the section of the blood vessel based on one, or a linear combination, of the series of transfer function harmonics.

Herein the linear combination of the series of transfer function harmonics can be, for example, an average of harmonics 5 and 6, but can also be an average of several other harmonics.

According to some embodiments of the method as described above, the blood vessel is a pulmonary artery, the step of acquiring a first measurement and a second measurement respectively at the first point and the second point comprises:

performing a PC-MM (phase-contrast magnetic resonance imaging) at the first point and the second point of the pulmonary artery to respectively obtain a first blood velocity waveform and a second blood velocity waveform.

Correspondingly, the step of obtaining a transfer function configured to produce an output given an input, using the first measurement and the second measurement as the input and the output respectively comprises:

obtaining a velocity transfer function (VTF) based on the first blood velocity waveform and the second blood velocity waveform.

Herein, the segment of pulmonary artery can be between a main pulmonary artery (MPA) and a right pulmonary artery (RPA) proximal to a bifurcation; between the MPA and a left pulmonary artery (LPA) proximal to the bifurcation; between the RPA proximal and distal to the bifurcation; or between the LPA proximal and distal to the bifurcation.

According to some embodiments, in the step of determining the physiological properties of the section of the blood vessel based on the transfer function, the sub-step of determining the physiological properties of the section of the blood vessel based on one, or a linear combination, of the series of transfer function harmonics comprises:

determining that the subject has pulmonary hypertension (PH) if the subject has an elevated mean high frequency magnitude (MHFM) for the VTF compared with subjects absent of PH.

According to some other embodiments, in the step of determining the physiological properties of the section of the blood vessel based on the transfer function, the sub-step of determining the physiological properties of the section of the blood vessel based on one or a linear combination of the series of transfer function harmonics comprises:

determining that the subject has chronic obstructive pulmonary disease (COPD) if the subject has an elevated mean high frequency magnitude (MFHM) for the VTF compared with subjects absent of COPD.

According to some embodiments of the method, the blood vessel is a pulmonary artery. The segment of pulmonary artery can be between a main pulmonary artery (MPA) and a right pulmonary artery (RPA) proximal to a bifurcation; between the MPA and a left pulmonary artery (LPA) proximal to the bifurcation; between the RPA proximal and distal to the bifurcation; or between the LPA proximal and distal to the bifurcation. Preferably, the segment of pulmonary artery is between the RPA proximal and distal to the bifurcation.

The step of acquiring a first measurement and a second measurement respectively at the first point and the second point comprises:

performing a cardiac MRI (CMR) at the first point and the second point of the pulmonary artery to respectively obtain a first blood velocity waveform and a second blood velocity waveform;

and correspondingly, the step of obtaining a transfer function configured to produce an output given an input, using the first measurement and the second measurement as the input and the output respectively comprises:

obtaining a velocity transfer function (VTF) based on the first blood velocity waveform and the second blood velocity waveform.

Herein the CMR may be cine or phase contrast based.

In the method as described above, in the step of determining the physiological properties of the section of the blood vessel based on the transfer function, the sub-step of determining the physiological properties of the section of the blood vessel based on one, or a linear combination, of the series of transfer function harmonics comprises:

determining that the subject has PA impedance at the section of the blood vessel if the subject has an elevated mean high frequency magnitude (MHFM) for the VTF compared with subjects absent of the PA impedance.

It is noted that in any of the above embodiments of the method, the mean high frequency magnitude (MHFM) is defined as an average of harmonics 5 and 6 based on the transfer function, and an "elevated MHFM" is defined if the MHFM from the subject under investigation is at least 30% higher, and preferably at least 50% higher, than a mean value of MHFM from a population of subjects absent of the disease of interest (such as PH, or COPD).

In some specific embodiments, the MHFM for the calculated VTF from the subject under investigation is observed to be at least 30% higher than a mean value of MHFM from a population of subjects absent of PH or COPD, and the subject is suspected to have COPD. In other embodiments, the MHFM for the calculated VTF from the subject under investigation is observed to be about 50% higher than a mean value of MHFM from a population of subjects absent of PH or COPD, and the subject is suspected to have PH.

According to some embodiments of the method, the blood vessel is a coronary artery, the step of acquiring a first measurement and a second measurement respectively at the first point and the second point comprises:

obtaining a series of single heartbeat waveforms by means of an invasive catheter while pulling the invasive catheter from the first point to the second point of the coronary artery.

Correspondingly, the step of obtaining a transfer function configured to produce an output given an input comprises:

calculating a series of single heartbeat pressure functions $S_{Pi}(f)$ based on:

$$S_{Pi}(f) = P_{output}(f)/P_{reference}(f);$$

where f is frequency, $P_{output}(f)$ is each of the series of single heartbeat waveforms, and $P_{reference}(f)$ is an earliest timepoint single heartbeat waveform of the series of single heartbeat waveforms.

Furthermore, the step of determining the physiological properties of the section of the blood vessel based on the transfer function comprises:

determining that the subject has a stenosis at one point in the segment of the coronary artery if a big change in harmonic 3 magnitude is observed while the invasive catheter crosses the one point.

Herein the "big change in harmonic 3 magnitude" is defined as the situation where the harmonic 3 magnitude is at least 100% higher than a mean value in upstream healthy sections of the coronary artery.

In any the embodiments of the method, the blood vessel can be an artery or a vein, and the subject can be a human or an animal.

In a second aspect, the disclosure further provides a system for evaluating physiological properties of a segment of a blood vessel in a subject. The system includes a measuring device and a processing device.

The measuring device is configured to acquire, and to transmit to the processing device, a first measurement at a first point and a second measurement at a second point, wherein the first point and the second point are along a blood flow direction within the segment of the blood vessel. The processing device is configured to calculate a transfer function configured to produce an output given an input, with the first measurement and the second measurement as the input and the output respectively, and to determine the physiological properties of the section of the blood vessel based on the transfer function.

According to some embodiments, the processing device comprises a transfer function calculation unit and a physiological property determination unit. The function calculation unit is configured to calculate the transfer function; and the physiological property determination unit is configured to determine the physiological properties of the section of the blood vessel based on the transfer function.

Herein the system can be an assembly of several separately disposed devices including the measuring device and the processing device, or can be an integrated apparatus that is equipped with several functionalities that are each comparable to each functionality of each of the several separately disposed devices including the measuring device and the processing device.

Herein the processing device can comprise a processor and a memory, wherein the memory is configured to store a software program, and the processor is configured to perform a calculation based on the software program stored in the memory to thereby perform a specified task. Each of the transfer function calculation unit and the physiological property determination unit can include a separate processor and a separate memory storing a separate software program, or can share a common processor but with a separate software program stored in a shared common memory. There are no limitations herein.

According to some embodiments of the system, the measuring device can include a magnetic resonance imaging (MRI) device, a Doppler ultrasound device, or an invasive catheter, and each of the first measurement and the second measurement acquired by the measuring device can be blood velocity waveform or blood flow waveform.

According to some other embodiments of the system, the measuring device can include an invasive catheter, a tonometric device, or a fitness wristband capable of measuring blood pressure, and each of the first measurement and the second measurement acquired by the measuring device can be blood pressure waveform.

According to some embodiments of the system, the processing device is configured to calculate the transfer function based on a linear model.

In some embodiments of the system as described above, the transfer function is in a time domain, and the processing device is configured to calculate the transfer function based on an autoregressive moving average (ARMA) model:

$$Y_k = X_k + \sum_{i=1}^{p} b_i Y_{k-i} + \sum_{i=1}^{q} a_i X_{k-i};$$

where k is a sample index, $X_k$ are samples of the first measurement, $Y_k$ are samples of the second measurement, p is a number of moving average terms, q is a number of autoregressive terms, and $a_i$ and $b_i$ are coefficients. Correspondingly, the processing device is configured to determine the physiological properties of the section of the blood vessel based on parameters p, q, $a_i$, and $b_i$.

In some other embodiments of the system as described above, the transfer function is in a frequency domain, and the processing device is configured to calculate the transfer function based on formula:

$$S_M(f) = M_{output}(f)/M_{input}(f);$$

where f is frequency, $M_{output}(f)$ is the second measurement, and $M_{input}(f)$ is the first measurement.

According to some embodiments, the measuring device is configured to acquire a blood velocity waveform for each of the first measurement and the second measurement; and the processing device is configured to calculate the transfer function based on formula:

$$S_V(f) = V_{output}(f)/V_{input}(f);$$

where $V_{output}(f)$ is the second measurement, and $V_{input}(f)$ is the first measurement.

According to some other embodiments, the measuring device is configured to acquire a blood pressure waveform for each of the first measurement and the second measurement; and the processing device is configured to calculate the transfer function based on formula:

$$S_P(f) = P_{output}(f)/P_{input}(f);$$

where $P_{output}(f)$ is the second measurement, and $P_{input}(f)$ is the first measurement.

According to yet some other embodiments, the measuring device is configured to acquire a single heartbeat pressure waveform for each of the first measurement and the second measurement; and the processing device is configured to calculate the transfer function based on formula:

$$S_P(f)=P_{output}(f)/P_{input}(f);$$

where $P_{output}(f)$ is the second measurement, and $P_{input}(f)$ is the first measurement.

In some other embodiments of the system, the processing device is configured to:

decompose the first measurement into a series of first harmonic components and the second measurement into a series of second harmonic components, wherein the series of first harmonic components and the series of second harmonic components correspond to one another at each harmonic number;

form a series of transfer function harmonics, each obtained by dividing each second harmonic magnitude by a corresponding first harmonic magnitude; and determine the physiological properties of the section of the blood vessel based on one, or a linear combination, of the series of transfer function harmonics.

According to some embodiments of the system disclosed herein, the blood vessel is a pulmonary artery. The measuring device comprises a magnetic resonance imaging (MRI) device, which is configured to perform a PC-MM at the first point and the second point of the pulmonary artery to respectively obtain a first blood velocity waveform and a second blood velocity waveform. The processing device is configured to obtain a velocity transfer function (VTF) based on the first blood velocity waveform and the second blood velocity waveform.

Herein, the segment of pulmonary artery can be between a main pulmonary artery (MPA) and a right pulmonary artery (RPA) proximal to a bifurcation; between the MPA and a left pulmonary artery (LPA) proximal to the bifurcation; between the RPA proximal and distal to the bifurcation; or between the LPA proximal and distal to the bifurcation.

According to some embodiments of the system, the processing device is configured to determine whether the subject has pulmonary hypertension (PH) based on whether the subject has an elevated mean high frequency magnitude (MHFM) for the VTF compared with subjects absent of PH.

According to some other embodiments of the system, the processing device is configured to determine whether the subject has COPD based on whether the subject has an elevated mean high frequency magnitude (MFHM) for the VTF compared with subjects absent of COPD.

According to some embodiments of the system disclosed herein, the blood vessel is a pulmonary artery. The measuring device comprises a magnetic resonance imaging (MRI) device, which is configured to perform a cardiac MM (CMR) at the first point and the second point of the pulmonary artery to respectively obtain a first blood velocity waveform and a second blood velocity waveform. The processing device is configured to obtain a velocity transfer function (VTF) based on the first blood velocity waveform and the second blood velocity waveform.

The segment of pulmonary artery can be between a main pulmonary artery (MPA) and a right pulmonary artery (RPA) proximal to a bifurcation; between the MPA and a left pulmonary artery (LPA) proximal to the bifurcation; between the RPA proximal and distal to the bifurcation; or between the LPA proximal and distal to the bifurcation.

Preferably, the segment of pulmonary artery is between the RPA proximal and distal to the bifurcation.

Accordingly, the processing device is configured to determine whether the subject has PA impedance at the section of the blood vessel based on whether the subject has an elevated mean high frequency magnitude (MHFM) for the VTF compared with subjects absent of the PA impedance.

It is noted that in any of the above embodiments of the system, the mean high frequency magnitude (MHFM) is defined as an average of harmonics 5 and 6 based on the transfer function, and an "elevated MHFM" is defined if the MHFM from the subject under investigation is at least 30% higher, and preferably at least 50% higher, than a mean value of MHFM from a population of subjects absent of the disease of interest (such as PH, or COPD).

In some specific embodiments, the MHFM for the calculated VTF from the subject under investigation is observed to be at least 30% higher than a mean value of MHFM from a population of subjects absent of PH or COPD, and the subject is suspected to have COPD. In other embodiments, the MHFM for the calculated VTF from the subject under investigation is observed to be about 50% higher than a mean value of MHFM from a population of subjects absent of PH or COPD, and the subject is suspected to have PH.

According to some embodiments of the system disclosed herein, the blood vessel is a coronary artery. The measuring device comprises an invasive catheter, which is configured to obtain a series of single heartbeat waveforms while being pulled from the first point to the second point of the coronary artery. The processing device is configured to calculate a series of single heartbeat pressure functions $S_{Pi}(f)$ based on:

$$S_{Pi}(f)=P_{outputi}(f)/P_{reference}(f);$$

where f is frequency, $P_{outputi}(f)$ is each of the series of single heartbeat waveforms, and $P_{reference}(f)$ is an earliest time-point single heartbeat waveform of the series of single heartbeat waveforms; and the processing device is further configured to determine whether the subject has a stenosis at one point in the segment of the coronary artery based on whether a big change in harmonic 3 magnitude is observed while the invasive catheter crosses the one point. Herein the "big change in harmonic 3 magnitude" is defined as the situation where the harmonic 3 magnitude at one point is at least 100% higher than a mean value in upstream healthy sections of the coronary artery in the subject.

BRIEF DESCRIPTION OF THE DRAWINGS

FIGS. 14A and 14B illustrate scatter plots of the mean of invasive impedance harmonics 0-1 and VTF mean high frequency magnitude (MHFM) (average of the magnitudes of harmonics 5 and 6) in the RPA (FIG. 14A); mean of invasive impedance harmonics 0-1 and velocity transfer function MHFM in the LPA (FIG. 14B). 026 and 027 are the 2 'outliers';

FIGS. 16A, 16B, 16C, and 16D show scatter plots showing intra- (FIG. 16A, FIG. 16B) and inter- (FIG. 16C, FIG. 16D) observer correlation (FIG. 16A, FIG. 16C) and agreement (FIG. 16D, FIG. 16D) for individual harmonics of velocity transfer function.

DETAILED DESCRIPTION OF THE INVENTION

Figure 1A:
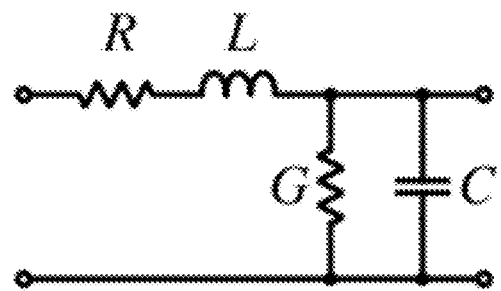
FIG. 1A illustrates that the concept of arterial impedance is based on an analogy to alternating current (AC) electrical circuit as shown where R=Resistance, L=Inductance G=Conductance and C=Capacitance.
Figure 1B:
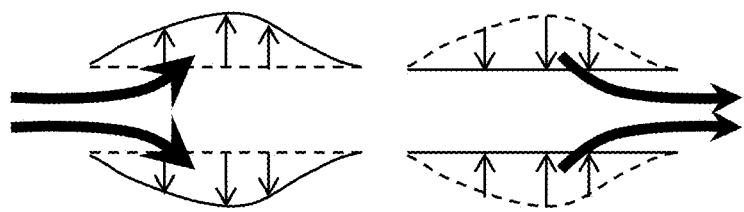
FIG. 1B illustrates that flow into pulmonary artery (PA) causes distension of the vessel wall which then recoils to the original state, which results in pulsatile component of the flow impedance.
Figure 1C:
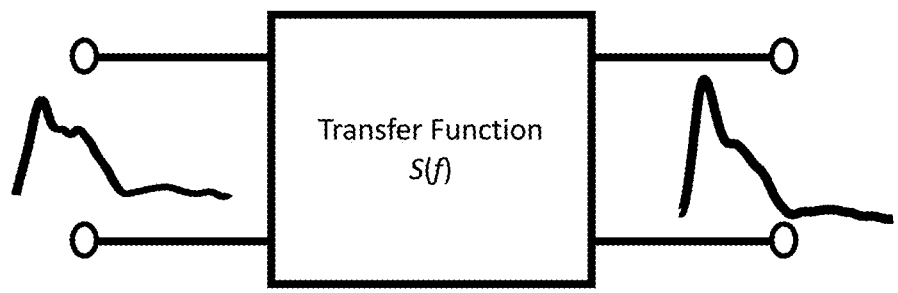
FIG. 1C illustrates a transfer function HO that provides mathematical relationship between the input and out waveforms and therefore provides a measure of viscoelastic properties of the vessel wall.
Figure 1D:
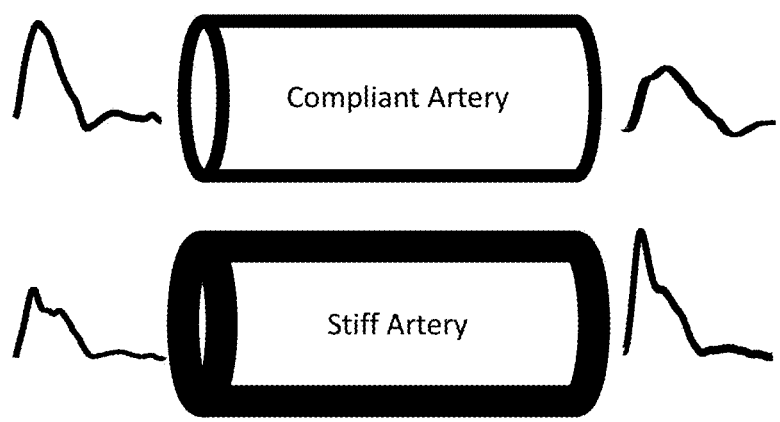
FIG. 1D illustrates a comparison between a compliant PA and a stiff PA, where the input velocity waveform changes in shape in a predictable fashion due to the viscoelastic properties of the vessel wall and geometry of the vessel.

This disclosure provides a method for detecting physiological properties of a blood vessel in a subject from measurements at two spatially separated points on the vessel. The method comprises the following steps:

S100: Acquiring the time-varying measurements at two, spatially separated points on a blood vessel;

S200: Computing a linear or non-linear transfer function that can produce the output given the input;

S300: Analyzing the parameters of the transfer function to evaluate the material properties of the section of vessel between the two points;

The following are noted. In the method as described above, one measurement is considered to be an input into a system and the other is considered to be an output, as shown in FIG. 1C. A transfer function is computed that produces the output waveform given the input waveform. The parameters of the transfer function are related to the physiological properties of the blood vessel.

Herein, the blood vessel can be an artery or a vein. The measurements can be blood velocity, blood flow, or blood pressure. The subject can be an animal or a human. Measurements of blood velocity or blood flow can be obtained from phase-contrast magnetic resonance imaging, Doppler ultrasound, an invasive catheter. Measurements of blood pressure can be obtained from an invasive catheter, or other pertinent vital sign measuring devices including, but not limited to, a tonometric device, a fitness wristband, or a blood pressure measurement device of another type. The transfer function can be linear or non-linear, time-invariant or time-varying. The transfer function can operate in the time domain or the frequency domain.

Herein, by evaluating the physiological properties of a blood vessel, the method can be used for detecting a blood vessel disease such as pulmonary hypertension (PH), chronic obstructive pulmonary disease (COPD), heart failure with preserved ejection fraction, heart failure with reduced ejection fraction, connective tissue disorders, coronary artery disease, or any other disease affecting the physiological properties of blood vessels.

Figure 2A:
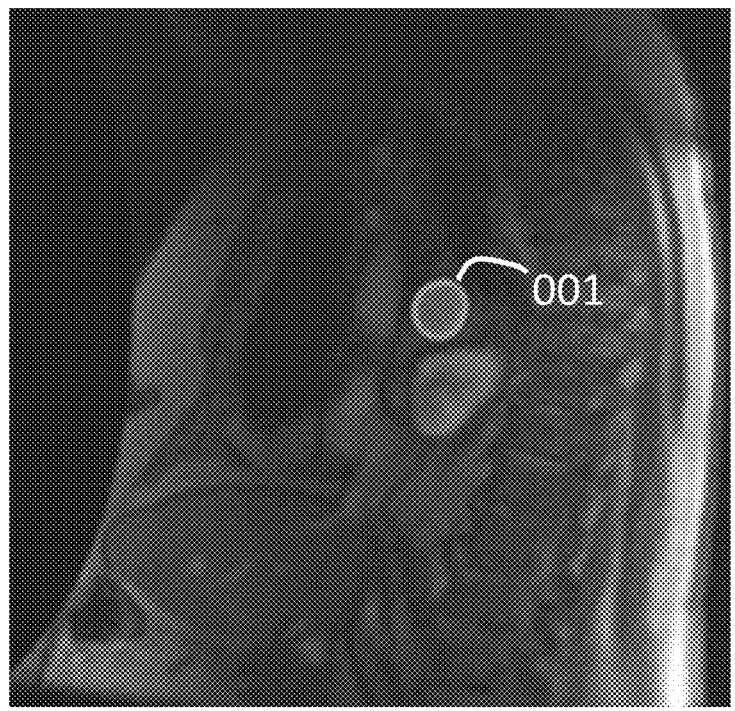
FIGS. 2A and 2B show respectively a magnitude image and a velocity image from phase contrast magnetic resonance imaging (PC-MRI) of a slice perpendicular to the right pulmonary artery proximal to the bifurcation, where 001 delineates the right pulmonary artery, and 002 delineates the right pulmonary artery, and the value of each pixel is the velocity of the corresponding tissue in the direction perpendicular to the slice.
Figure 2B:
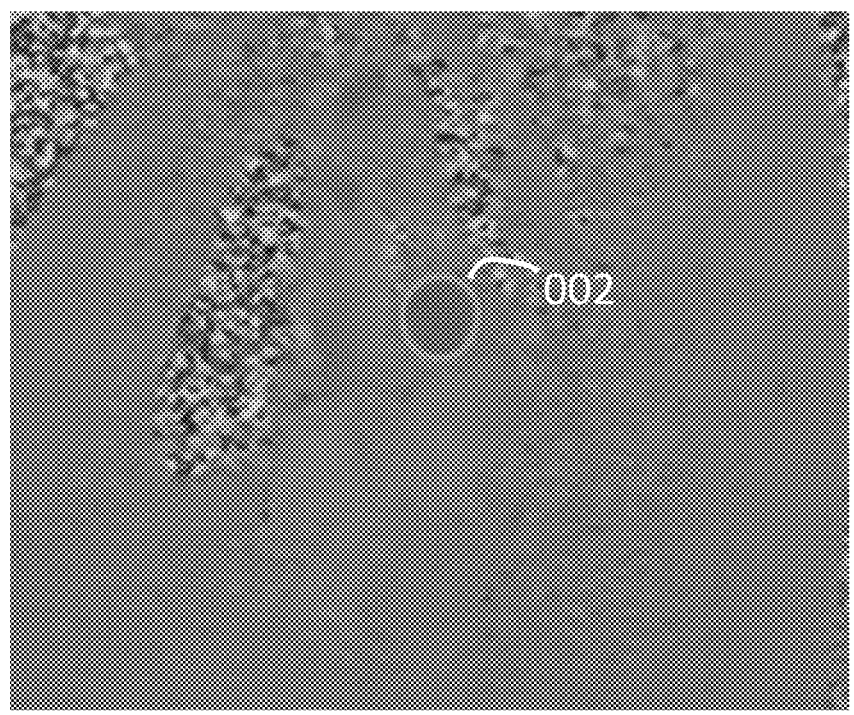
Figure 3:
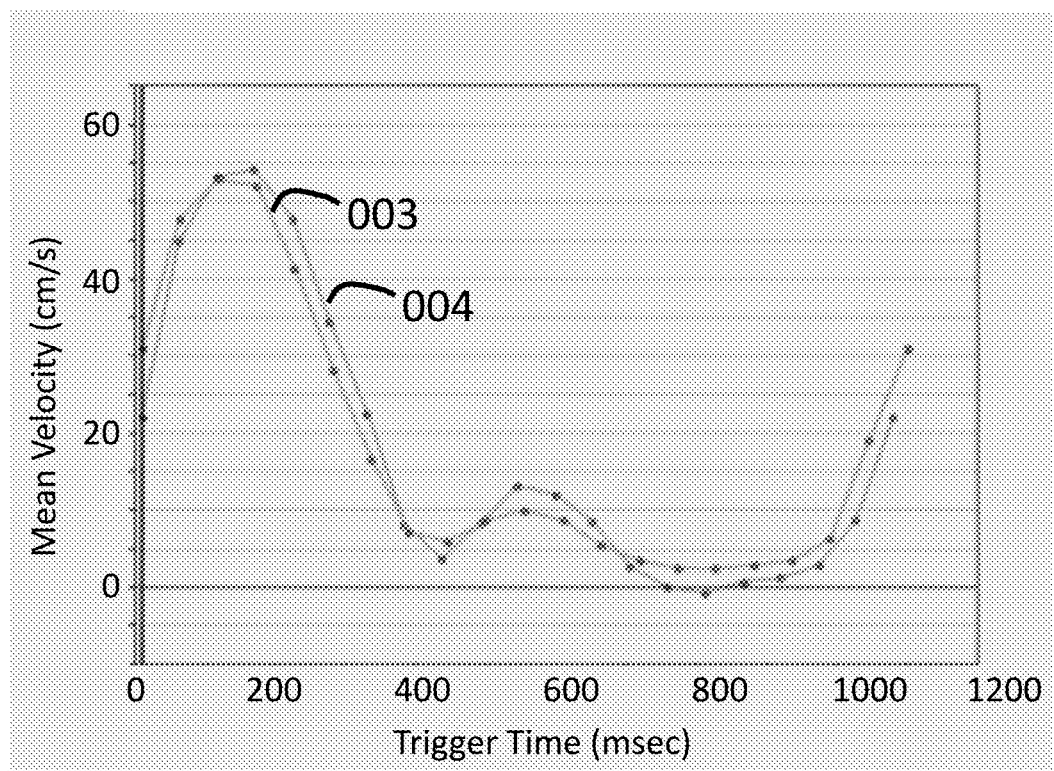
FIG. 3 illustrates mean velocity-time profiles in main (003) and right (004) pulmonary arteries obtained using phase contrast magnetic resonance imaging (PC-MRI)
Figure 4A:
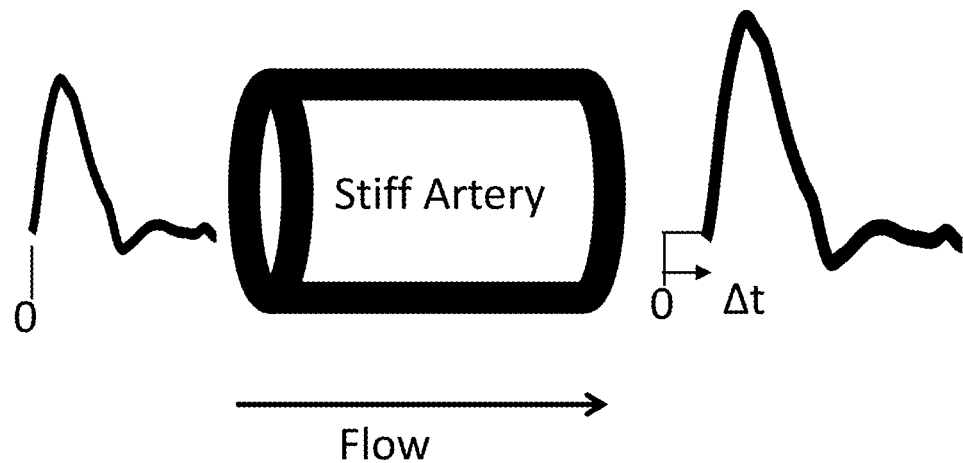
FIGS. 4A, 4B, 4C and 4D illustrate that, in a stiff artery, the output waveform is a scaled and shifted version of the input waveform (FIG. 4A), whereas in a compliant artery, the output waveform has a more complex relationship with the input waveform (FIG. 4C), and these relationships are respectively reflected in the corresponding transfer functions (|H(f)|) for the stiff artery (FIG. 4B) and the compliant artery (FIG. 4D)
Figure 4B:
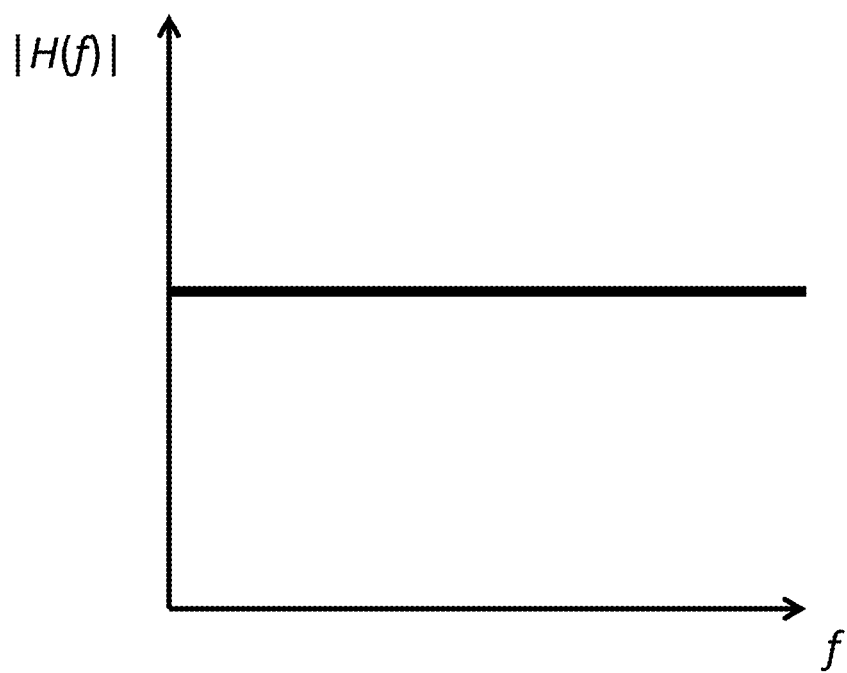
Figure 4C:
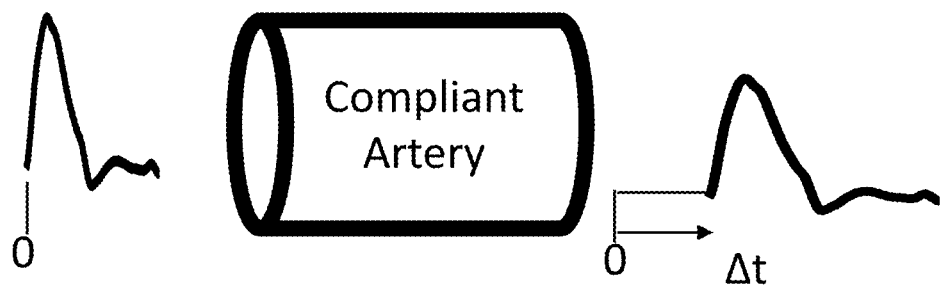
Figure 4D:
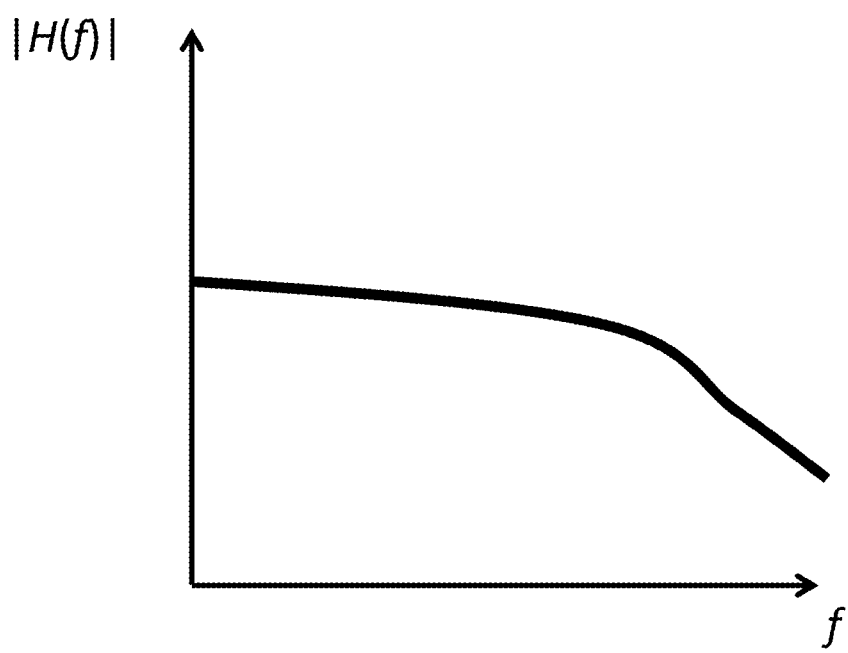

In one embodiment, blood velocity is measured non-invasively with phase-contrast cardiac magnetic resonance imaging (PC-MM) at two points in the pulmonary artery (PA) tree. PC-MRI is a technique where a slice through the body at an arbitrary orientation is prescribed and an image is produced of the velocities in a particular direction of tissues moving through the slice. In PC-MRI, two images are produced of each slice: a magnitude image (FIG. 2A) and a phase image (FIG. 2B). The magnitude image is an anatomical image similar to standard MRI images. In the phase image (FIG. 2B), each pixel represents a small cube of tissue, and the grayscale value of a pixel has a known linear relationship to the tissue's velocity in a particular direction. Velocities can be positive or negative. In PC-MRI, stationary tissues (velocity=0) are usually 50% gray. Tissues moving in one direction are bright, and tissues moving in the opposite direction are dark. The acquisition is synchronized to the subject's electrocardiogram signal and a sequence of images are obtained at equally spaced time points in the cardiac cycle. Typically, 20-32 time points are acquired. In this embodiment, two such image sequences are obtained: one proximal to the right PA (RPA) bifurcation and one distal to the bifurcation. Measurements could also be obtained from the left PA (LPA) proximal and distal to the bifurcation. The slices are prescribed perpendicular to the artery at each point, and velocity perpendicular to the slice is measured. As shown in FIG. 2B, the resulting images contain the blood velocity field in a cross section of the artery. A user defines the boundary of the artery with the aid of a computer in each image of the sequence. Statistics of the velocity field in the artery at each time point are computed to produce a velocity versus time curve over the cardiac cycle as shown in FIG. 3.

FIGS. 4A-4D illustrate the pulsatile velocity versus time curves measured in a right PA (RPA) at a point proximal to the bifurcation and a point distal to the bifurcation in a normal human volunteer and a patient with pulmonary hypertension (PH). In a normal volunteer, with a compliant PA, the velocity profile not only is shifted in the transit time between the two sites, but there are also complex shape changes across the entire wave. In a patient with PH, the PA is stiffer and both the time shift and shape change are reduced. These time shifts and shape changes are related to the compliance and geometry of the artery between the two points.

These changes can be compactly described by a transfer function between the two velocity profiles measured non-invasively with phase-contrast MRI. A transfer function is a linear or non-linear operator that generates an output waveform given an input waveform. In this embodiment, the transfer function, $s_V[\ ]$, is related to the input waveform, $V_{proximal}(t)$, and the output waveform, $v_{distal}(t)$, as follows:

$$v_{distal}(t) = s_V[v_{proxinial}(t)]$$

In some embodiments, the transfer function is modeled as a linear, time-invariant system. In this case, the transfer function convolves the input with an impulse response function, $S_V(t)$:

$$V_{distal}(t) = S_V(t) * v_{proximal}(t)$$

where * denotes the convolution operator. Taking the Fourier transform of both sides yields $$V_{distal}(f) = S_V(f) V_{proximal}(f)$$

where f is frequency in Hertz, and $S_V(f)$ is the transfer function. $S_V(f)$ is a complex-valued function and is often displayed as plots of the magnitude of $S_V(f)$ versus frequency and the phase of $S_V(f)$ versus frequency. In this embodiment, the velocity transfer function (VTF) can be computed from the measured input and output waveforms as follows:

$$S_V(f) = \frac{V_{distal}(f)}{V_{proximal}(f)}.$$

The transfer function above is a complex-valued function of continuous frequency. However, the transfer function is displayed as complex magnitude versus harmonic frequency. A harmonic frequency is an integer multiple of the cardiac frequency, which is equal to the reciprocal of the cardiac period. Expressing the transfer function in harmonics allows comparisons between subjects or in the same subject over time to be made independent of the individual heart rates.

In some embodiments, the transfer function is implemented in the time domain as an autoregressive moving average (ARMA) model:

$$Y_k = X_k + \sum_{i=1}^{p} b_i Y_{k-i} + \sum_{i=1}^{q} a_i X_{k-i}$$

where $X_k$ are samples of the input signal and $Y_k$ are samples of the output signal. p is number of moving average terms and q is the number of autoregressive terms. The $a_i$ and $b_i$ are coefficients. The parameters p, q, $a_i$, and $b_i$ are computed based on the measured input and output signals, and a function of these parameters is related to the material properties of the vessel.

Transfer functions like the VTF are one-way operators. They produce the output given the input but not necessarily the input given the output. In arteries, part of the blood pressure wave reflects off of the capillary bed and travels upstream through the artery. Sometimes this can be seen as the so-called dicrotic notch in velocity or pressure waveforms (for example, see FIG. 9C and 010 in FIG. 6). To investigate the effects of reflected waves on the VTF, simulations were performed of a velocity profile traveling through a section of PA with no change in shape or amplitude and a transit time of 25 ms. VTFs were computed from the input and output velocity profiles for the ideal case when no reflected wave was present and for the more realistic case when a reflected wave with an amplitude 10% of the primary wave and delayed by 500 ms was present. The reflected wave results in a ripple effect that averages out when parameters are computed over a range of harmonics.

Impedance is a specific case of a transfer function when the two functions are voltage and current or pressure and flow measured at the same point in the artery:

$$\text{Impedance}(f) = \frac{\text{Pressure}(f)}{\text{Flow}(f)}.$$

The VTF is like impedance because it describes predominantly the influence of vessel geometry and compliance/stiffness to cause frequency-dependent changes in the input velocity profile as it travels through the artery thereby producing the output velocity profile.

In some embodiments, a single harmonic magnitude in the VTF or a linear combination of harmonic magnitudes are calculated and used as a surrogate measure of arterial compliance.

In other embodiments, blood pressure waveform, with pressure as the y-axis and time as the x-axis, is measured directly with an invasive catheter at two points in the arterial tree. The time-varying blood pressure waveform at the upstream (proximal) point is considered the input and the blood pressure waveform at the downstream (distal) point is considered the output.

Figure 5:
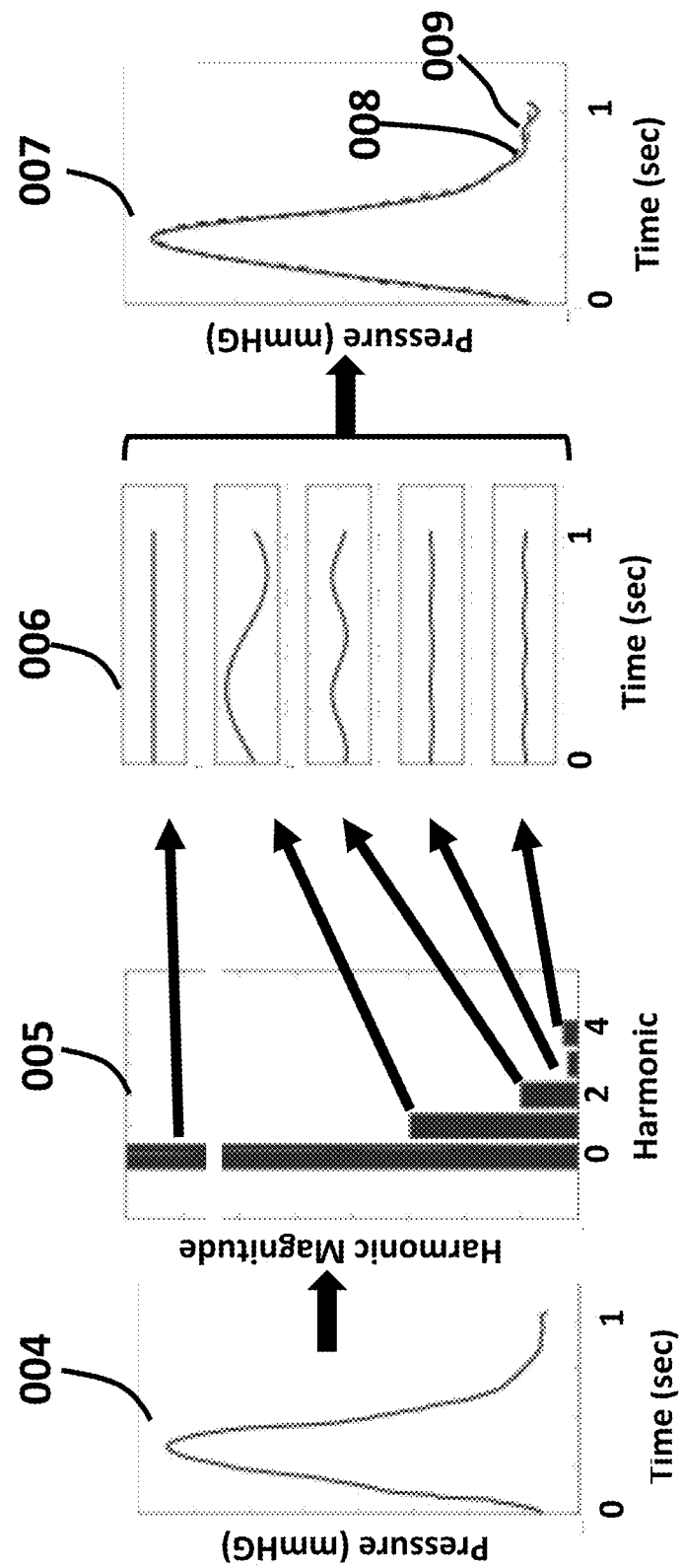
FIG. 5 illustrates the decomposition of a pressure waveform (004) into harmonic components, where the first 5 harmonic magnitudes are shown in 005, the first 5 harmonic component waveforms are shown in 006, the overlaying of the actual waveform (008, dashed line) on a waveform calculated from the first 5 harmonics (009, solid line) are shown in 007, where Harmonic 0 is the mean pressure, and higher order harmonics describe subtle changes in the waveform.
Figure 6:
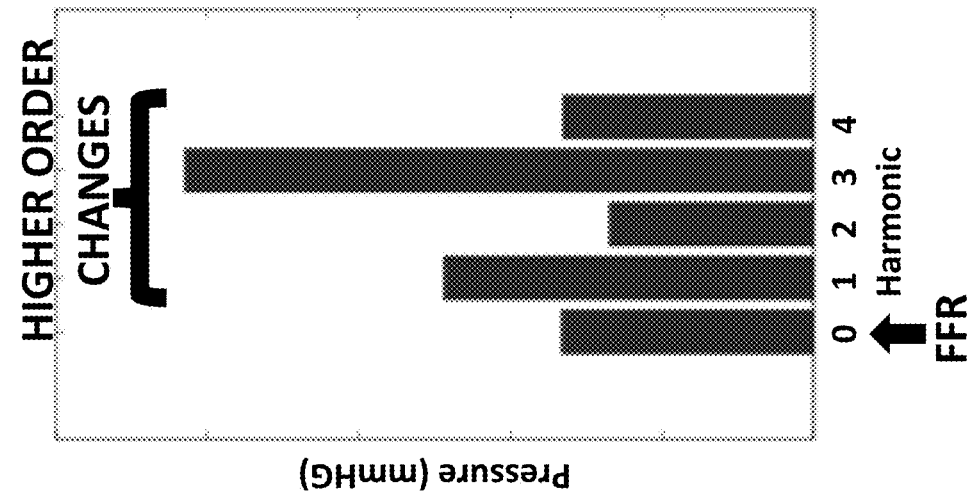
FIG. 6 illustrates the calculation of a pressure transfer function (PTF) from a proximal and distal pressure waveform, where each distal harmonic magnitude is divided by the corresponding proximal harmonic magnitude to form the corresponding PTF harmonic, Harmonic 0 corresponds to the FFR, higher order harmonics describe changes to the shape of the waveform as it passes through the section of artery, and 010 denotes the dicrotic notch.
Figure 6:
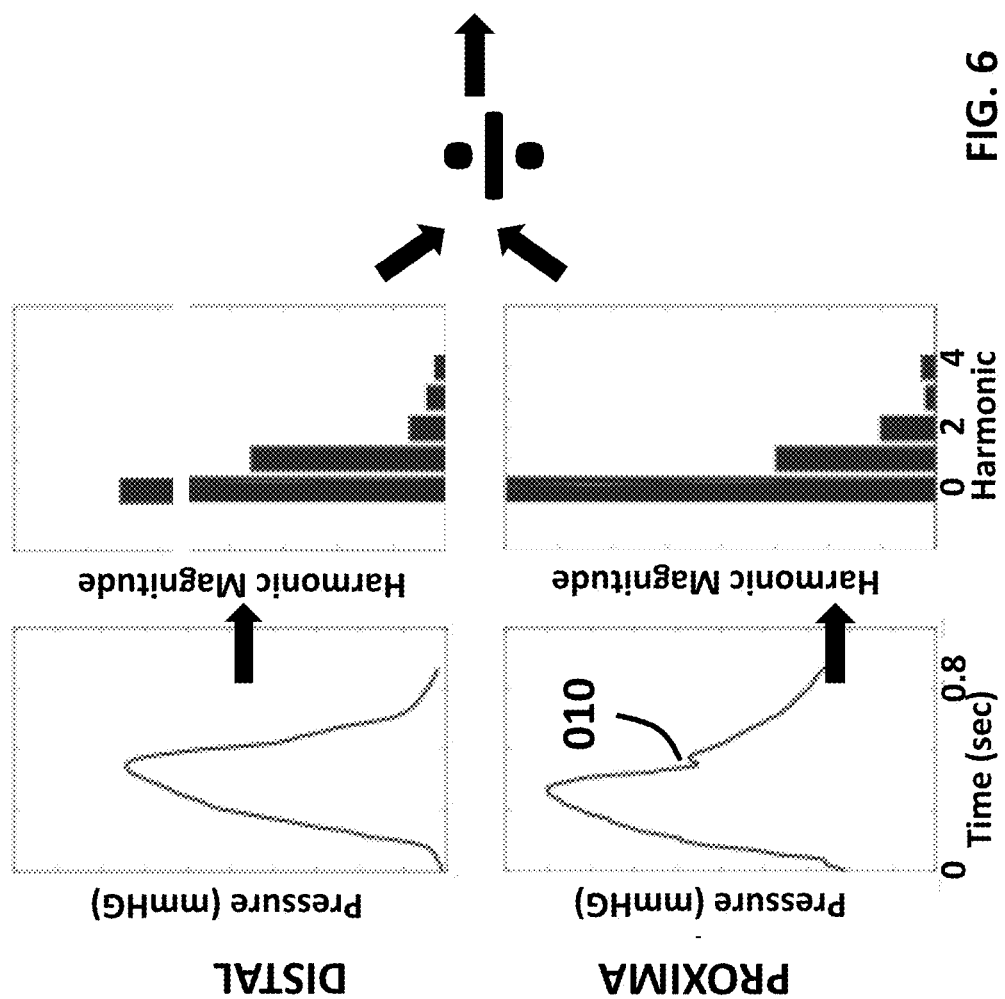
Figure 7A:
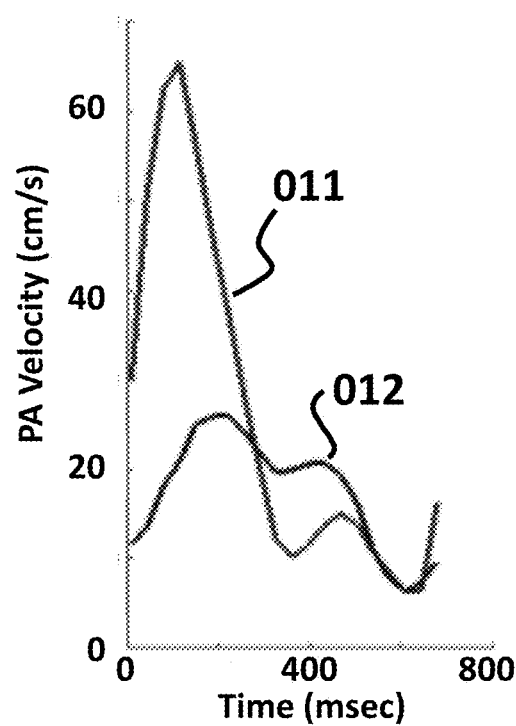
FIGS. 7A, 7B, 7C, and 7D show representative right PA velocity curves (FIG. 7A and FIG. 7C) and corresponding VTF (FIG. 7B and FIG. 7D) from a patient with PVR≤2.5 Woods Units (WU) (FIG. 7A and FIG. 7B) and a patient with PVR≥2.5 WU (FIG. 7C and FIG. 7D), where 011 and 012 respectively denote the proximal waveform and the distal waveform in FIG. 7A, and 013 and 014 respectively denotes the proximal waveform and the distal waveform in FIG. 7C.
Figure 7B:
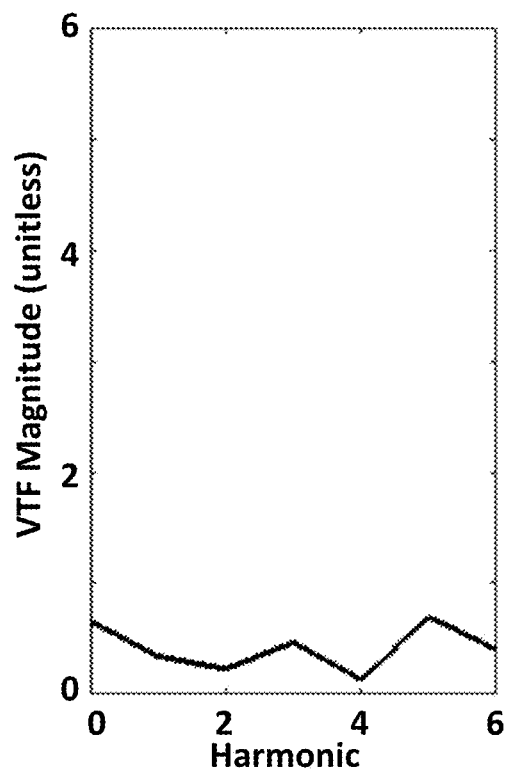
Figure 7C:
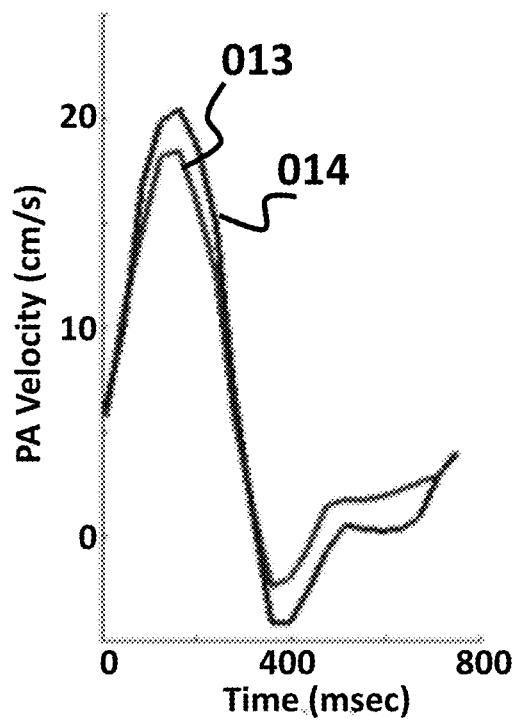
Figure 7D:
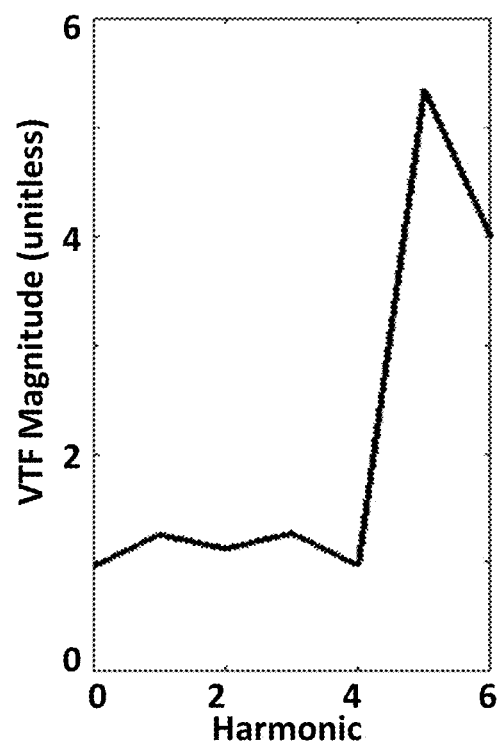

In this embodiment, as shown in FIG. 5 and FIG. 6, the pressure transfer function (PTF) $S_P(f)$ is computed between the two measured pressure profiles by taking the Fourier transform of each pressure profile and dividing one by other as follows:

$$S_P(f) = \frac{P_{distal}(f)}{P_{proximal}(f)}$$

FIG. 5 illustrates the decomposition of a pressure waveform (004) into harmonic components, where the first 5 harmonic magnitudes are shown in 005, the first 5 harmonic component waveforms are shown in 006, the overlaying of the actual waveform (008, dashed line) on a waveform calculated from the first 5 harmonics (009, solid line) are shown in 007. Harmonic 0 is the mean pressure. Higher order harmonics describe subtle changes in the waveform. FIG. 6 illustrates the calculation of a pressure transfer function (PTF) from a proximal and distal pressure waveform. Each distal harmonic magnitude is divided by the corresponding proximal harmonic magnitude to form the corresponding PTF harmonic. Harmonic 0 corresponds to the FFR. Higher order harmonics describe changes to the shape of the waveform as it passes through the section of artery.

In some embodiments, a single harmonic magnitude in the PTF or a linear combination of harmonic magnitudes are calculated and used as a surrogate measure of arterial compliance.

In some embodiments, a single heartbeat pressure waveform is measured with an invasive catheter at a point distal to a suspected stenosis in a coronary artery and considered to be a reference waveform. The catheter is then pulled back through the area of suspected stenosis yielding a series of single heartbeat waveforms. A series of PTFs $S_{P_i}(f)$ are then computed by computing $$S_{P_i}(f) = \frac{P_{distal_i}(f)}{P_{proximal}(f)}$$

In this embodiment, the entire series of pressure waveform is analyzed to obtain a comprehensive analysis of the pressure waves that reflects the fundamental interaction of moving blood in the coronary artery, and the vessel wall, coronary branches and stenosis. This embodiment not only allows evaluation of parameters analogous to FFR, but also parameters related to arterial material parameters.

In some embodiments, a single harmonic magnitude in the PTF or a linear combination of harmonic magnitudes are calculated. Changes in the harmonics or linear combination of harmonics are used to determine the location and severity of the stenosis.

Clinical Example 1

Patients with primary pulmonary hypertension (PH) (n=8), chronic obstructive pulmonary disease (COPD) Gold Stage I-III with no clinical evidence of PH (n=8) and normal controls (n=4) were studied. Each subject underwent PC-MM to obtain velocity profiles through a slice in the main pulmonary artery (MPA) and a slice through the right pulmonary artery (RPA) proximal to the bifurcation.

Figure 8:
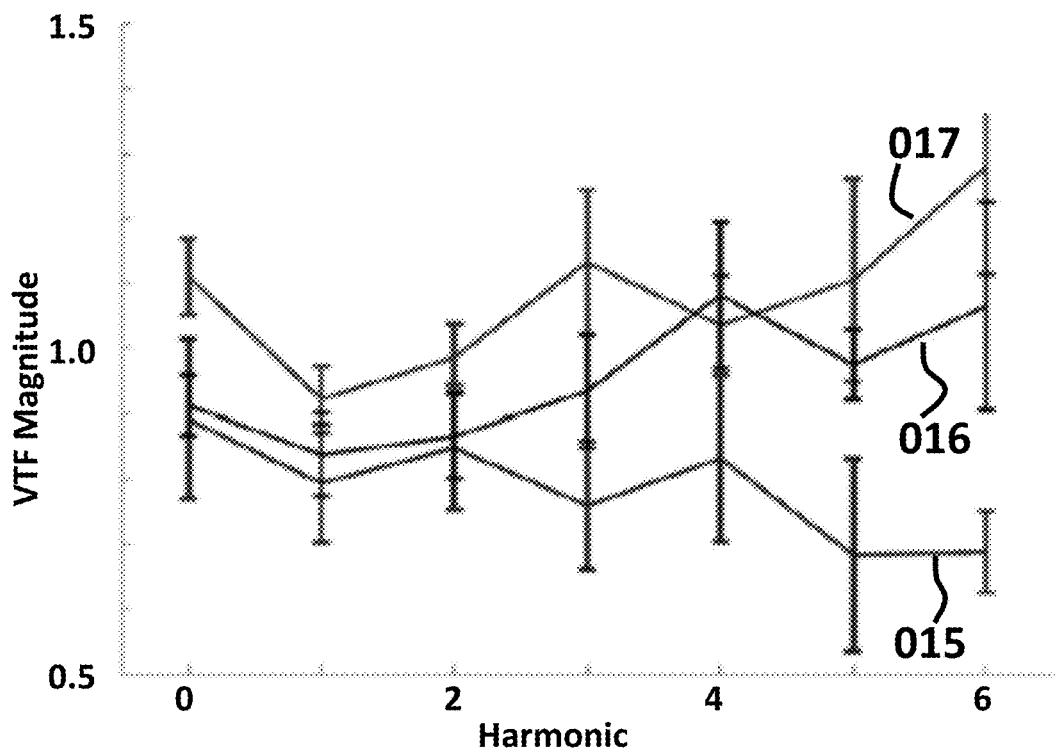
FIG. 8 shows the VTF magnitude versus harmonic for a group of PH patients (017, n=8), COPD patients (016, n=8) and normal volunteers (015, n=4). The VTF at zero harmonic is greater in PH than normals or COPD, which is consistent with high PVR values expected in PH. However, at higher harmonics the COPD group behaves similar to the PH group suggesting increased PA stiffness.

FIG. 8 shows the VTF magnitude versus harmonic for a group of PH patients (017, n=8), COPD patients (016, n=8) and normal volunteers (015, n=4). The VTF at zero harmonic is greater in PH than normals or COPD, which is consistent with high PVR values expected in PH. However, at higher harmonics the COPD group behaves similar to the PH group suggesting increased PA stiffness.

FIG. 8 shows the average VTF magnitude and phase computed from normal volunteers (normals, 015), patients with PH (017), and patients with COPD (016). These spectra are plotted versus harmonic number. As expected, in PH patients with much stiffer arteries, the magnitude spectrum is fairly constant and the phase is relatively linear over the first 6 harmonics (illustrated in 017). At zero harmonic, the magnitude of VTF is higher in the PH group compared to normals. It is interesting to note that at zero harmonic, the magnitude of VTF in COPD group is similar to normals but at higher harmonics magnitude in COPD patients behave like those with PH rather than like normals. Thus, at the zero harmonic that correlates with traditional PVR measurement, COPD patients in this pilot study would have considered to have normal PVR, PA pressures, and vessel stiffness. But with VTF analysis at higher harmonics, it was clear that it might not be the case for the vessel stiffness. Based on these results, the VTF is a promising method to detect vessel wall stiffness non-invasively earlier in time than traditional invasive measures of PA pressures or PVR. These preliminary results incorporating VTF are consistent with theoretical predictions of the stiff tube model (FIGS. 1A, 1B, 1C, and 1D, and FIGS. 4A, 4B, 4C, and 4D).

Figure 9A:
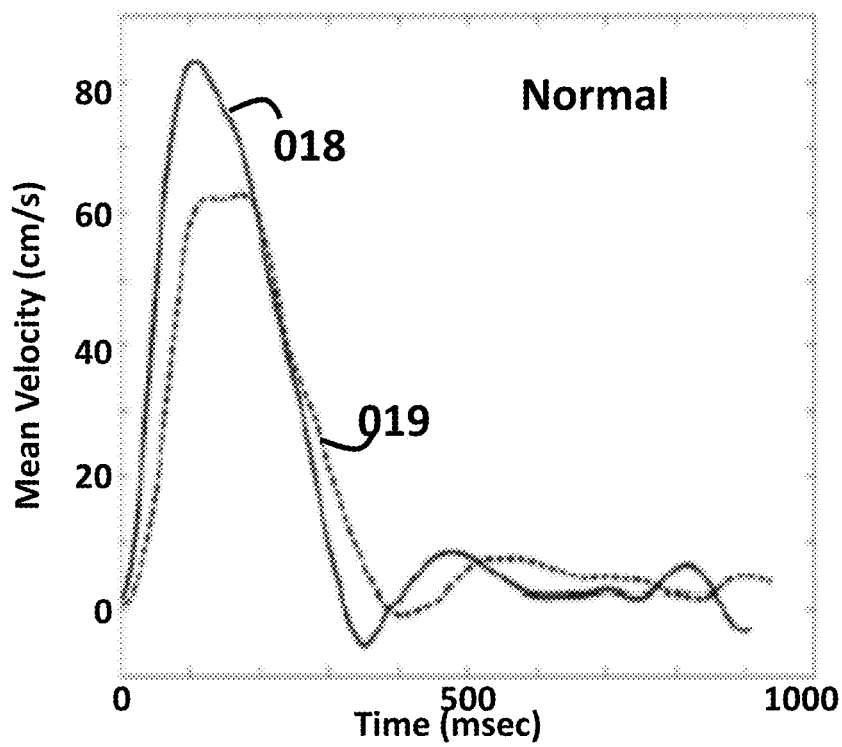
FIGS. 9A, 9B, and 9C show representative individual average velocity profiles at a point in the main pulmonary artery (018, 020, 022) and right pulmonary artery proximal to the bifurcation (019, 021, 023), and the difference in shift of velocity profiles in normal, COPD, and PH are respectively shown in FIG. 9A, FIG. 9B, and FIG. 9C.
Figure 9B:
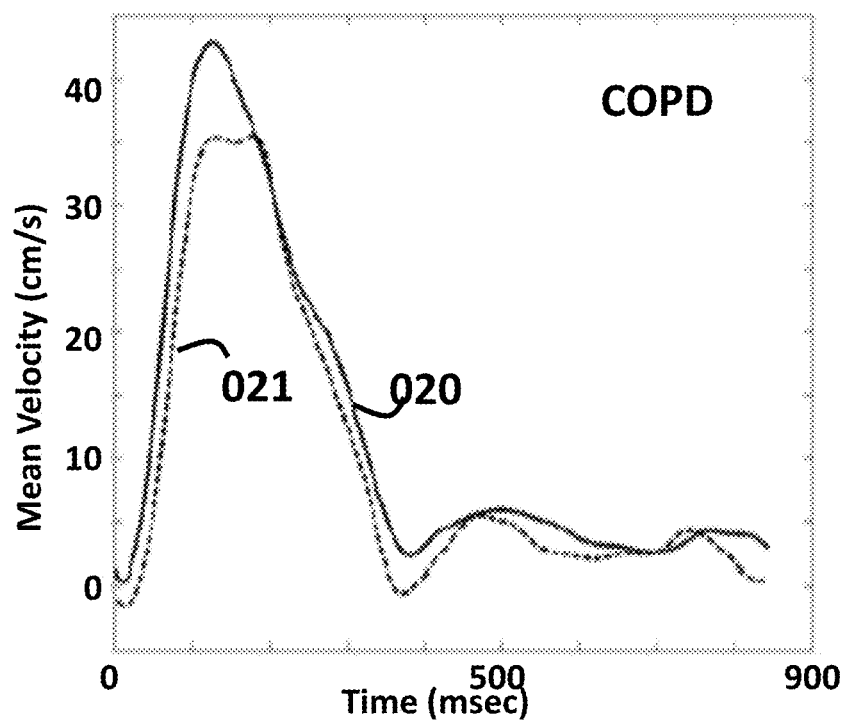
Figure 9C:
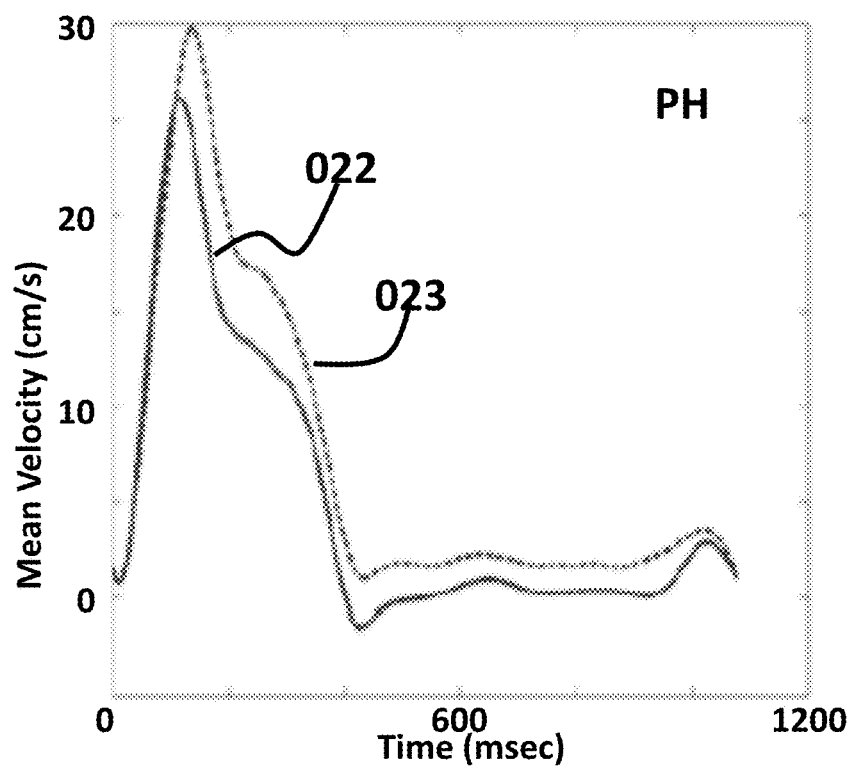
Figure 10:
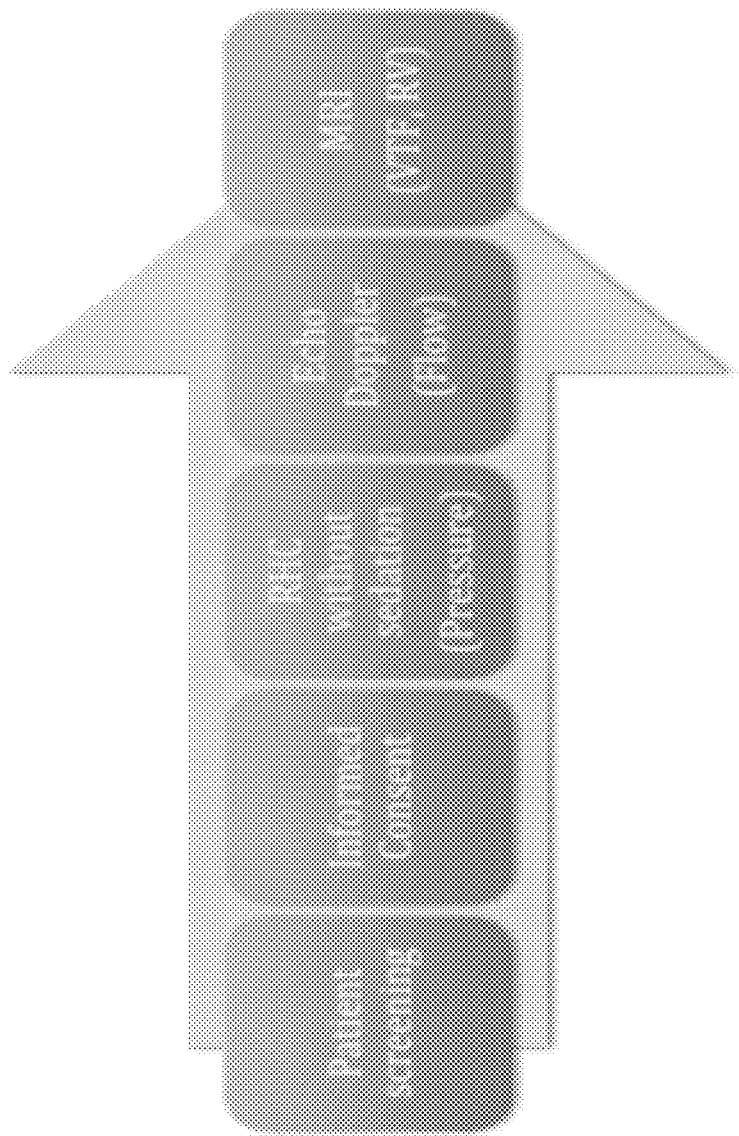
FIG. 10 illustrates the patient flow in Clinical Example 2.

Similar results can be seen in the individual velocity plots shown in FIGS. 9A, 9B, and 9C, where the RPA velocity is a time shifted and scaled version of the MPA velocity.

FIGS. 9A, 9B, and 9C show representative individual average velocity profiles at a point in the main pulmonary artery (018, 020, 022) and right pulmonary artery proximal to the bifurcation (019, 021, 023). Note the difference in shift of velocity profiles in normals (FIG. 9A) vs COPD (FIG. 9B) vs PH (FIG. 9C).

As shown in FIG. 9A, in normal subjects with compliant arteries, the RPA velocity profile (019) is broadened compared with the MPA velocity profile (018). FIG. 8 shows plots of average VTF magnitude versus harmonic for the three groups. In COPD (which were Gold Stage I-III with no clinical evidence of PH), the results of the VTF magnitude (016) were found to be intermediate between PH (017) and normals (015), indicating that the PA is stiffer than normals.

Clinical Example 2

In this study, it was hypothesized that a non-invasive PC-MRI derived VTF embodiment correlates with increased PA stiffness/resistance and therefore can provide non-invasive assessment of the pulmonary arterial circuit and RV-PA coupling, which is a condition where RV blood pumping function is impaired due to increased arterial stiffness. In this pilot study, patients who had undergone clinically indicated right heart catheterization (RHC) were prospectively evaluated with cardiac MM (CMR). The following specific aims were tested:

Specific Aim 1: To test the hypothesis that novel non-invasive CMR derived VTF, $S_V(f)$, correlates with the changes in PA stiffness/resistance as measured by invasive impedance.

Sub Aim 1: To test whether relationship is independent of elevation in pulmonary capillary wedge pressure (PCWP).

Sub Aim 2: To test intra- and inter-observer reliability of VTF measurement.

Specific Aim 2: To test the hypothesis that the VTF, $S_V(f)$, correlates with changes in RV structure and function.

Methods

Sample Population: Inclusion criteria: Patients who had undergone successful clinically indicated outpatient RHC at University of Alabama at Birmingham Hospital and The Kirklin Clinic and are willing to undergo CMR. Exclusion criteria: Patients were excluded from the study if they had any contraindication for CMR (MRI incompatible metal prosthesis, claustrophobia), are on inotropic therapy, ventricular assist device or have history of heart or lung transplantation.

A total of 104 patients were screened of which 39 were eligible to participate in the study. 26 patients consented to participate of which 6 patients unsuccessfully attempted CMR examination due to realization of claustrophobia that they were not aware of before. A total of 20 patients were thus enrolled (10 with PVR <2.5: Normal PVR group, 10 with PVR ≥2.5: High PVR group). Of these 20 patients, 1 patient had invasive impedance and CMR VTF measured by phase contrast sequences but could not complete the cine steady state free precession sequence for RV mass, volume and function assessment due to an unexpected technical problem with MRI scanner.

Patient Flow: Eligible patients who consented for the study underwent clinically indicated RHC. PA pressure measurements were obtained using Swan-Ganz PA catheter in the MPA. For flow measurement, blood flow velocity profile was obtained using transthoracic pulmonary arterial pulsed wave Doppler in MPA during or around the time of RHC. The analysis of these two measurements (as detailed below) resulted in calculation of invasive impedance. They then underwent same day CMR examination including PC sequences for VTF, RV structure and function analysis. The patient flow can be visualized in FIG. 10. The study was approved by University of Alabama at Birmingham Institutional Review Board.

Figure 11A:
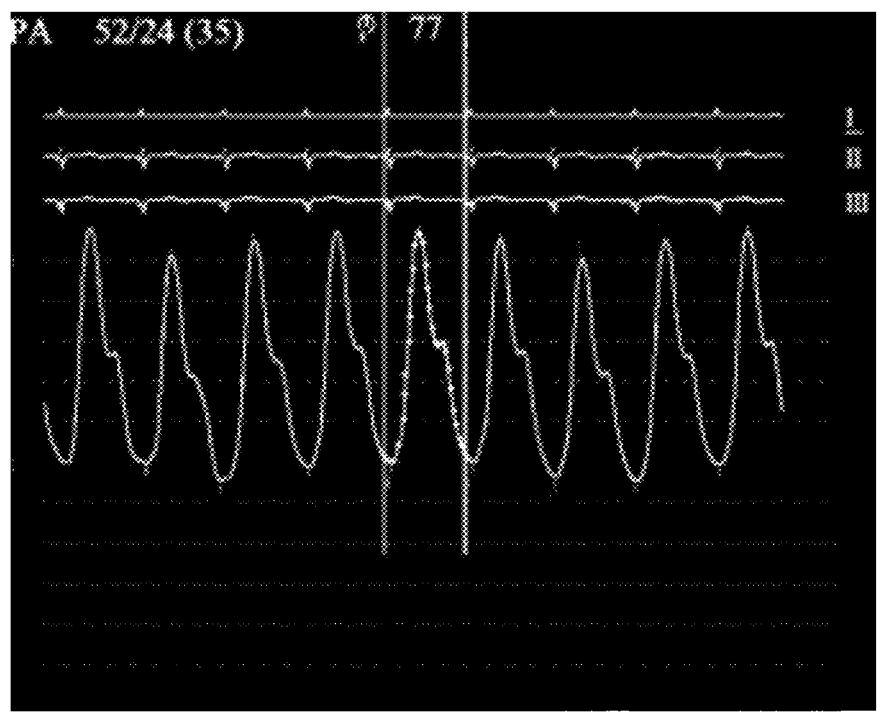
FIGS. 11A and 11B show digitization of main pulmonary artery pressure waveform in one cardiac cycle (FIG. 11A) and digitization of main pulmonary artery pulsed wave Doppler waveform in one cardiac cycle (FIG. 11B)
Figure 11B:
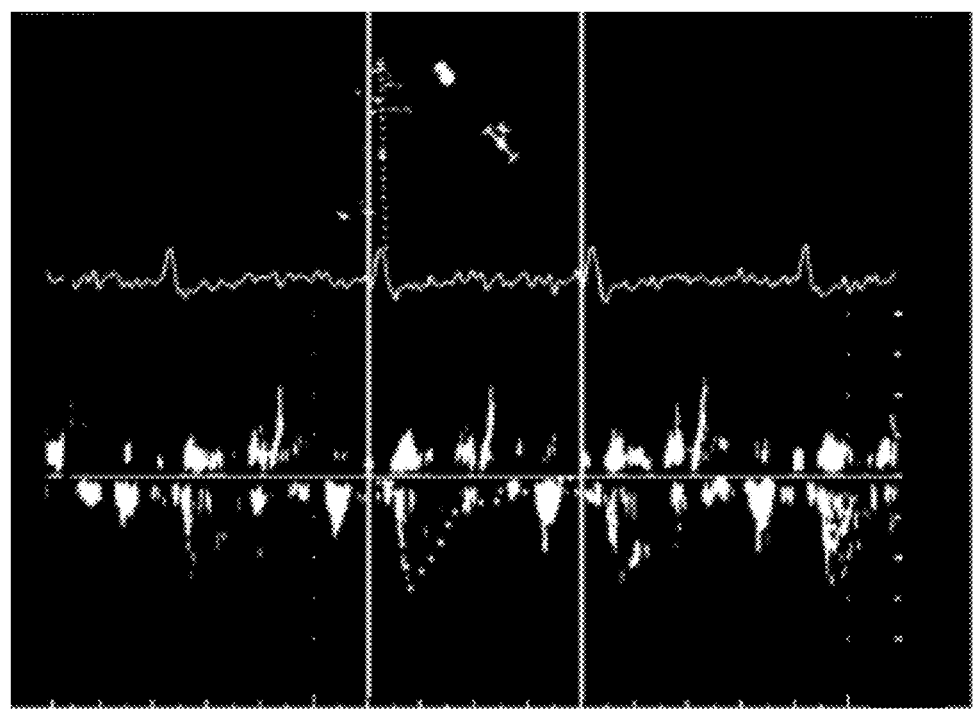

RHC, Doppler Echocardiography And Invasive Impedance Measurement: MPA pressure obtained from invasive RHC and MPA blood flow velocity profiles obtained from pulsed wave Doppler were synchronized using electrocardiogram artifact. These waveforms were then digitized using WebPlotDigitizer version 3.8 as shown in FIGS. 11A and 11B.

The digital data was extracted as comma separated values format. The velocity profile was converted to flow profile using the correction factor (Hunter, K. S., et al., Pulmonary vascular input impedance is a combined measure of pulmonary vascular resistance and stiffness and predicts clinical outcomes better than pulmonary vascular resistance alone in pediatric patients with pulmonary hypertension. *Am Heart J*, 2008. 155(1): p. 166-74.)

$$Q(t) = A_{corr} V(t)$$

$$A_{corr} CO V_{mean}$$

where, $Q(t)$ is the calculated flow-time history, $V(t)$ is the velocity-time history obtained from digitized pulsed wave Doppler waveform, $A_{corr}$ is the correction factor applied to convert velocity-time to flow-time, CO is cardiac output obtained from right heart catheterization, $V_{mean}$ is the mean velocity computed from the midline velocity-time history. Impedance was then calculated by obtaining discrete Fourier transformation on the digitized data using Matlab version 2015a.

RHC protocol: After informed consent, patients underwent clinically indicated right heart catheterization with 5 F Swan-Ganz fluid filled catheter via right internal jugular vein under local anesthesia only without intravenous sedation.

Transthoracic Doppler echocardiography protocol: With patient in left lateral decubitus position and transducer in left parasternal intercostal space (usually 3rd or 4th), short axis view of heart was obtained at the level of the aortic valve. Pulsed-wave Doppler echocardiography was then obtained in this view with 2 mm sample volume placed 0.5-1 cm distal to pulmonic valve in the main pulmonary artery. Doppler echocardiography was obtained using Philips IE33 ultrasound system.

Figure 12:
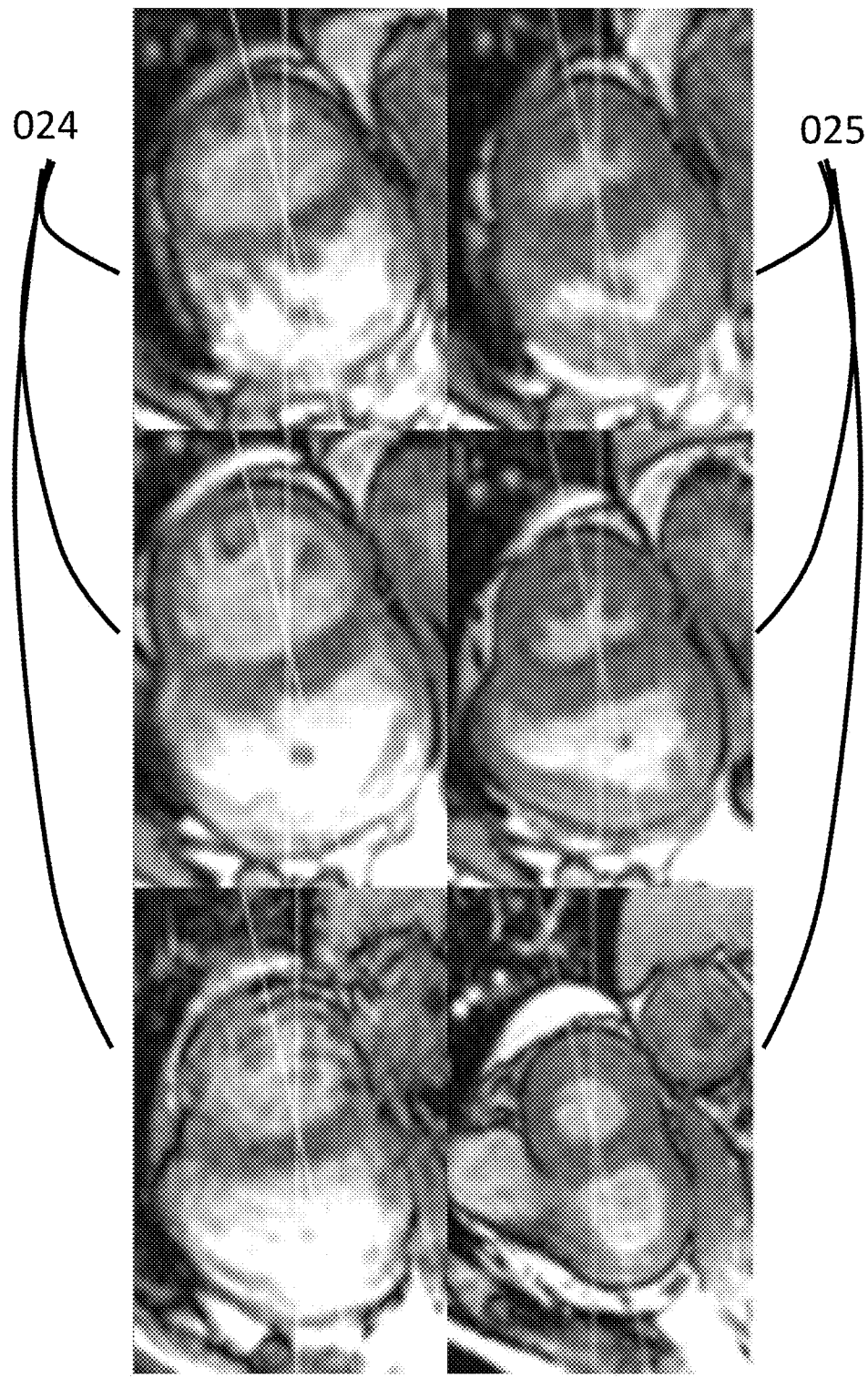
FIG. 12 illustrates right ventricular diastolic (024) and systolic (025) frames obtained from cine-cardiac magnetic resonance imaging. The green lines denote intersection with 4-chamber and left ventricular outflow tract slices.

CMR Imaging and Velocity Transfer Function Measurement: Comprehensive CMR consisting of cine and phase contrast sequences was performed on the same day of pressure-flow measurements to maintain the close temporal relationship and to minimize significant alteration in hemodynamic state. It included assessment of flow in the MPA, proximal (to the bifurcation) RPA, distal RPA, and proximal LPA using a PC-CMR technique (FIGS. 2A and 2B). Mean velocity-time profile over a cardiac cycle (FIG. 3) and accurate assessment of RV mass, volumes and function (FIG. 12) were obtained.

MRI Protocol: Magnetic resonance imaging was performed on a 1.5-T magnetic resonance scanner (GE Signa, Milwaukee, Wis.) optimized for cardiac application. Cine SSFP: Electrocardiographically (ECG)-gated breath-hold steady-state free-precision technique was used to obtain standard 2-chamber, 4-chamber and short-axis views with following general parameters: prospective ECG gating, slice thickness =8 mm, 2 mm interslice gap, field of view=40×40 cm, scan matrix=224×128, flip angle=45°, repetition/echo times=3.8/1.6 ms. Twenty cardiac phases were reconstructed with 8 views per segment.

A short-axis stack was positioned from an end-diastolic 4-chamber image, centered parallel to the mitral annulus and perpendicular to the septum, starting 1 cm proximal to the mitral valve to 1 cm beyond the apex. Analysis was performed using CAAS MRV 3.4 (Pie Medical Imaging, Netherland). Phase-contrast MM: It was performed using ECG gated, breath-hold fast gradient recalled echo phase contrast sequence (Fast 2D Phase contrast). Typical parameters were: field of view=40 cm, scan matrix=256×128, encoding velocity 150 cm/s, NEX=1, flip angle=15°, repetition/echo times=7.6/3.1 ms, band width+/−31.25 KHz, views per segment 8. 20 phases were reconstructed. Contours were drawn using CAAS MR Flow ver 1.2 (Pie Medical Imaging, Netherland) and exported as .csv format for analysis using MATLAB 2015a.

In addition to VTF and invasive input impedance, the traditional pulmonary artery stiffness parameters in Table 1 were also studied.

TABLE 1

Pulmonary artery stiffness parameters.

| Parameters | Definition | Formula | Units | Technique |
|---|---|---|---|---|
| VTF ($S_F(f)$) | Transfer function of velocity at MPA as input and RPA or LPA as output. | $V_{RPA}(f)/V_{MPA}(f)$ | unitless rad | MRI |
| Input Impedance ($Z_i$) | Ratio of pulsatile pressure to pulsatile flow at input of an arterial site | P/Q | mmHg/ (L/min) rad | RHC + Doppler |
| Impedance Modulus (Z) | Ratio of modulus of pressure and flow | \|P\|/\|Q\| | mmHg/ (L/min) | RHC + Doppler |
| Impedance Phase (θ) | Fraction of wave cycle that has elapsed relative to each other | β-(φ) | rad | RHC + Doppler |
| PVR | Static resistance | $(P_2 - P_1)/Q$ | Woods Units | RHC |
| PA-Ao Diameter Ratio | Ratio of pulmonary artery to aortic root diameter | PA diameter/ Aortic root diameter | unitless | MRI |
| Capacitance | Volume change per unit pressure | SV/PP | cm³/mmHg | RHC |
| Pulsatility | Relative area change of MPA | [(maxA − minA)/minA] × 100 | % | MRI |

TABLE 1-continued

Pulmonary artery stiffness parameters.

| Parameters | Definition | Formula | Units | Technique |
|---|---|---|---|---|
| Compliance | Area change per unit pressure | (maxA − minA)/PP | $mm^2/mmHg$ | MRI + RHC |
| Distensibility | Relative area change per unit pressure | [(maxA − minA)/minA × PP] × 100 | %/mmHg | MRI + RHC |
| Elastic Modulus | Driving pressure effecting a unit relative area change | (PP × minA)/(maxA − minA) | mmHg | MRI + RHC |
| Stiffness Index | Slope of function between distending arterial pressure and arterial distention | [ln(PASP/PADP)]/[(maxA − minA)/minA] | unitless | MRI + RHC |

A: area,
Ao: aortic root,
MPA: main pulmonary artery,
MRI: magnetic resonance imaging,
P: pressure,
PA: pulmonary artery,
PASP: pulmonary artery systolic pressure,
PADP: pulmonary artery diastolic pressure,
PP: pulse pressure,
Q: flow,
RHC: right heart catheterization,
RPA: right pulmonary artery,
VTF: velocity transfer function,
VRPA(f): velocity function at RPA,
VMPA(f): Velocity function at MPA.

Demographics, clinical and imaging characteristics of normal and high PVR groups were compared using t-test or Wilcoxon test (if non-normal data) for continuous variables and Fisher's exact test for categorical variables. Repeated mixed-model analysis using the SAS MIXED procedure was performed on zero and first six harmonics of both invasive impedance as dependent variable and VTF as predictor variable to assess association of VTF with invasive impedance (Model: Invasive impedance=Mill Harmonics MRI*Harmonics). Unstructured covariance structure for the error term was fitted to accommodate correlation between various harmonics from the same subject. Averages of the zero and first harmonics for invasive impedance and averages of the fifth and sixth harmonic for VTF were computed. Mean high frequency magnitude, MHFM, was defined as average magnitudes of 5th and 6th harmonics of VTF. Average impedance and MHFM curves were then studied for correlation. All studies were evaluated by cardiologists: AG, twice, and HG once, in an independent and blinded fashion for calculation of VTF. Intra-class correlation was used to investigate intra- and inter-observer reliability in calculation of VTF. Intra-class correlation coefficient was calculated using a SAS macro. Linear regression model was used to study association of RV mass, volume and function parameters with MHFM. Logistic model was used to obtain Receiver Operative Characteristic (ROC) curve to study performance of MHFM in differentiating patients with high or normal PVR. A $p<0.05$ was considered statistically significant. No adjustment of p-value was done for multiple statistical tests due to being a pilot study. All statistical analyses were performed using SAS version 9.4.

Results

Patients' Clinical And Imaging Characteristics: The study population comprised of middle-aged predominantly Caucasian individuals with typical comorbidities as outlined in Table 2.

TABLE 2

Demographics and clinical characteristics.

| Clinical Characteristics | All (n = 20) | Normal PVR Group, PVR <2.5 (n = 10) | High PVR Group, PVR ≥2.5 (n = 10) |
|---|---|---|---|
| Age, years | 55.25 ± 18.6 | 50.6 ± 21.17 | 59.9 ± 15.3 |
| Sex, females | 14 | 9 | 5 |
| Race | | | |
| Black | 3 | 2 | 1 |
| White | 17 | 8 | 9 |
| Body mass index, $kg/m^2$ | 27.55 ± 6.9 | 28.22 ± 7.47 | 26.88 ± 6.56 |
| Obesity | 7 | 4 | 3 |
| Smoking | | | |
| Never | 11 | 7 | 4 |
| Past | 9 | 3 | 6 |
| Current | 0 | 0 | 0 |
| Diabetes | 2 | 2 | 0 |
| Hypertension | 9 | 5 | 4 |

TABLE 2-continued

Demographics and clinical characteristics.

| Clinical Characteristics | All (n = 20) | Normal PVR Group, PVR <2.5 (n = 10) | High PVR Group, PVR ≥2.5 (n = 10) |
|---|---|---|---|
| Dyslipidemia | 11 | 5 | 6 |
| Coronary artery disease | 3 | 2 | 1 |
| Congestive heart failure | 4 | 2 | 2 |
| COPD | 1 | 1 | 0 |
| Interstitial lung disease | 4 | 1 | 3 |
| Obstructive sleep apnea | 4 | 2 | 2 |
| New York Heart Association Class | | | |
| 1 | 2 | 2 | 0 |
| 2 | 10 | 4 | 6 |
| 3 | 8 | 4 | 4 |
| Chronic kidney disease (eGFR <60) | 5 | 3 | 2 |
| PVR, Woods Units | 3.43 ± 2.86 | 1.34 ± 0.59 | 5.51 ± 2.7 |
| Medications | | | |
| Oral nitrates | 2 | 1 | 1 |
| Phosphodiesterase inhibitors | 7 | 2 | 5 |
| Endothelin receptor antagonists | 3 | 1 | 2 |
| Prostacyclin analogues | 2 | 0 | 2 |
| Calcium channel blockers | 6 | 4 | 2 |
| Beta-blockers | 7 | 5 | 2 |
| ACEI/ARB | 3 | 2 | 1 |
| Aldosterone antagonists | 6 | 3 | 3 |

Continuous variables are in mean ± SD, discrete variables are in number of individuals,
*p-value <0.05 for normal vs high PVR groups.
ACEI: angiotensin converting enzyme inhibitors;
ARB: angiotensin receptor blockers;
COPD: chronic obstructive pulmonary disease;
eGFR: estimated glomerular filtration rate, ml/min;
PAP: pulmonary artery pressure;
PCWP: pulmonary capillary wedge pressure;
PH: pulmonary hypertension;
PVR: pulmonary vascular resistance.

Figure 13:
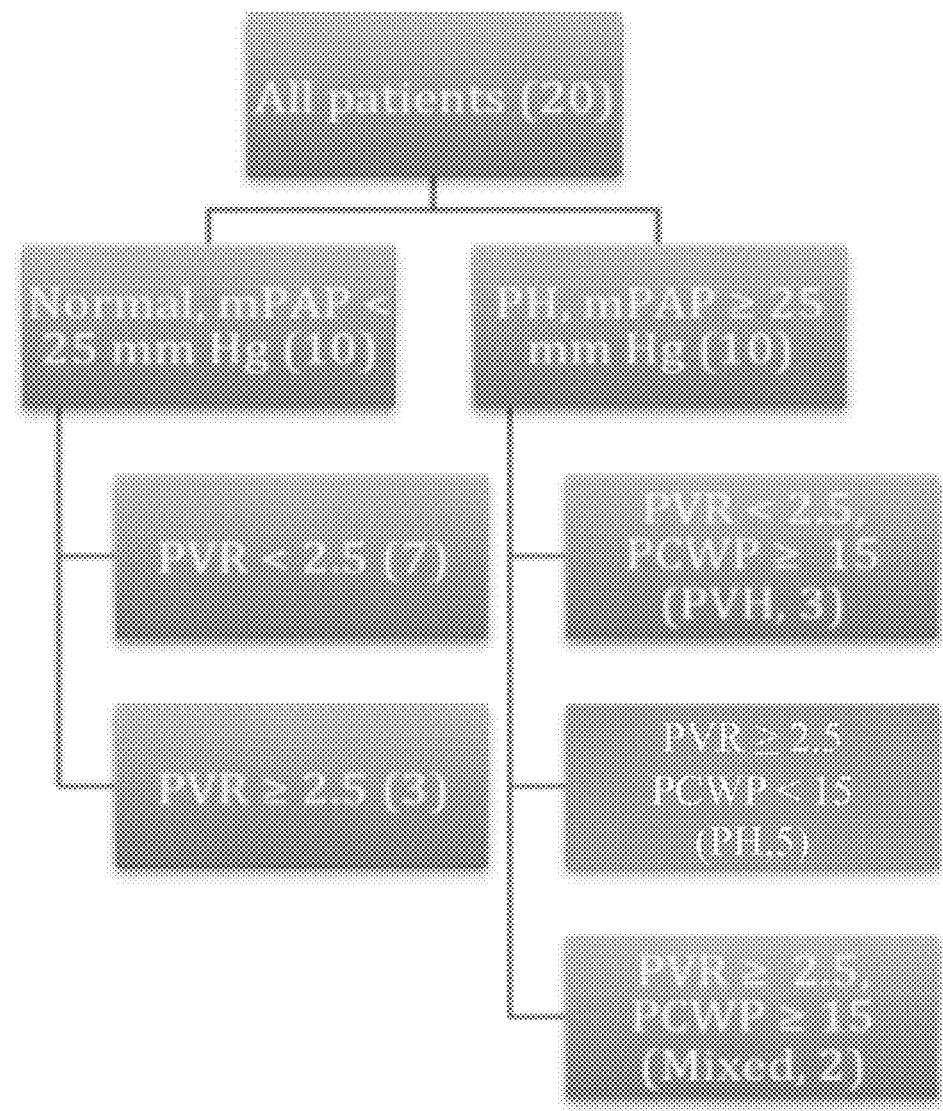
FIG. 13 illustrates the patient distribution for Clinical example 2 based on pulmonary pressures and/or resistance, where mPAP is the mean pulmonary artery pressure, PCWP the pulmonary capillary wedge pressure, PH pulmonary hypertension, PVH pulmonary venous hypertension, and PVR pulmonary vascular resistance.

Of the 20 patients, 10 patients had normal PA pressures as defined by mean PA pressure <25 mm Hg (FIG. 13). PVR of these 10 patients with normal mean PA pressure was 1.76±0.78 (mean±SD) Woods Units (WU). 1 SD above the mean PVR was approximately 2.5 WU. Also, clinically the detection of early PA remodeling (PVR between 2.5 and 3) is of interest. Therefore, study patients were divided into two groups—a Normal PVR group (10 patients) with PVR <2.5 WU and a High PVR group (10 patients) with PVR ≥2.5.

RHC and Doppler as well as RHC and MRI data were acquired closely in time (time difference: 0.029±0.04 hours, 2.38±1.15 hours respectively), Table 3. Bland-Altman analysis revealed excellent correlation and agreement between inter-modality heart rate, blood pressure and cardiac indices, as shown in Table 3.

TABLE 3

Inter-modality time, heart rate, blood pressure and cardiac index differences.

| Parameter | Correlation | | Agreement | |
|---|---|---|---|---|
| | Pearson r | p-value | Relative bias ± SD | p-value (mean vs bias) |
| Time difference, hours | | | | |
| RHC-Doppler | — | — | 0.029 ± 0.04 | — |
| RHC-MRI | — | — | 2.38 ± 1.15 | — |
| Heart rate, bpm | | | | |
| RHC-Doppler | 0.81 | <0.0001 | 4.15 ± 4.92 | 0.68 |
| RHC-MRI | 0.75 | 0.0002 | 6.3 ± 4.16 | 0.93 |
| BP, mmHg, RHC-MRI | | | | |
| SBP | 0.76 | 0.0002 | 11.83 ± 9.94 | 0.67 |
| DBP | 0.49 | 0.04 | 11.89 ± 9.8 | 0.46 |
| MBP | 0.65 | 0.004 | 10.5 ± 9.02 | 0.49 |
| CI, L/min/m$^2$, RHC-MRI | 0.69 | 0.0008 | 0.52 ± 0.37 | 0.74 |

Time differences are in median ± interquartile range.
HR and BP differences are in mean ± SD.
BP: blood pressure,
CI: cardiac index;
DBP: diastolic blood pressure,
MBP: mean blood pressure,
MRI: magnetic resonance imaging,
PA: pulmonary artery,
PVR: pulmonary vascular resistance,
RHC: right heart catheterization,
SBP: systolic blood pressure.

Invasive hemodynamic assessment using RHC revealed higher PA systolic, diastolic, mean, pulse pressures and lower cardiac indices in high PVR group compared to normal PVR group as shown in Table 4.

TABLE 4

Invasive hemodynamics.

| Hemodynamic parameter | All (n = 20) | Normal PVR Group, PVR <2.5 (n = 10) | High PVR Group, PVR ≥2.5 (n = 10) |
|---|---|---|---|
| Right atrial mean pressure | 6.6 ± 4.5 | 5.6 ± 2.7 | 7.5 ± 5.8 |
| Pulmonary artery systolic pressure | 44.9 ± 22.3 | 30.9 ± 9.6 | 59 ± 22.7* |
| Pulmonary artery diastolic pressure | 17 ± 9.3 | 12 ± 5.9 | 22 ± 9.5* |
| Pulmonary artery mean pressure | 29.5 ± 13.6 | 21 ± 6.8 | 37.9 ± 13.7* |
| Pulmonary artery pulse pressure | 27.9 ± 15.1 | 18.9 ± 6.6 | 37 ± 15.9* |
| Pulmonary capillary wedge pressure | 12.3 ± 6.6 | 12.7 ± 6.9 | 11.9 ± 6.6 |
| Thermodilution cardiac index, L/min | 3.01 ± 0.7 | 3.32 ± 0.6 | 2.7 ± 0.7* |
| Fick cardiac index, L/min | 3.02 ± 0.8 | 3.42 ± 0.8 | 2.62 ± 0.6* |
| Pulmonary vascular resistance, Woods Units | 3.43 ± 2.9 | 1.34 ± 0.6 | 5.51 ± 2.7* |
| Systemic vascular resistance, dynes · s/cm$^5$ | 1449.1 ± 461.6 | 1257.8 ± 333.3 | 1640.3 ± 507.4 |

All pressures are in mm Hg,
all values mean ± SD,
*p-value < 0.05 for normal PVR vs high PVR groups;
PVR: pulmonary vascular resitance CMR derived right ventricular mass index, end-diastolic volume index and mass to volume ratio were higher in high PVR group compared to normal PVR group, as shown in the table below. Left ventricular ejection fraction was, on average, preserved in both groups, as shown in Table 5.

TABLE 5

Right and left ventricular mass, volume and function.

| MRI parameter | All (n = 19) | Normal PVR Group, PVR <2.5 (n = 9) | High PVR Group, PVR ≥2.5 (n = 10) |
|---|---|---|---|
| Right ventricular ejection fraction, % | 52 ± 12 | 57 ± 13 | 48 ± 11 |
| Right ventricular stroke volume index, ml | 37 ± 11 | 36 ± 12 | 38 ± 12 |
| Right ventricular end-diastolic volume index, ml/m$^2$ | 73 ± 21 | 64 ± 12 | 81 ± 25 |
| Right ventricular mass index, g/m$^2$ | 24 ± 12 | 17 ± 5 | 30 ± 14* |
| Right ventricular mass/volume ratio | 0.3 ± 0.1 | 0.3 ± 0.1 | 0.4 ± 0.1* |
| Left ventricular ejection fraction, % | 60 ± 15 | 61 ± 19 | 59 ± 12 |
| Left ventricular stroke volume index, ml | 38 ± 10 | 42 ± 11 | 35 ± 7 |
| Left ventricular end-diastolic volume index, ml/m$^2$ | 68 ± 24 | 75 ± 29 | 61 ± 18 |
| Left ventricular mass index, g/m$^2$ | 57 ± 18 | 58 ± 19 | 55 ± 18 |

All values mean ± SD,
*p-value < 0.05 for normal PVR vs high PVR groups.
MRI: magnetic resonance imaging;
PVR: pulmonary vascular resistance Several other traditional measures of PA stiffness were studied. Compliance, capacitance, distensibility of PA were lower and elastic modulus was higher in high PVR group compared to low PVR group, as shown in Table 6.

TABLE 6

Measures of pulmonary arterial stiffness.

| Pulmonary artery stiffness parameter | All (n = 20) | Normal PVR Group, PVR <2.5 (n = 10) | High PVR Group, PVR ≥2.5 (n = 10) |
|---|---|---|---|
| Pulmonary to aortic diameter ratio | 0.94 ± 0.2 | 0.87 ± 0.2 | 1 ± 0.2 |
| Pulsatility, % | 21.7 ± 11.6 | 26.2 ± 14.3 | 17.3 ± 6.1 |
| Compliance, mm$^2$/mmHg | 5.9 ± 3.4 | 7.7 ± 3.5 | 4.2 ± 2.2* |
| Capacitance, cm$^3$/mmHg | 3.5 ± 2.1 | 4.7 ± 1.9 | 2.3 ± 1.4* |
| Distensibility, %/mmHg | 1.1 ± 0.9 | 1.5 ± 1.1 | 0.6 ± 0.3* |
| Elastic modulus, mmHg | 155.8 ± 93.5 | 94.5 ± 54.4 | 217.1 ± 84.5* |
| Stiffness index | 5.8 ± 3.9 | 4.9 ± 2.6 | 6.8 ± 4.7 |

All values mean ± SD,
*p-value < 0.05 for normal PVR vs high PVR groups.
PA: pulmonary artery,
PVR: pulmonary vascular resistance.

Velocity Transfer Function and Invasive Impedance: Mixed model statistical analysis with invasive impedance as outcome variable and VTF and harmonics as predictor variables was conducted. As all harmonics were included in the model, there were multiple observations per patient and, hence, unstructured covariance structure was utilized in the model. There was significant relationship between VTF and invasive impedance for right-sided VTF (proximal RPA to distal RPA, F-ratio 12.34, p-value 0.0023) but not for left sided VTF (MPA to proximal LPA, F-ratio 1.6, p-value 0.22). This relationship between VTF, right and invasive impedance remained significant after adjustment for elevation in PCWP (F ratio=8.08, p=0.01).

Figure 14A:
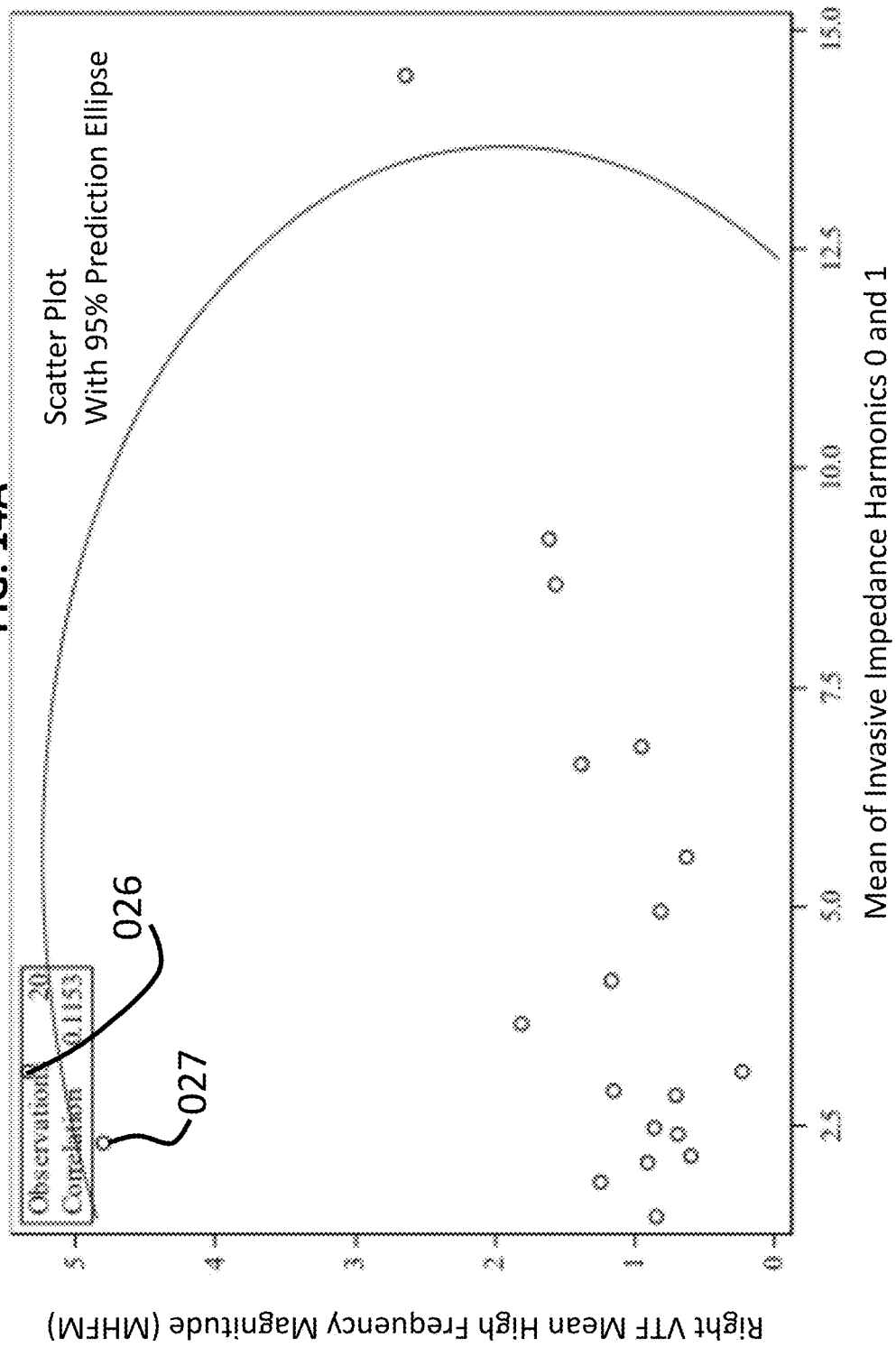
Figure 15:
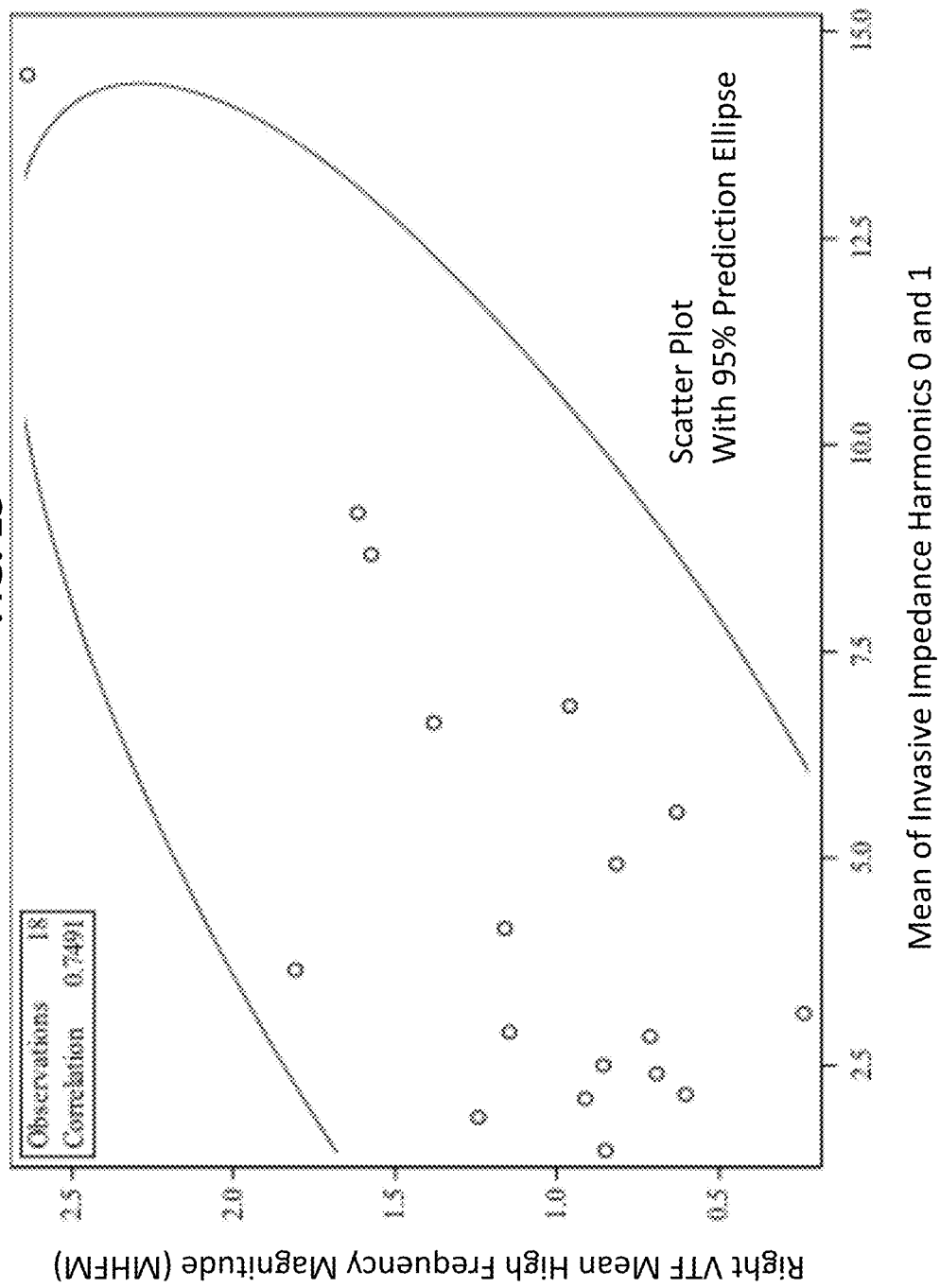
FIG. 15 shows a scatter plot of mean invasive impedance harmonics 0-1 and VTF MHFM in the RPA after removal of two 'outliers'.
Figure 16C:
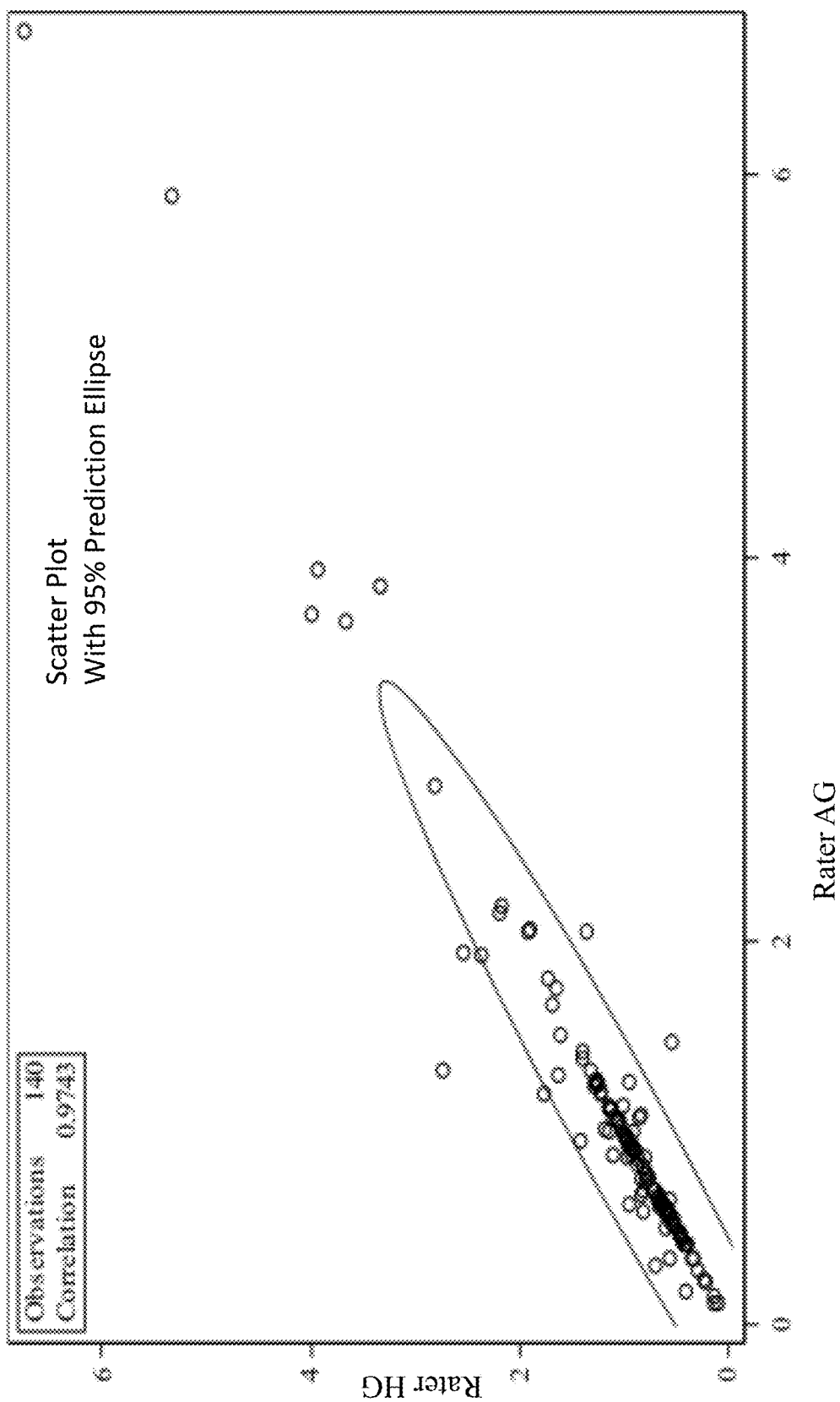
Figure 16D:
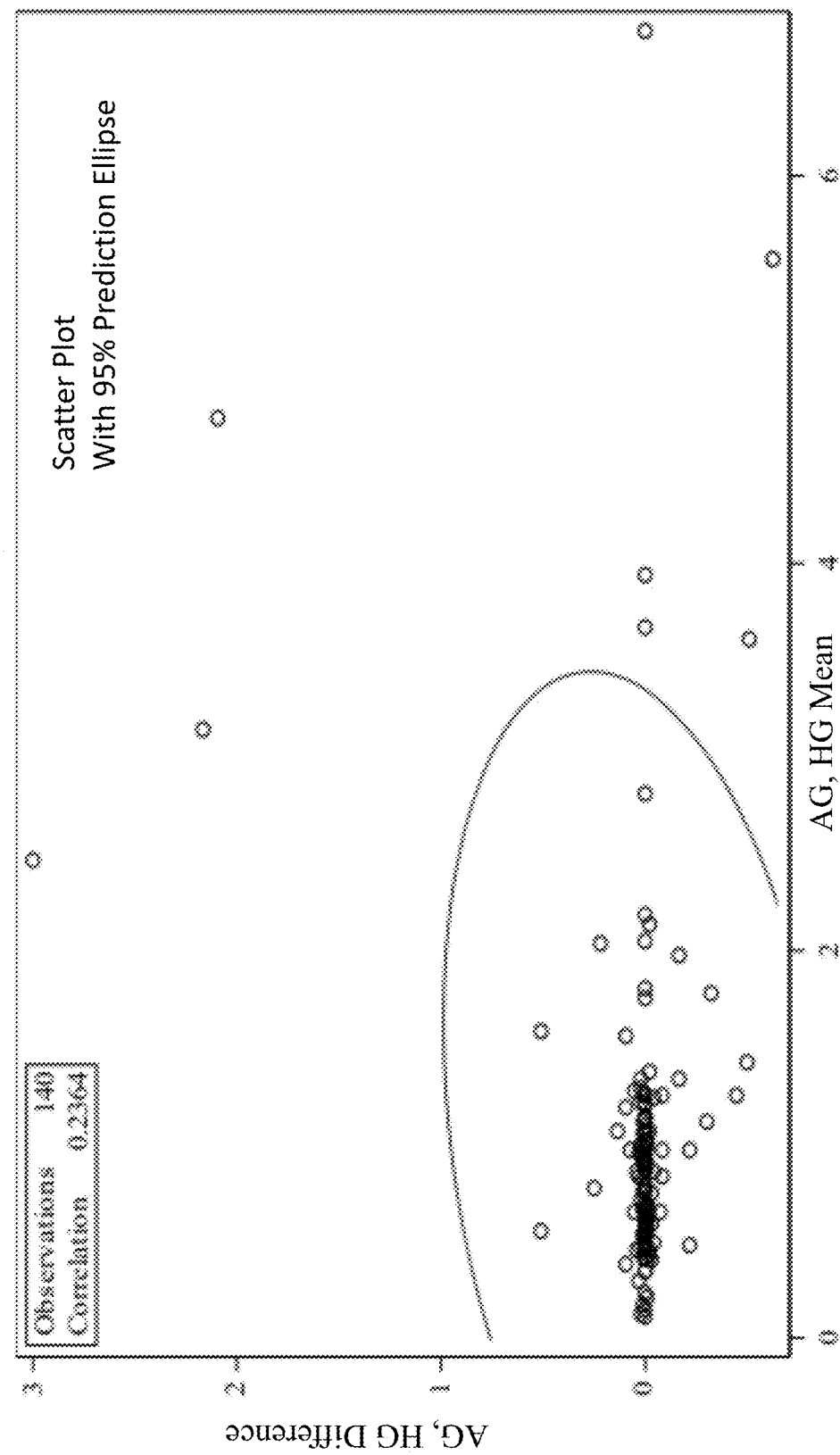

The relationship between VTF and invasive impedance was also evaluated. The mean of 0-1 harmonics of invasive impedance and MHFM (mean of VTF harmonics 5-6) were calculated. On initial investigation, there was no correlation between mean of impedance harmonics 0-1 of invasive impedance and RPA VTF MHFM (Pearson r=0.12, p=0.63) or LPA VTF MHFM (Pearson r=−0.17, p=0.47). The corresponding scatter plots are shown below in FIGS. 14A and 14B. As is clearly seen from scatter plot, there is no correlation for mean invasive impedance harmonics 0-1 and LPA VTF MHFM, FIG. 14B. But, on close examination of scatter plot for invasive impedance and RPA VTF MHFM (FIG. 14A)—it was found that there appears to be a strong correlation between mean invasive impedance harmonics 0-1and RPA VTF MHFM but this relationship is seemed to have been influenced by two 'outlier' points (green arrows, FIG. 14A) with relatively lower mean of 0-1 impedance harmonics and high VTF MHFM. These two 'outliers' corresponded to the patients with normal mean PA pressures and PVR between 2.5 to 3 (early PA remodeling) where the mean of invasive impedance harmonics 0-1 will be low due to only slightly elevated PVR but due to early PA remodeling, they had large high frequency magnitude of VTF with increased MHFM. With these two 'outliers' removed, there was a significant correlation of VTF MHFM and mean of invasive impedance harmonics 0-1 (Pearson r=0.74, 95% CI=0.42-0.89, p=0.0002, FIG. 15).

Intra-Observer And Inter-Observer Variability. There was high inter- and intra-observer reliability in the mean high frequency magnitude of the VTF as shown in Table 7 and FIGS. 16A, 16B, 16C, and 16D.

Table 7. Intra-observer and inter-observer variability in mean high frequency magnitude of velocity transfer function.

TABLE 7

Intra-observer and inter-observer variability in mean high frequency magnitude of velocity transfer function.

| Parameter | Correlation | | Agreement | |
| --- | --- | --- | --- | --- |
| | Intra-Class Correlation Coefficient | 95% CI | Relative bias ± SD | p-value ($\mu_0$: Bias = 0) |
| Intra-observer | 0.93 | 0.84-0.97 | 0.19 ± 0.54 | 0.13 |
| Inter-observer | 0.94 | 0.87-0.98 | 0.048 ± 0.28 | 0.97 |

Relationship With Right Ventricular Structure And Function. Invasive impedance showed significant association with RVMI, RVEDVI and RV mass to volume ratio (Table 8).

TABLE 8

Assessment of association of right ventricular remodeling with invasive impedance and velocity transfer function.

| Parameter | Invasive Impedance ($Z_{12}$) | | | VTF ($Z_{56}$) | | |
| --- | --- | --- | --- | --- | --- | --- |
| | $R^2$ | F ratio | p | $R^2$ | F ratio | p |
| RV ejection fraction | 0.04 | 0.73 | 0.4 | 0.44 | 13.41 | 0.0019* |
| RV stroke volume index | 0.05 | 0.82 | 0.38 | 0.3 | 7.13 | 0.016* |
| RV mass index | 0.5 | 16.73 | 0.0008* | 0.01 | 0.26 | 0.62 |
| RV end-diastolic volume index | 0.42 | 12.14 | 0.0028* | 0 | 0 | 0.99 |
| RV mass/volume ratio | 0.23 | 5.12 | 0.03* | 0.07 | 1.23 | 0.28 |

*p-value < 0.05.
RV: right ventricular;
VTF: velocity transfer function.

Figure 17A:
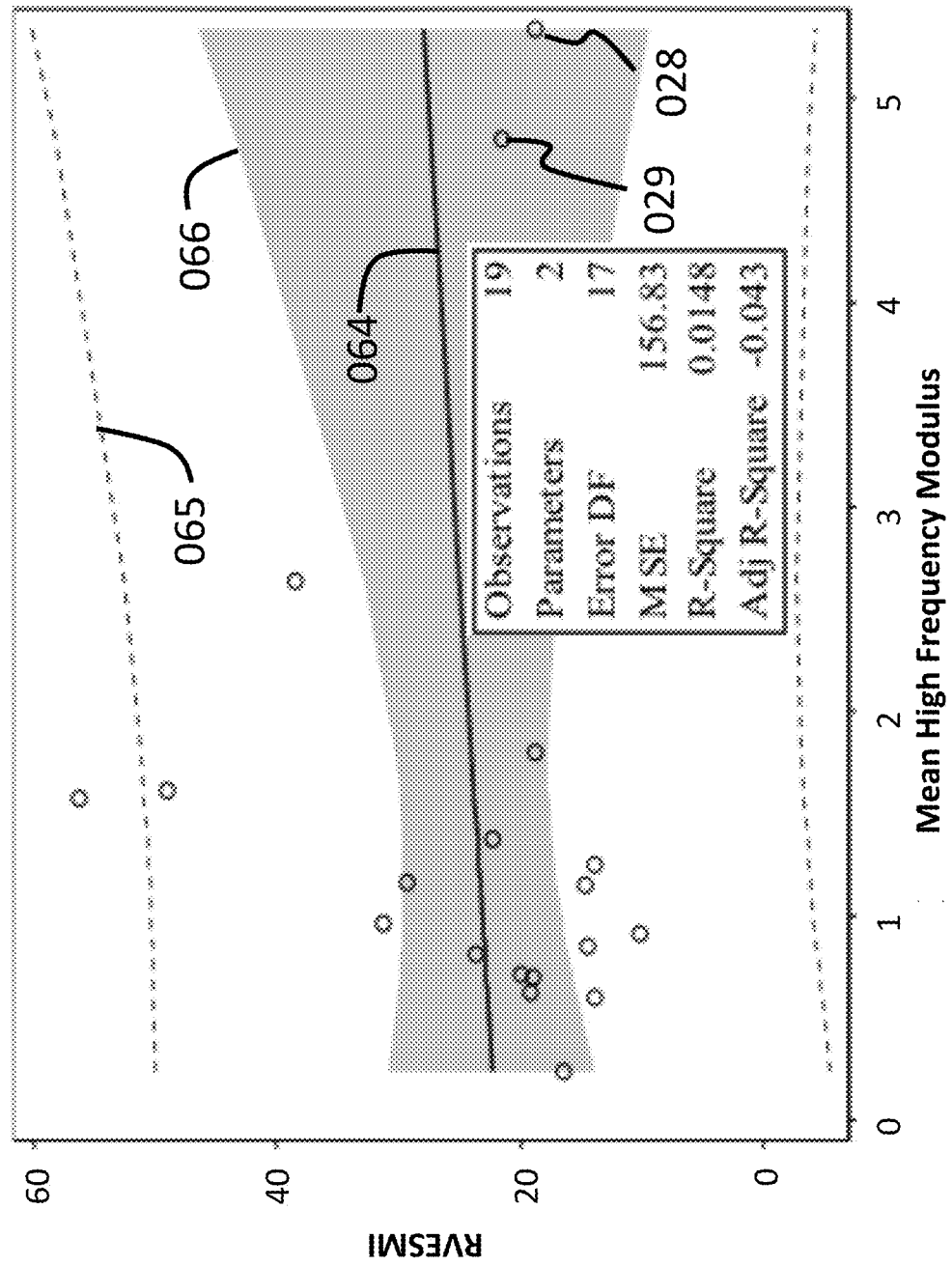
FIGS. 17A and 17B show fit plots of right ventricular mass index (RVESMI) and VTF mean high frequency magnitude (MHFM) without (FIG. 17A) and with (FIG. 17B) outliers removed. 028 and 029 are the 2 'outliers.' The solid lines (064, 067) denote the best fit line. The shaded regions (065, 068) denote the 95% confidence limits. The dashed lines (066, 069) denote the 95% prediction limits.
Figure 17B:
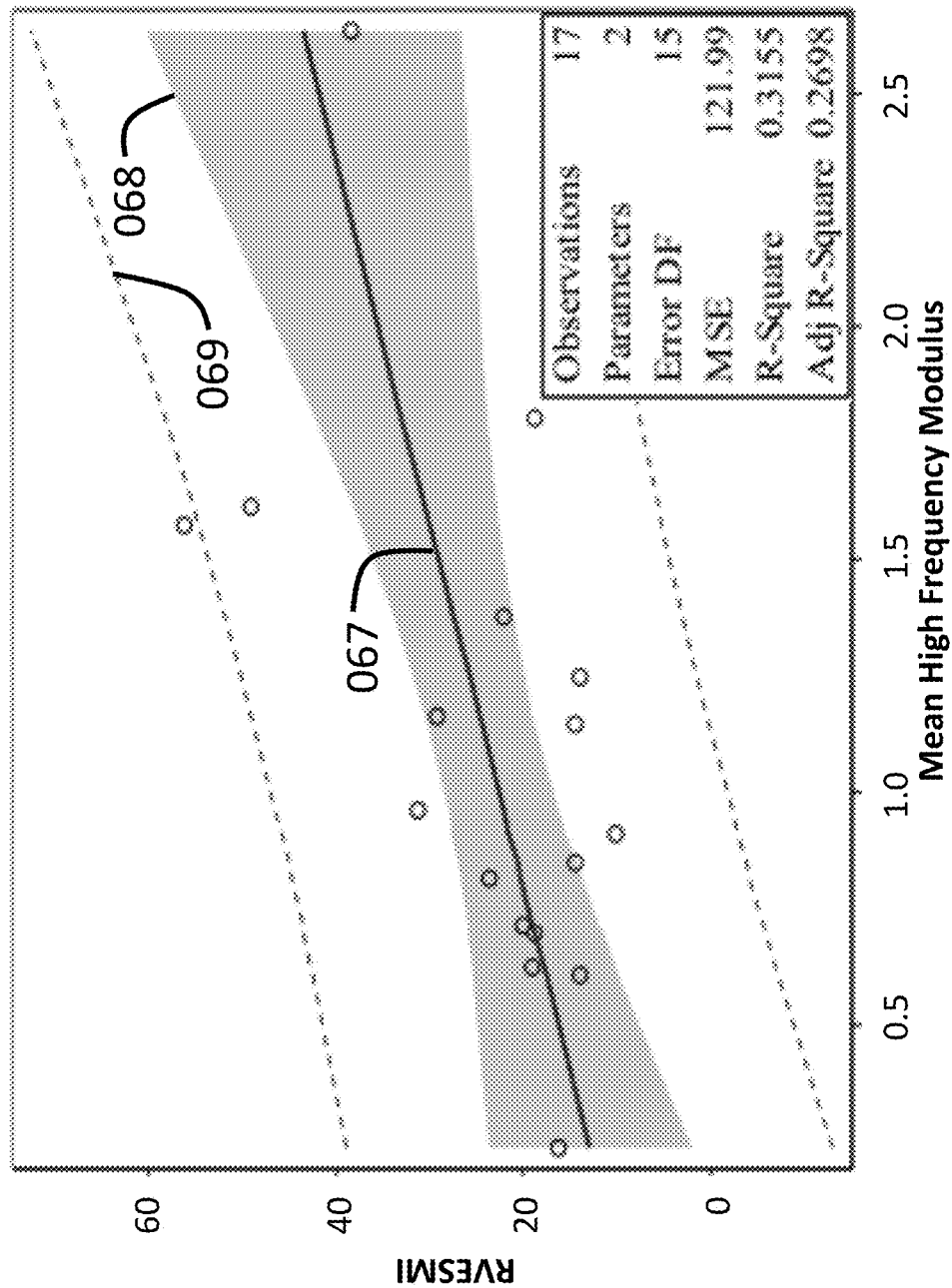
Figure 28:
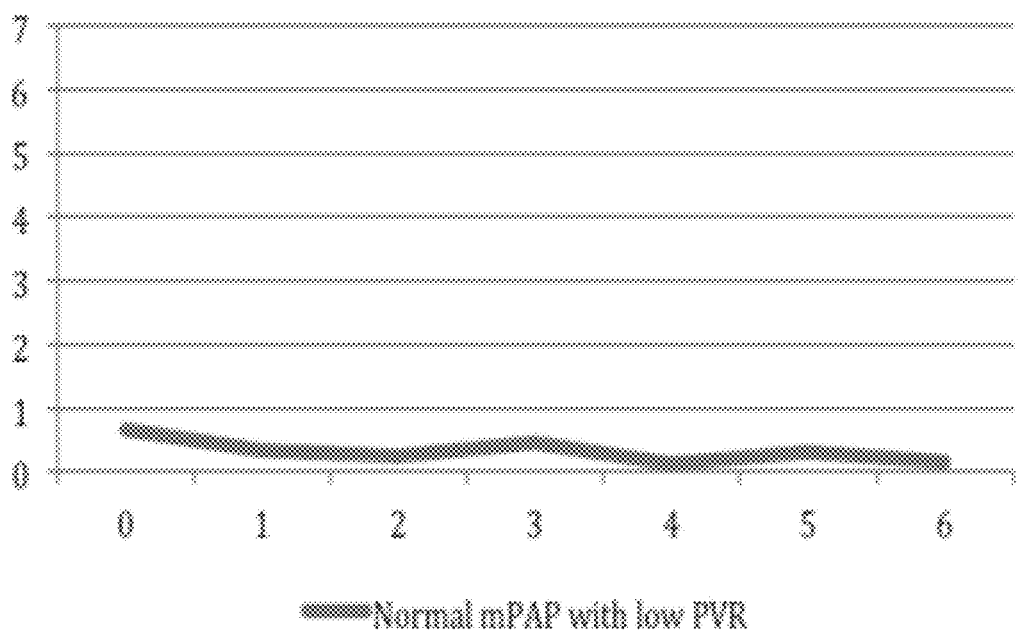
FIG. 28 shows the velocity transfer function curve over first six harmonics of a patient with scleroderma with otherwise no clinical pulmonary hypertension (mean PA pressure of 23 mm Hg), PCWP 12 mm Hg, CO 5.96 L/min, PVR 1.85 WU (normal)
Figure 29:
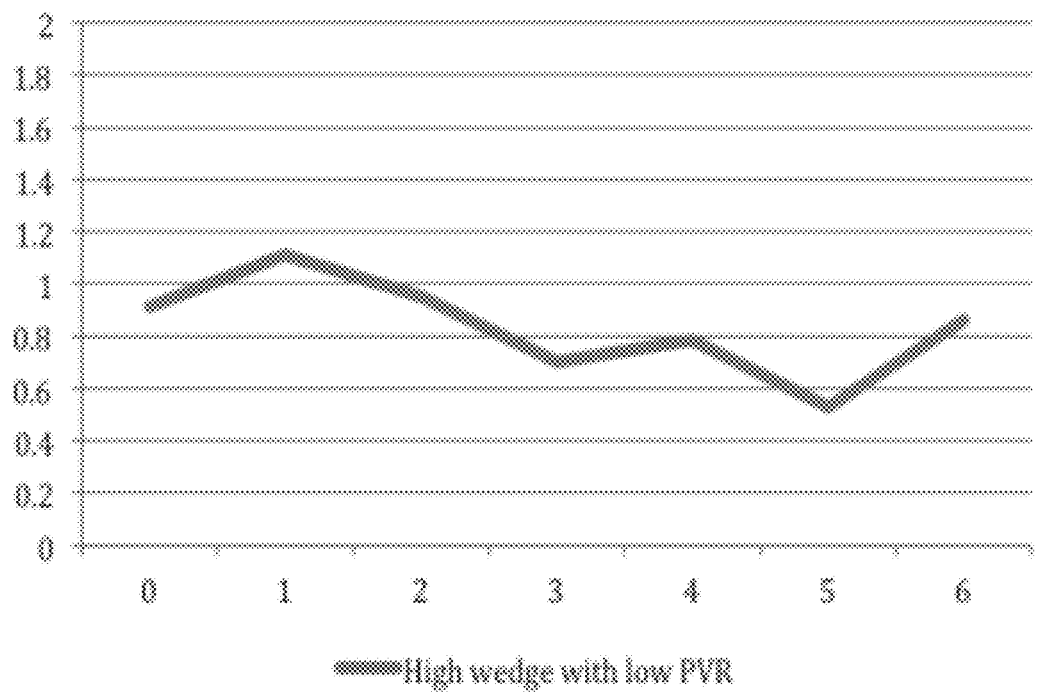
FIG. 29 shows the velocity transfer function curve over first six harmonics of a patient with heart failure with preserved ejection fraction with elevated pulmonary pressures (mean PA pressure of 30 mm Hg) secondary to elevated PCWP 20 mm Hg, CO 9.98 L/min and normal PVR 1.1 WU (pulmonary venous hypertension)

The VTF also showed significant association with RVEF with RVEF decreasing with increasing MHFM but no association was initially seen with RVMI (Table 8 and FIGS. 17A and 17B). Two 'outliers' were noted in the fit curve for the RVMI and MHFM (FIG. 17A, 028, 029). These 2 'outliers' corresponded to the patients with early PA remodeling (normal mean PA pressure with PVR between 2.5 to 3). They had high impedance but without proportionally increased RVMI likely due to being early in the disease process. After these 2 'outliers' were removed, the VTF showed significant association with RVMI ($R^2$=0.32, F ratio=6.91, p=0.01, FIG. 17B).

DISCUSSION

In this pilot study, a novel non-invasive assessment of PA impedance using VTF on CMR was proposed and it was shown for the first time that PA impedance can be detected completely non-invasively using VTF. It was demonstrated that the VTF can differentiate between spectrums of impedances and can detect patients with early PA mechanical remodeling. It was shown that this detection of PA impedance using VTF is independent of elevation in PCWP. It was also shown that VTF non-invasively evaluated RV-PA coupling with significant association of VTF with RVEF and RVMI. VTF was also robust in its measurement with high intra- and inter-observer agreement on repeated independent measurements of blinded studies.

In this study, there was significant association of invasive impedance with VTF when measured as change in velocity profile from proximal RPA to distal RPA but not from main PA to proximal LPA. This may potentially be due to LPA being short with early branching, thus, leading to inaccuracies in velocity measurements during phase-contrast MIll due to lack of a circular anatomic profile.

Figure 18:
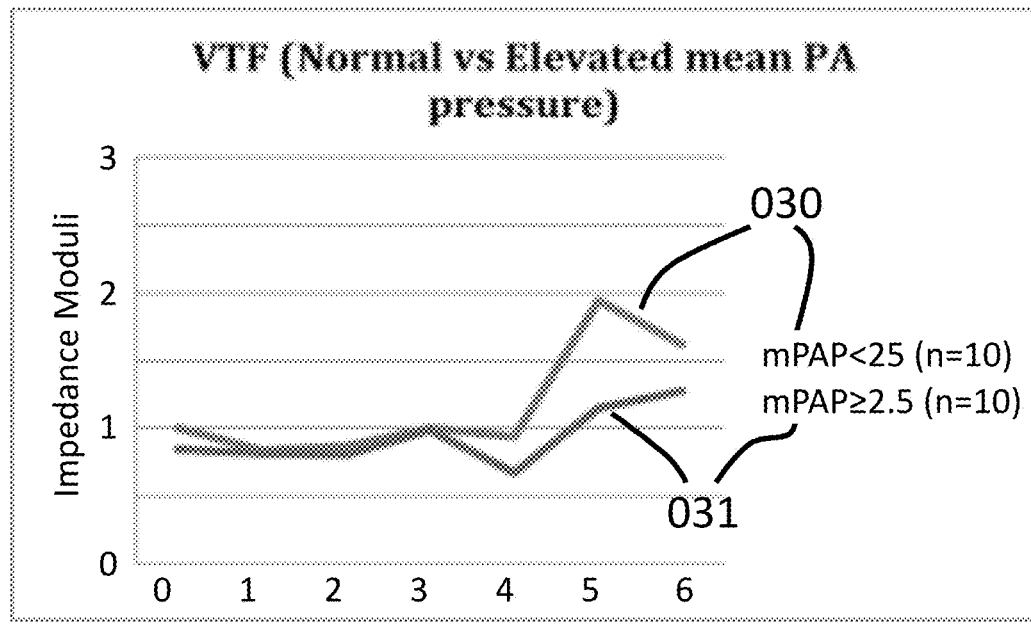
FIG. 18 shows velocity transfer function magnitudes curves over first six harmonics for elevated (031) versus normal (030) mean pulmonary arterial pressure groups.

Of the 20 study patients, 10 had normal PA pressures as defined by mean PA pressure of <25 mm Hg and 10 had normal PVR as defined by PVR <2.5 WU. VTF did not differentiate between normal PA pressure vs elevated PA pressure groups (FIG. 18), p-value for interaction of harmonics with group to predict impedance=0.74) but differentiated between normal PVR vs elevated PVR groups (FIG. 19), p-value for interaction of harmonics with group to predict impedance=0.001).

Figure 19:
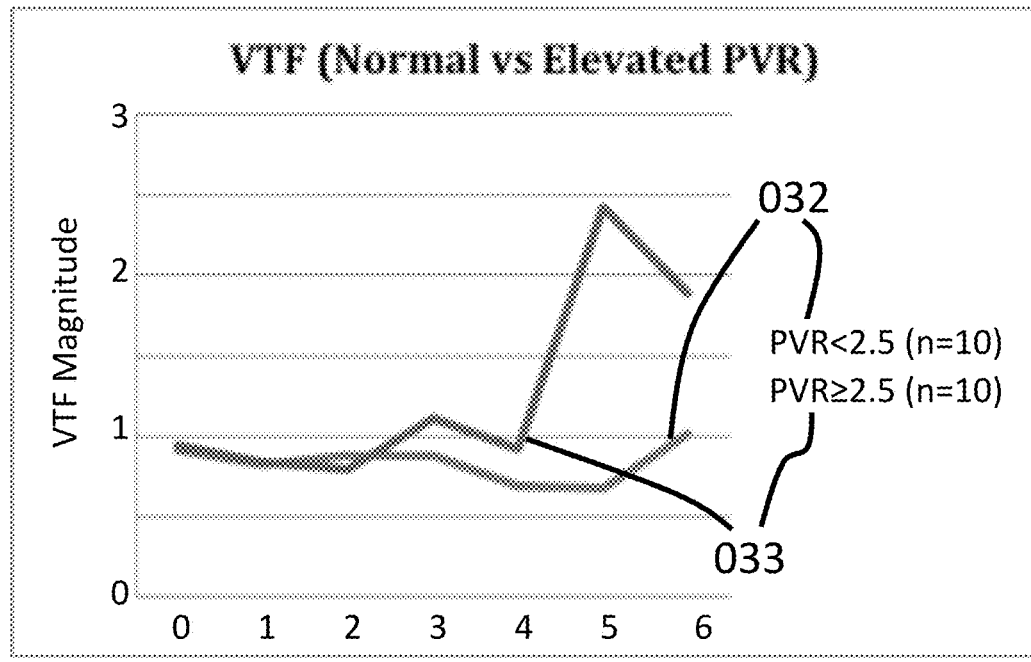
FIG. 19 shows velocity transfer function magnitudes curves over first six harmonics for patients with elevated (033) versus normal (032) pulmonary vascular resistance groups.
Figure 20:
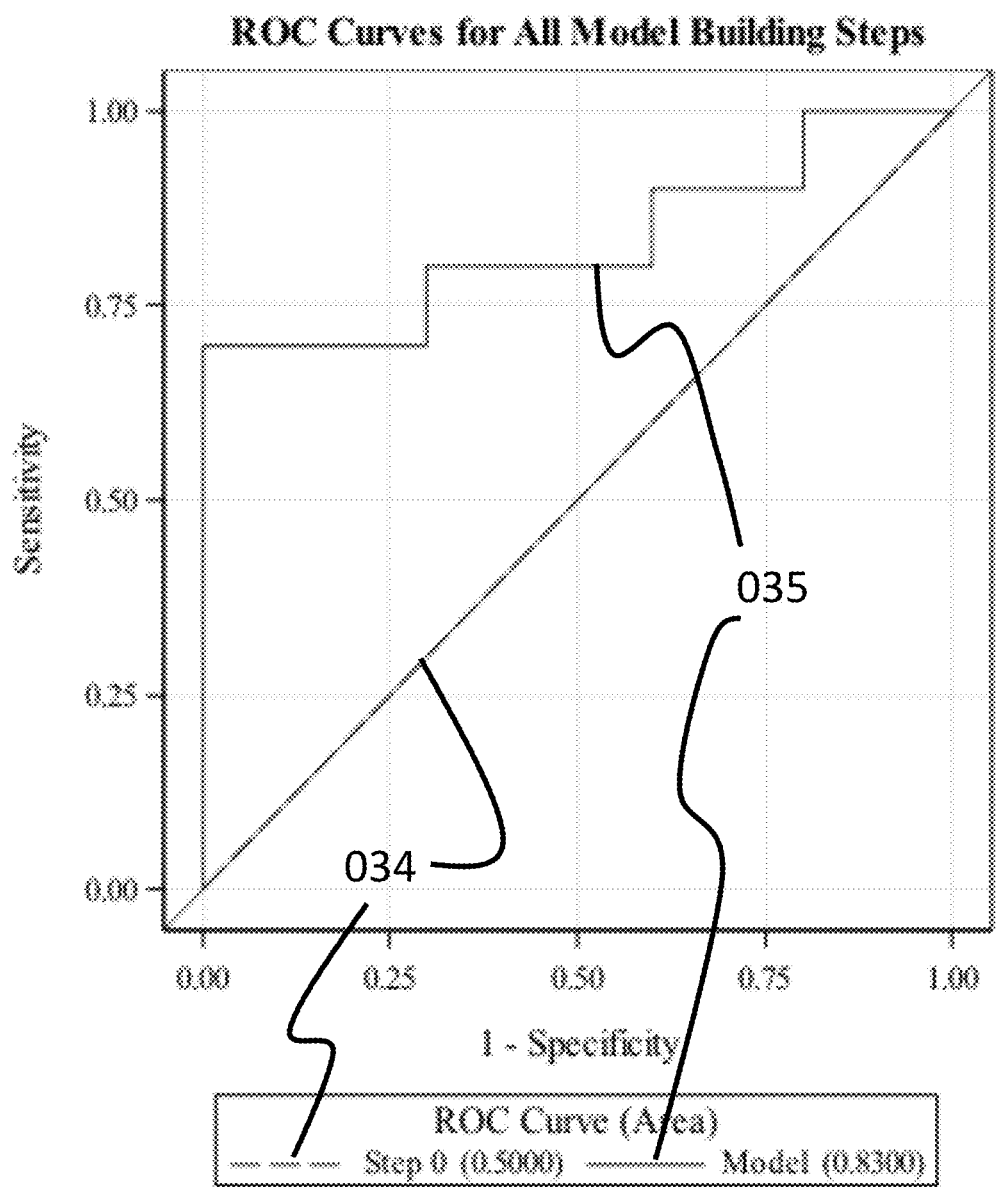
FIG. 20 shows the receiver operative characteristic curve for mean high frequency magnitude of velocity transfer function as a binary classifier for normal versus high pulmonary vascular resistance.

Mean high frequency magnitude, MHFM, of 5th and 6th harmonic of VTF was also studied. As seen in FIG. 19, MHFM was higher for high PVR group compared to normal PVR group (2.15±1.64 vs 0.84±0.3 respectively, t9.6=−2.3, p=0.04). On ROC analysis, MHFM showed significant performance capacity of MHFM to differentiate patients with normal PVR from high PVR (FIG. 20, AUC=83%, Chi-square=4.55, p=0.03). This demonstrates the potential of VTF to non-invasively differentiate between patients with normal PVR vs high PVR.

Figure 21:
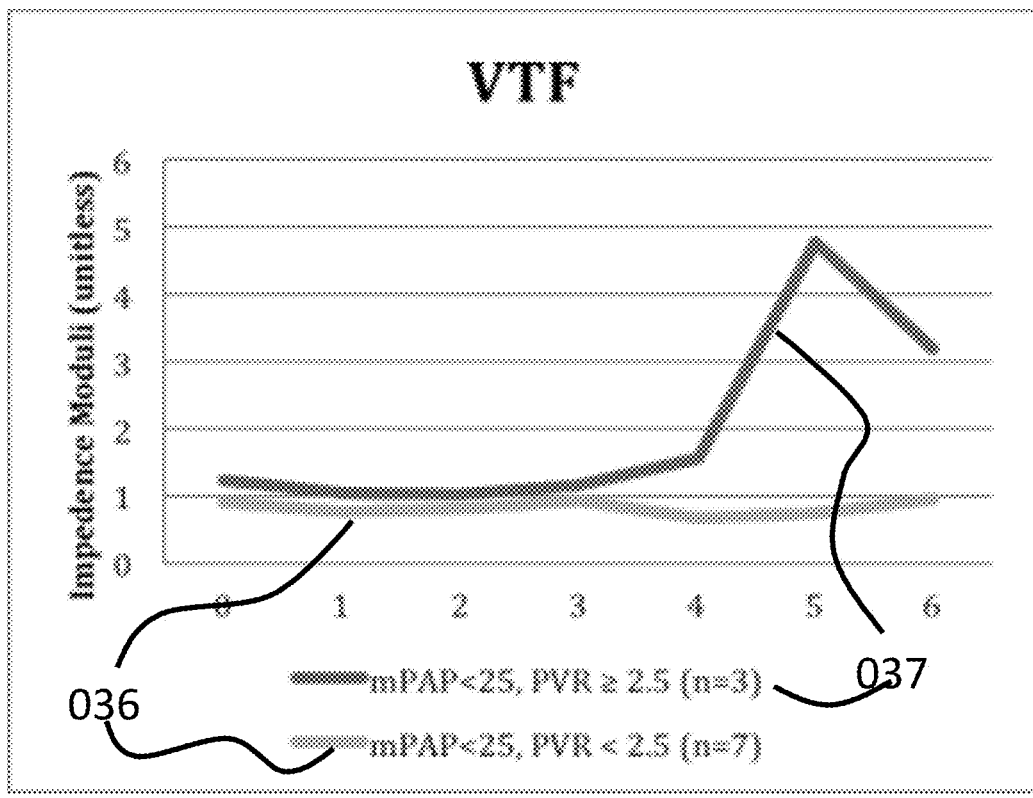
FIG. 21 shows velocity transfer function curves over first six harmonics in patients with normal pulmonary artery pressures with either normal (036) or elevated (037) pulmonary vascular resistance indicative of early pulmonary arterial remodeling.

Of the 10 patients with normal mean PA pressure <25 mm Hg, VTF differentiated between those with normal PVR <2.5 (n=7) and those with elevated PVR between 2.5-3 (n=3) as seen in FIG. 21. This indicates the potential of VTF to detect early PA stiffness in patients with otherwise normal PA pressures.

Figure 22:
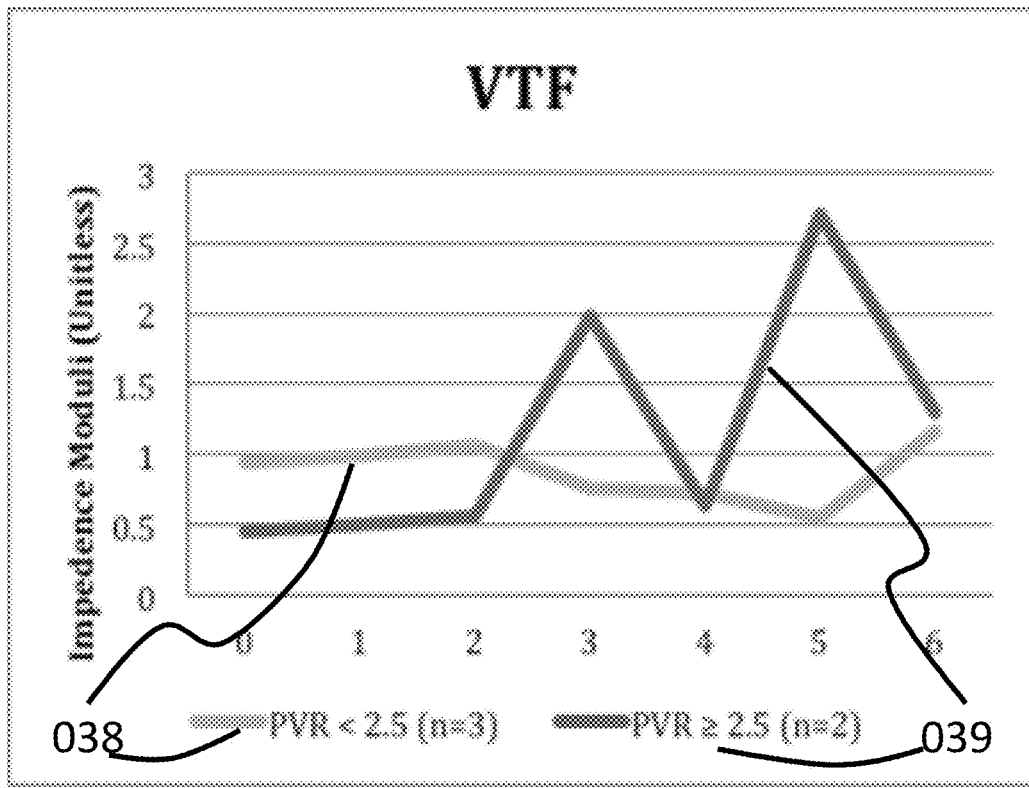
FIG. 22 shows velocity transfer function curves over first six harmonics in patients with elevated pulmonary artery pressures with elevated pulmonary capillary wedge pressures with either normal (038) or elevated (039) pulmonary vascular resistance.

In this study, 5 patients had elevated PCWP. Of these 3 had normal PVR (pulmonary venous hypertension) and 2 had elevated PVR (mixed pulmonary arterial and venous hypertension). VTF differentiated between normal and elevated PVR groups despite elevation in PCWP (FIG. 22). This indicates the potential of VTF to detect PA remodeling irrespective of elevation in PCWP. This can be very useful to study PA impedance and remodeling in patients with chronic left sided heart failure. Of note, although inferential statistics were not calculated for FIG. 21 and FIG. 22 due to small sample sizes in these sub-groups, these are hypothesis generating that should be tested in larger studies.

This study showed that VTF has strong association with invasive impedance. This can also be seen in corresponding invasive impedance and VTF curves of patients with normal and high PVR (FIG. 23A and FIG. 23B) as well as patients with normal mean PA pressure with or without elevated PVR (FIG. 24A and FIG. 24B).

Figure 23A:
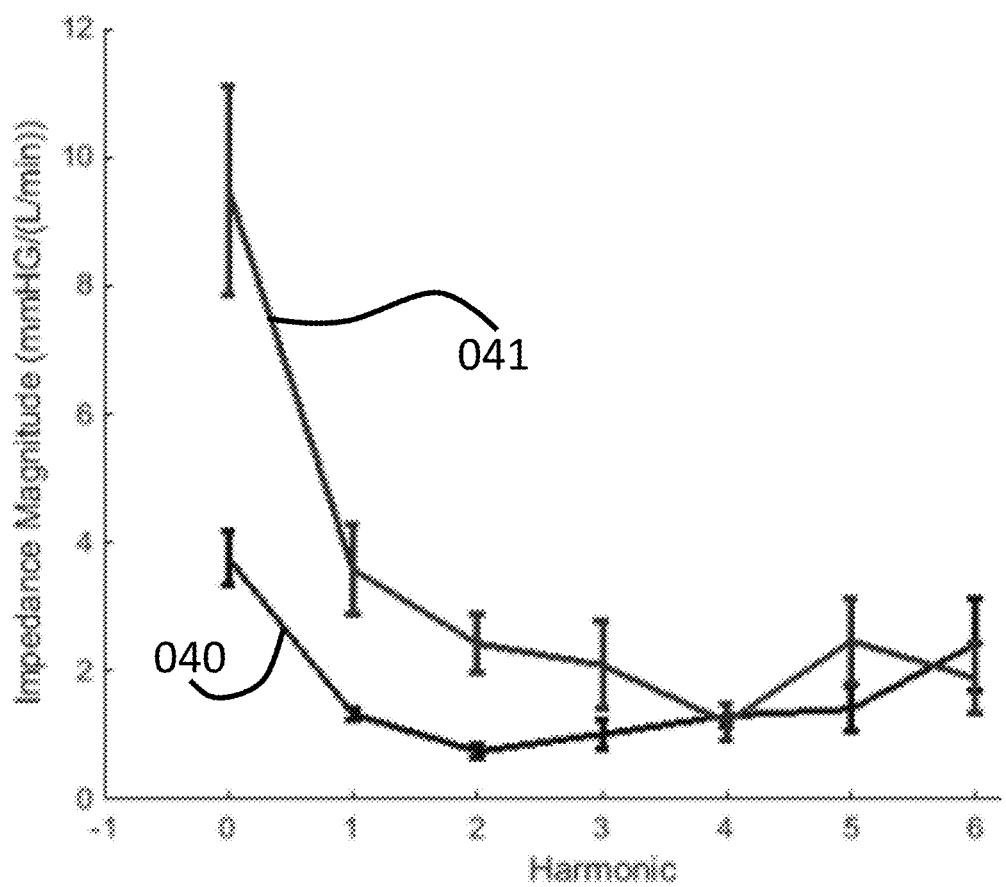
FIGS. 23A and 23B show invasive impedance curves (FIG. 23A) and corresponding velocity transfer function curves (FIG. 23B) over first six harmonics in patients with normal (040, 042) or elevated (041, 043) pulmonary vascular resistance. Error bars denote ±1 standard error.
Figure 23B:
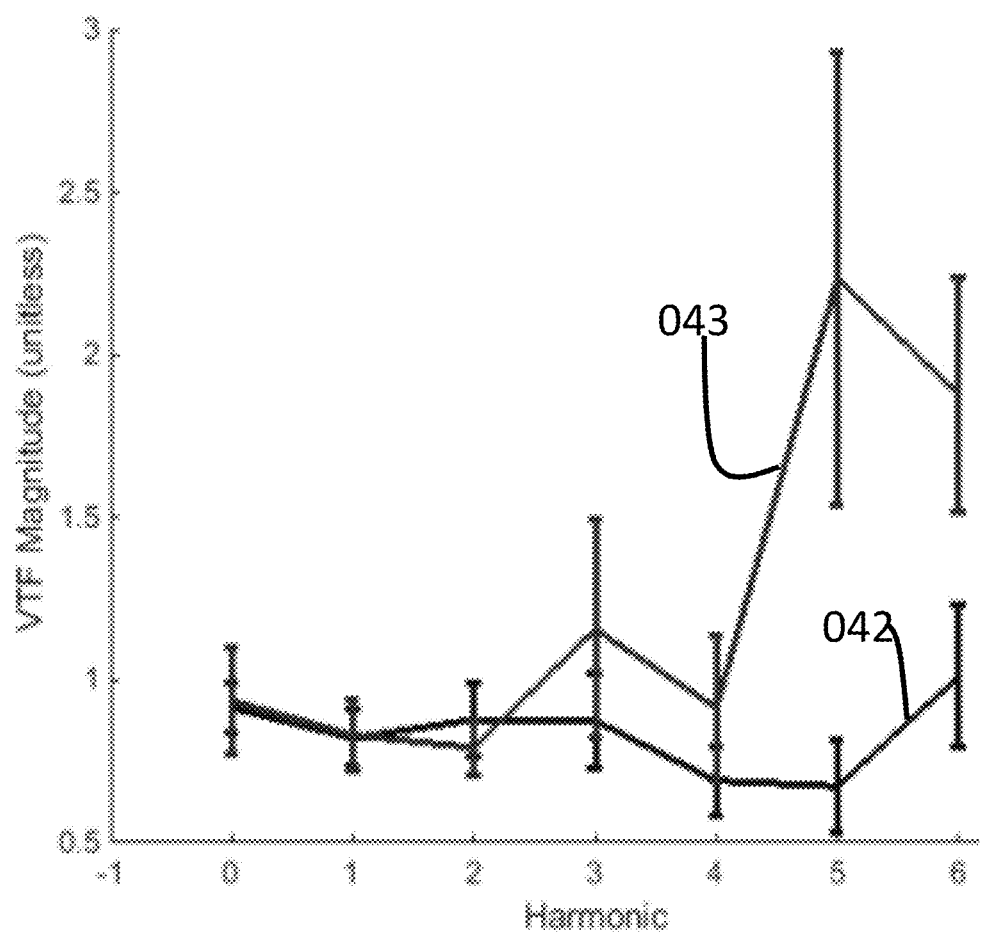
Figure 24A:
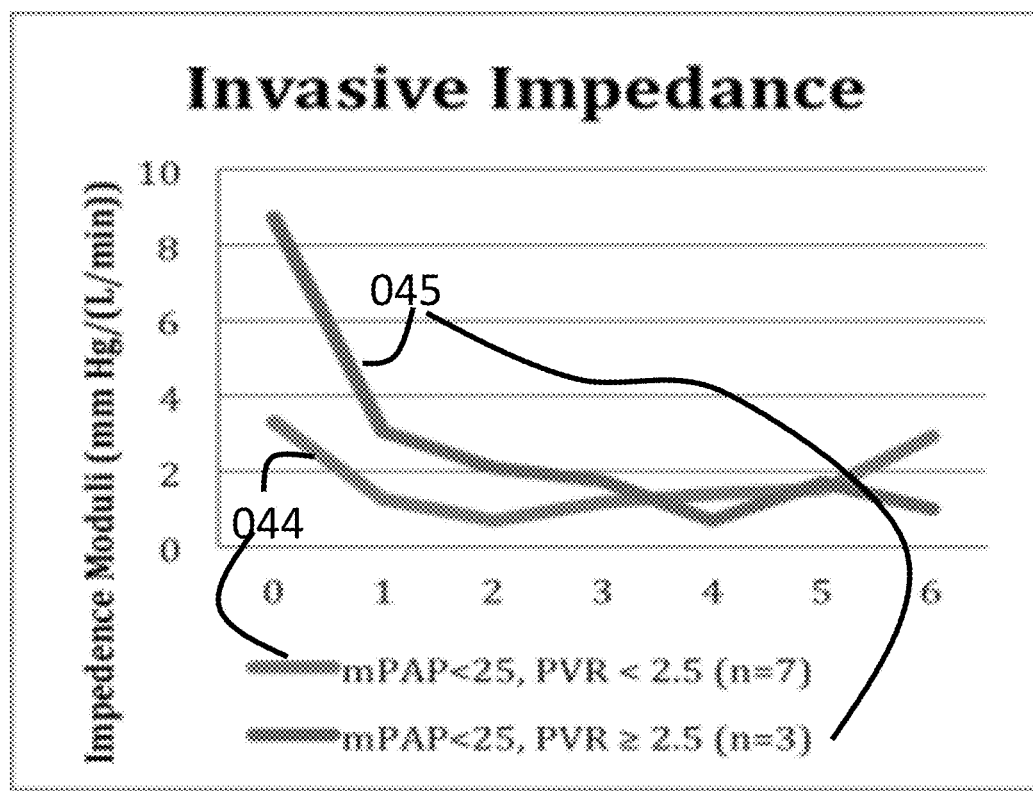
FIGS. 24A and 24B show invasive impedance curves (FIG. 24A) and corresponding velocity transfer function curves (FIG. 24B) over first six harmonics in patients with normal mean pulmonary arterial pressures with either normal (044, 046) or elevated (045, 047) pulmonary vascular resistance.
Figure 24B:
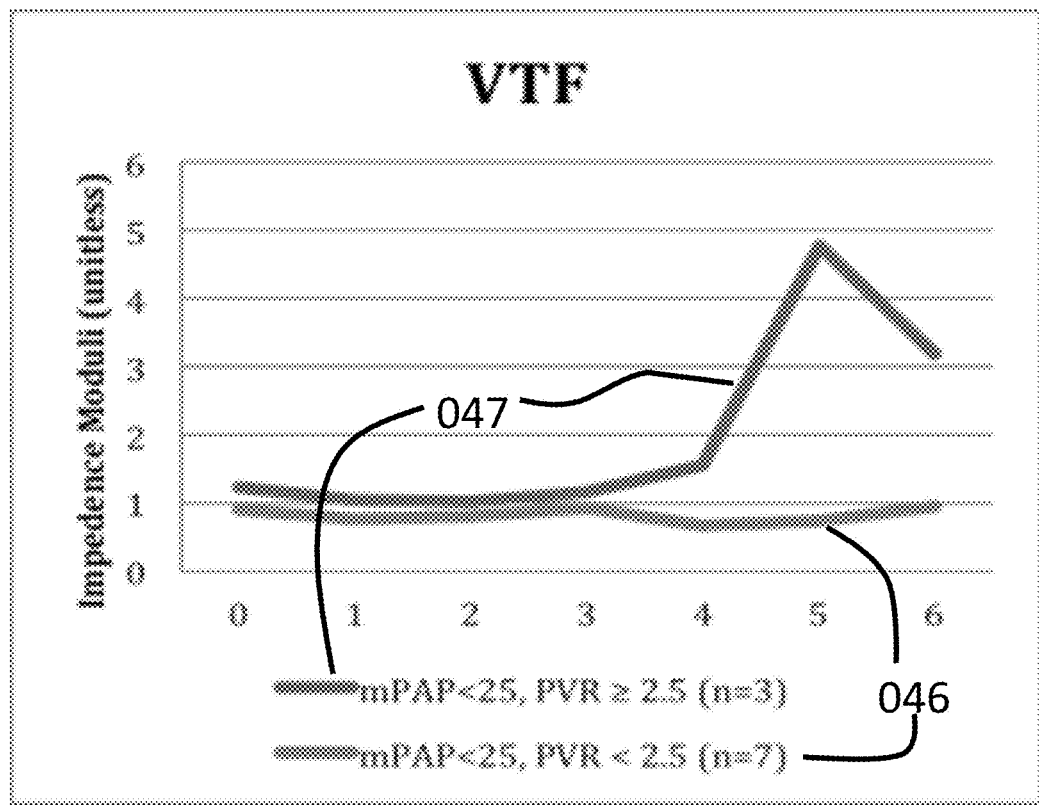

As seen in FIG. 23A, and FIG. 24A, normal invasive impedance curves show a low magnitude at zero harmonic, then rapidly descends down with first minimum magnitude occurring at low harmonics (1 or 2). Impedance magnitude curves of patients with high PVR show high magnitude at zero harmonic, and then slowly descends down with first minimum occurring at later harmonics (3 or 4 or higher). This is the expected behavior of impedance curves (Nichols, W. and M. O'Rourke, *McDonald's Blood Flow in Arteries*. 5th ed. 2005, London: Hodder Arnold.), lending support to the invasive impedance measurements in this study. Corresponding VTF curves in FIG. 23B and FIG. 24B demonstrate that VTF curves start at similar zero harmonic for patients with normal or high PVR but then show differentiation at higher harmonics (5 or 6) when impedance magnitudes increase in patients with high PVR. For invasive impedance, the pressure and flow curves have different mean values, which reflects as high impedance magnitudes at zero and lower impedance harmonics. In contrast, for VTF, the input (proximal RPA) and output (distal RPA) velocity curves have close to the same mean value, so the zero and lower VTF harmonics are close to 1 before separating at higher harmonics.

Individual Patient Studies

Figure 25:
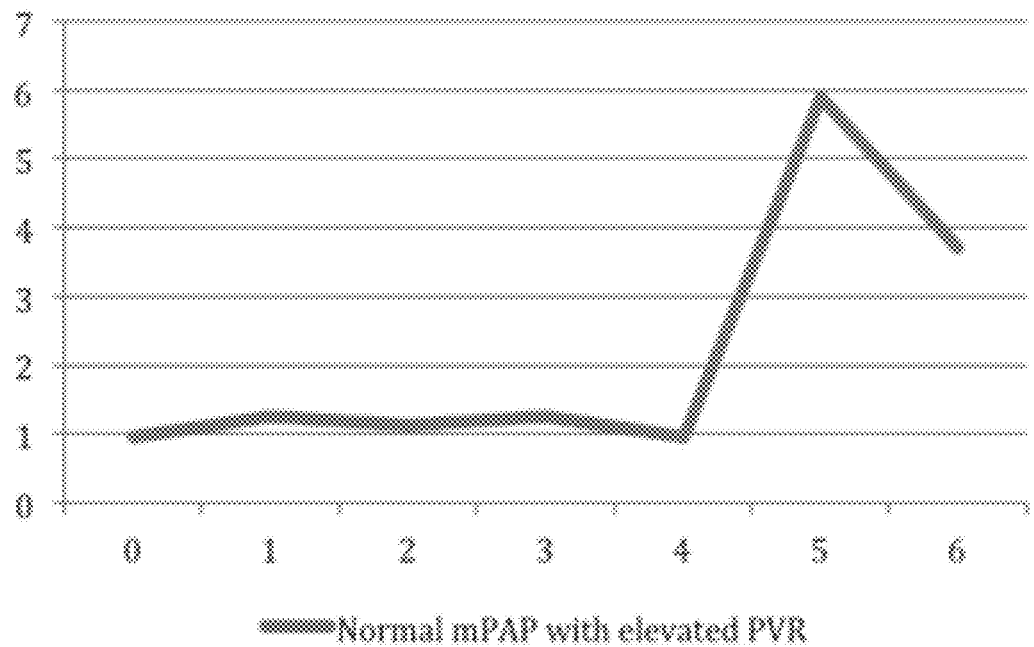
FIG. 25 shows the velocity transfer function curve over first six harmonics of a patient with idiopathic pulmonary fibrosis with otherwise no clinical pulmonary hypertension (mean PA pressure of 19 mm Hg), PCWP 5 mm Hg, CO 5.54 L/min, PVR 2.525 WU (early PA remodeling)
Figure 26:
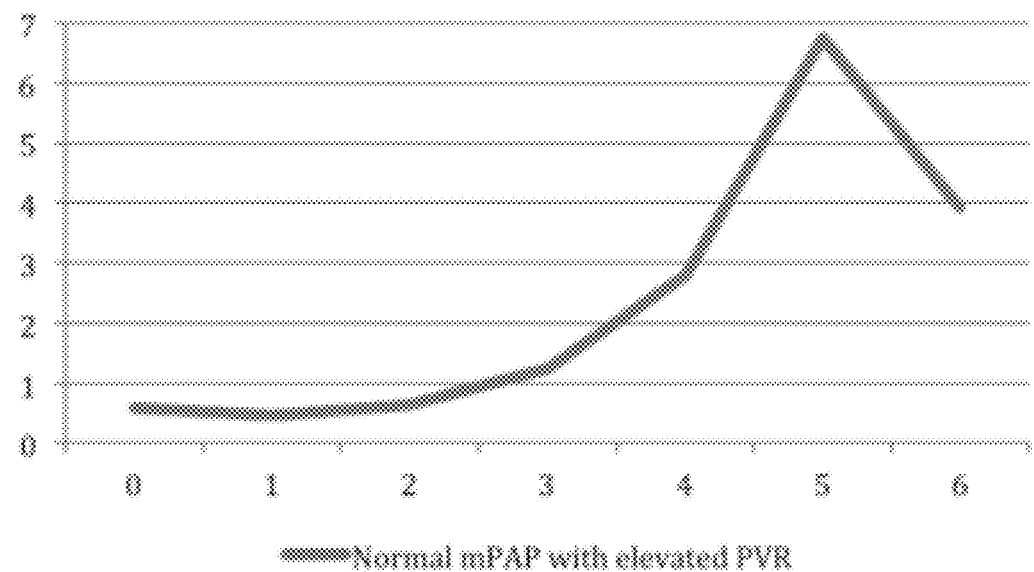
FIG. 26 shows the velocity transfer function curve over first six harmonics of a patient with idiopathic pulmonary fibrosis with otherwise no clinical pulmonary hypertension (mean PA pressure of 22 mm Hg), PCWP 6 mm Hg, CO 5.41 L/min, PVR 2.96 WU (early PA remodeling)
Figure 27:
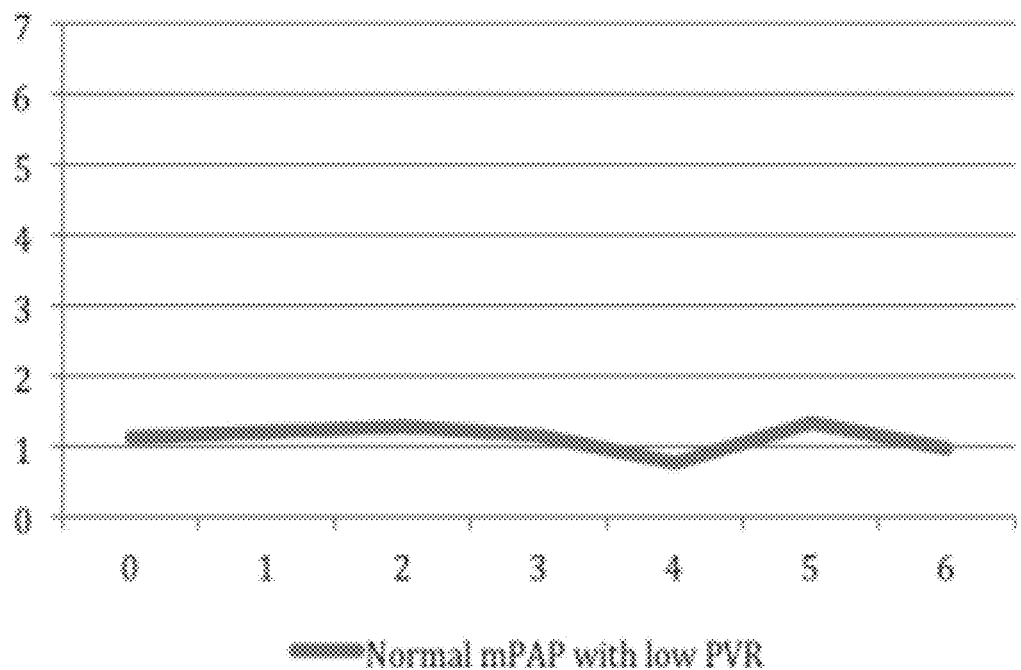
FIG. 27 shows the velocity transfer function curve over first six harmonics of a patient with chronic left ventricular ischemic cardiomyopathy from an old left anterior descending artery dissection with otherwise no clinical pulmonary hypertension (mean PA pressure of 18 mm Hg), PCWP 11 mm Hg, CO 3.99 L/min, PVR 1.75 WU (normal)
Figure 30:
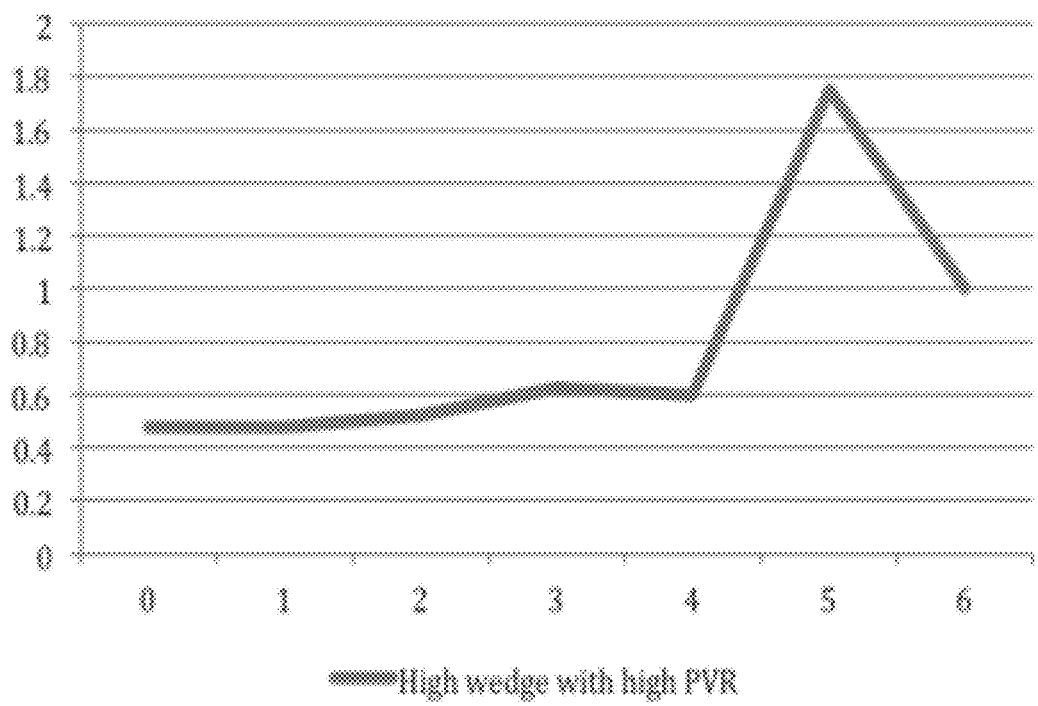
FIG. 30 shows the velocity transfer function curve over first six harmonics of a patient with restrictive cardiomyopathy due to cardiac amyloidosis with elevated pulmonary pressures (mean PA pressure of 36 mm Hg) secondary to elevated PCWP 23 mm Hg, CO 3.64 L/min and elevated PVR 3.575 WU (mixed pulmonary venous and arterial hypertension)

The following individual patient examples from this study illustrates the potential ability of VTF as a powerful tool to non-invasively detect early pulmonary arterial remodeling (PVR between 2.5 to 3, FIG. 25, FIG. 26) from normal PVR <2.5 (FIG. 27, FIG. 28) in patients with otherwise normal mean PA pressures. It also demonstrates the potential ability of VTF to distinguish high vs normal pulmonary vascular resistance despite elevated PCWP (FIG. 29, FIG. 30) in individual patients.

Strengths of Velocity Transfer Function

This study demonstrates for the first time the feasibility of VTF as a non-invasive highly reliable method of assessing pulmonary arterial impedance and assessment of RV-PA axis. It is reproducible, relatively inexpensive, requires no ionizing radiation, takes less than 10 minutes to obtain using phase-contrast CMR study which can also be extended to include cine-CMR in the same session for assessment of RV structure and function.

Limitations

VTF is a surrogate of invasive impedance and not an exact measure of invasive impedance. Invasive impedance is the ratio of magnitudes of pressure by flow in frequency domain whereas VTF is the ratio of magnitudes of output velocity profile to input velocity profile in frequency domain. This study demonstrated that VTF is an accurate and reliable non-invasive surrogate of PA impedance and thus, can be used as a screening tool before more expensive or invasive tests are considered. In this study, invasive impedance was measured using hybrid acquisition of pressure data from RHC and flow data from Doppler echocardiography. Although completely invasive assessment of PA impedance is feasible and was utilized in older studies in animals (Milnor, W., D. Bergel, and J. Bargainer, Hydraulic power associated with pulmonary blood flow and its relation to heart rate. *Circ Res.*, 1966. 19(3): p. 467-80; Caro, C. G. and D. D. Mc, The relation of pulsatile pressure and flow in the pulmonary vascular bed. *J Physiol*, 1961. 157: p. 426-53; Patel, D. J., F. M. Defreitas, and D. L. Fry, Hydraulic input impedance to aorta and pulmonary artery in dogs. *J Appl Physiol*, 1963. 18: p. 134-40; Bergel, D. H. and W. R. Milnor, Pulmonary Vascular Impedance in the Dog. *Circ Res*, 1965. 16: p. 401-15; van den Bos, G. C., N. Westerhof, and O. S. Randall, Pulse wave reflection: can it explain the differences between systemic and pulmonary pressure and flow waves? A study in dogs. *Circ Res*, 1982. 51(4): p. 479-85; Maggiorini, M., et al., Effects of pulmonary embolism on pulmonary vascular impedance in dogs and minipigs. *J Appl Physiol* (1985), 1998. 84(3): p. 815-21; Santana, D. B., et al., Pulmonary artery smooth muscle activation attenuates arterial dysfunction during acute pulmonary hypertension. *J Appl Physiol* (1985), 2005. 98(2): p. 605-13; Greenwald, S. E., R. J. Johnson, and S. G. Haworth, Pulmonary vascular input impedance in the newborn and infant pig. *Cardiovasc Res*, 1985. 19(1): p. 44-50; Leather, H. A., et al., Effects of vasopressin on right ventricular function in an experimental model of acute pulmonary hypertension. *Crit Care Med*, 2002. 30(11): p. 2548-52.) and humans (Milnor, W. R., et al., Pulmonary Arterial Pulse Wave Velocity and Impedance in Man. *Circ Res*, 1969. 25(6): p. 637-649; Wilcox, B. R. and C. L. Lucas, Pulmonary input impedance in children with left-right shunt. *J Surg Res*, 1980. 29(1): p. 40-9; Murgo, J. P. and N. Westerhof, Input impedance of the pulmonary arterial system in normal man. Effects of respiration and comparison to systemic impedance. *Circ Res*, 1984. 54(6): p. 666-73; Kussmaul, W. G., J. M. Wieland, and W. K. Laskey, Pressure-flow relations in the pulmonary artery during myocardial ischaemia: implications for right ventricular function in coronary disease. *Cardiovasc Res*, 1988. 22(9): p. 627-38; Chen, Y. T., et al., Aortic and pulmonary input impedance in patients with cor pulmonale. *Jpn Heart J*, 1990. 31(5): p. 619-29; Kussmaul, W. G., 3rd, et al., Effects of pacing tachycardia and balloon valvuloplasty on pulmonary artery impedance and hydraulic power in mitral stenosis. Circulation, 1992. 86(6): p. 1770-9.) but most recent human studies (Hunter, K. S., et al., Pulmonary vascular input impedance is a combined measure of pulmonary vascular resistance and stiffness and predicts clinical outcomes better than pulmonary vascular resistance alone in pediatric patients with pulmonary hypertension. *Am Heart J*, 2008. 155(1): p. 166-74; Huez, S., et al., Feasibility of routine pulmonary arterial impedance measurements in pulmonary hypertension. *Chest*, 2004. 125(6): p. 2121-8.) on PA impedance have used the hybrid acquisition due to practicality and relative low expense. In addition, the behavior of invasive impedance in current study's patients (FIG. 23A and FIG. 24A) matched expected impedance curve behavior (Nichols, W. and M. O'Rourke, *McDonald's Blood Flow in Arteries*. 5th ed. 2005, London: Hodder Arnold.). Another limitation is use of fluid-filled catheter for acquisition of invasive PA pressure measurements during RHC as opposed to use of high-fidelity catheters which are not available for routine clinical practice and are expensive to use. The other limitation of this study is non-simultaneous acquisition of invasive impedance (RHC-Doppler) and VTF (CMR). There are very few hybrid MRI-RHC suites in the world. Thus, for all practical purposes, the only way currently to acquire RHC and MRI data in a given patient is sequential. In this study, in order to minimize hemodynamic alterations between RHC and MRI acquisition, all studies in a given patient were obtained on the same day as close to each other as feasible (Table 3). There was strong intra-class agreement of hemodynamic parameters of HR, BP and CI at time of RHC and MRI (Table 3). In addition, as impedance analysis is in frequency domain, rather than time domain, it is unlikely that the differences in hemodynamic parameters in physiologic range will adversely affect the impedance measurements between RHC and MRI.

CONCLUSIONS

In this study, the following conclusions were reached:

Conclusion 1: It was demonstrated, for the first time, the feasibility of using non-invasive VTF as a surrogate for invasive PA impedance measurement.

Conclusion 2: It was demonstrated that the VTF can differentiate between spectrums of impedance magnitudes and can detect patients with early PA mechanical remodeling.

Conclusion 3: It showed the potential of VTF in detecting PA impedance independent of elevation in PCWP.

Conclusion 4: VTF non-invasively evaluated RV-PA coupling with significant association with RVEF and RVMI.

Conclusion 5: VTF was also robust in its measurement with high intra- and inter-observer agreement on repeated independent measurements of blinded studies.

Future Directions

1. This was a pilot study. VTF would need to be validated in larger studies.
2. Utility and robustness of VTF would need to be evaluated in special patient populations. Some of these would be patients with: chronic obstructive lung disease, heart failure with preserved ejection fraction, heart failure with reduced ejection fraction, connective tissue disorders
3. Relationship of VTF to clinical outcomes needs to be assessed in longitudinal studies.
4. Serial changes in VTF with disease progression or with therapy need to be investigated in longitudinal studies.

Clinical Example 3

In this embodiment, a single heartbeat pressure waveform was measured with an invasive left heart catheter at a point distal to a suspected stenosis in a coronary artery (earliest time point) and considered to be a reference waveform. The catheter was then pulled back through the area of suspected stenosis yielding a series of single heartbeat waveforms (later time points). A series of PTFs $S_{Pi}(f)$ were then computed using the aforementioned formula:

This procedure was performed on two patients with coronary artery disease. A sequence of PTFs were calculated as described above, and the PTF harmonics versus time are plotted in FIGS. 31A, 31B, 31C, 32A, 32B, and 32C.

Figure 31A:
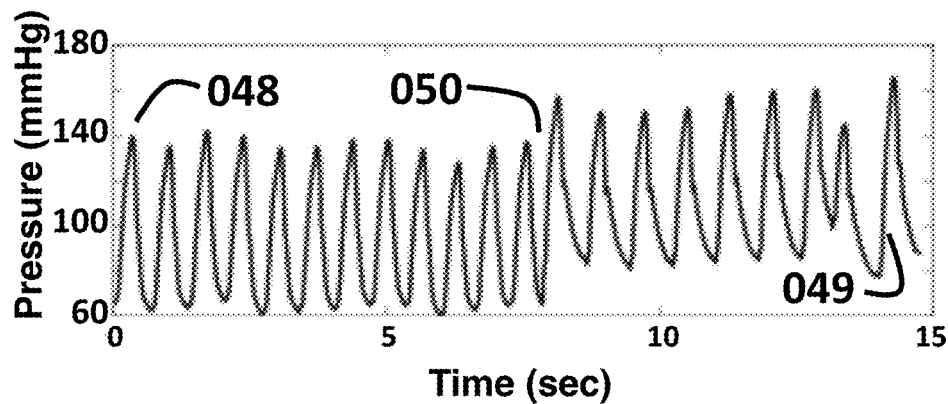
FIG. 31A shows a series of pressure waves as catheter tip is pulled back from a distal point (048) across a stenosis to a proximal point (049)

FIG. 31A shows a series of pressure waves as catheter tip is pulled back from a distal point (048) across a stenosis to a proximal point (049).

Figure 31B:
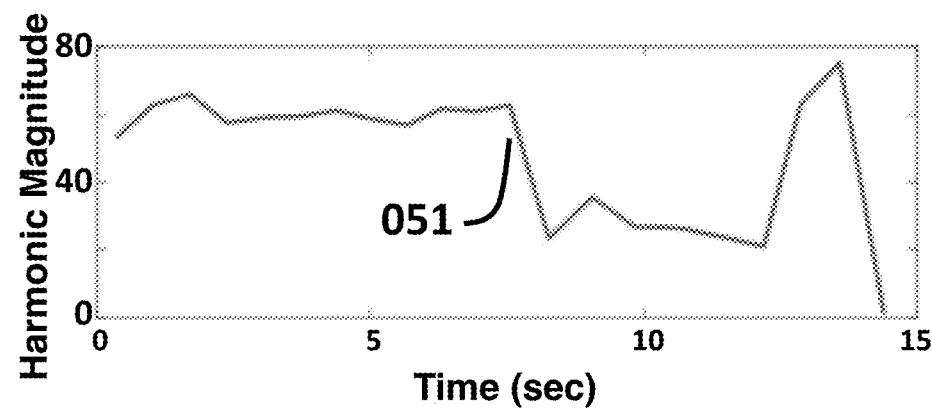
FIG. 31B shows the largest magnitude harmonic (harmonic 3) of the PTF versus time, where the change in harmonic 3 when the catheter crosses the stenosis near 050 in FIG. 31A and 051 in FIG. 31B.

FIG. 31B shows the largest magnitude harmonic (harmonic 3) of the PTF versus time. Note the change in harmonic 3 (051) when the catheter crosses the stenosis near 050 in FIG. 31A and 051 in FIG. 31B.

Figure 31C:
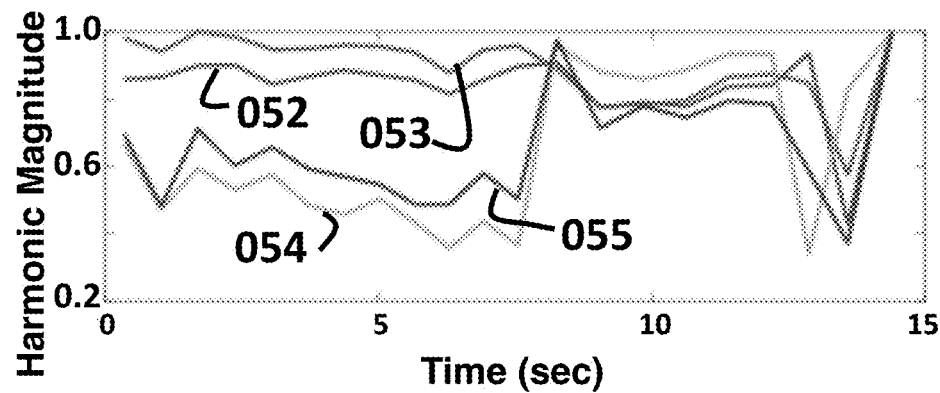
FIG. 31C shows harmonics 0 (052), which is also the FFR, 1 (053), 2 (054) and 4 (055), which exhibit little change as the catheter tip crosses the stenosis.

FIG. 31C shows harmonics 0 (052), which is also the FFR, 1 (053), 2 (054) and 4 (055), which exhibit little change as the catheter tip crosses the stenosis.

Figure 32A:
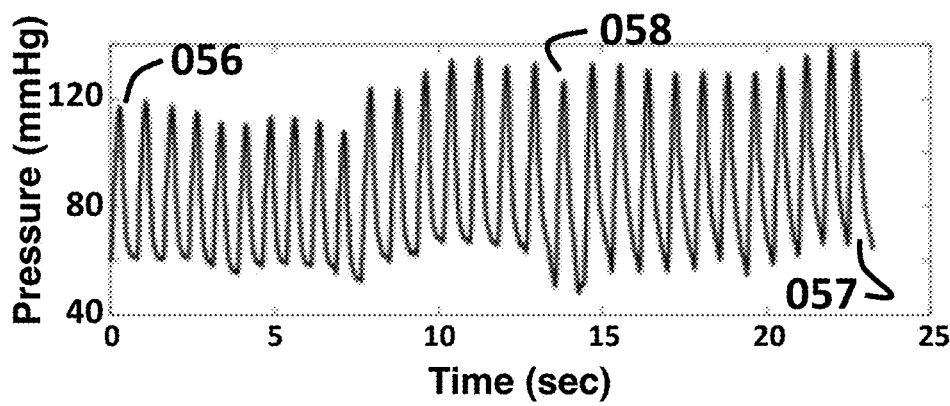
FIG. 32A shows a series of pressure waves as catheter tip is pulled back from a distal point (056) across a stenosis to a proximal point (057)

FIG. 32A shows a series of pressure waves as catheter tip is pulled back from a distal point (056) across a stenosis to a proximal point (057).

Figure 32B:
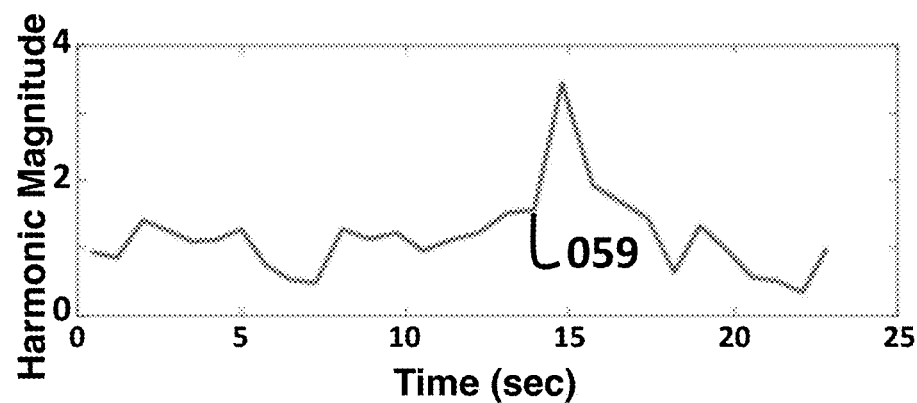
FIG. 32B shows the largest magnitude harmonic (harmonic 3) of the PTF versus time, where the change in harmonic 3 when the catheter crosses the stenosis near 058 in FIG. 32A and 059 in FIG. 32B.

FIG. 32B shows the largest magnitude harmonic (harmonic 3) of the PTF versus time. Note the change in harmonic 3 when the catheter crosses the stenosis near 058 in FIG. 32A and 059 in FIG. 32B.

Figure 32C:
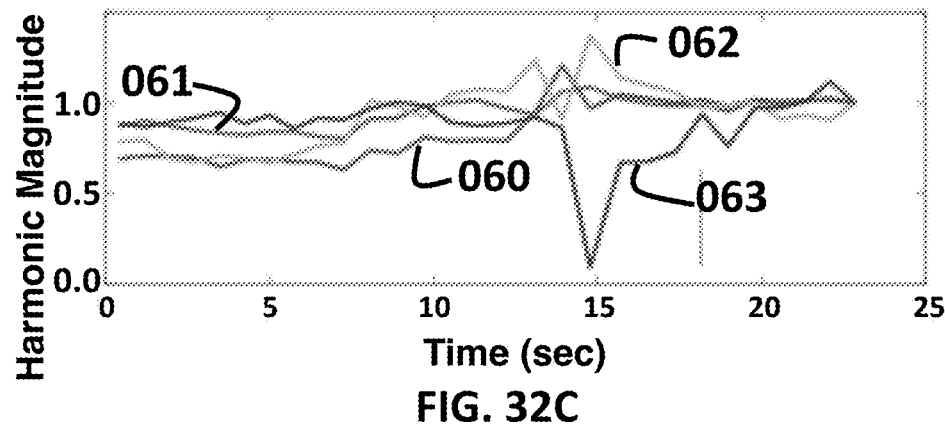
FIG. 32C shows harmonics 0 (060), which is also the FFR, 1 (061), 2 (062) and 4 (063), which exhibit little change as the catheter tip crosses the stenosis.

FIG. 32C shows harmonics 0 (060), which is also the FFR, 1 (061), 2 (062) and 4 (063), which exhibit little change as the catheter tip crosses the stenosis.

In both cases harmonic 3 was orders of magnitude larger than the other harmonics, and changes in harmonic 3 correlated with the location and severity of the stenosis. Changes in harmonic 3 represent changes in the pressure waveform due to interaction with vessel wall, which has increased stiffness at the stenosis. The PTF provides a comprehensive assessment of the stenosis in a vessel because the zero harmonic is equivalent to the FFR and higher harmonics reflect the impact of flowing blood and its interaction with vessel wall.

REFERENCES

1. Nichols, W. and M. O'Rourke, *McDonald's Blood Flow in Arteries*. 5th ed. 2005, London: Hodder Arnold.
2. O'Rourke, M. F., *Vascular impedance in studies of arterial and cardiac function*. Physiological Reviews, 1982. 62(2): p. 570-623.
3. Milnor, W., D. Bergel, and J. Bargainer, *Hydraulic power associated with pulmonary blood flow and its relation to heart rate*. Circ Res. , 1966. 19(3): p. 467-80.
4. Milnor, W. R., et al., *Pulmonary Arterial Pulse Wave Velocity and Impedance in Man*. Circulation Research, 1969. 25(6): p. 637-649.
5. Yin, F., *Ventricular/Vascular Coupling. Clinical, physiological and engineering aspects*. 1987, New York: Springer-Verlag.
6. Dell'Italia, L. J. and W. P. Santamore, *Can indices of left ventricular function be applied to the right ventricle?* Progress in Cardiovascular Diseases, 1998. 40(4): p. 309-324.
7. Sanz, J., et al., *Evaluation of Pulmonary Artery Stiffness in Pulmonary Hypertension With Cardiac Magnetic Resonance*. J Am Coll Cardiol Img, 2009. 2(3): p. 286-295.
8. Piene, H., *Pulmonary arterial impedance and right ventricular function*. Physiological Reviews, 1986. 66(3): p. 606-652.
9. Hunter, K. S., et al., *Pulmonary vascular input impedance is a combined measure of pulmonary vascular resistance and stiffness and predicts clinical outcomes better than pulmonary vascular resistance alone in pediatric patients with pulmonary hypertension*. Am Heart J, 2008. 155(1): p. 166-74.
10. Caro, C. G. and D. D. Mc, *The relation of pulsatile pressure and flow in the pulmonary vascular bed*. J Physiol, 1961. 157: p. 426-53.
11. Patel, D. J., F. M. Defreitas, and D. L. Fry, *Hydraulic input impedance to aorta and pulmonary artery in dogs*. J Appl Physiol, 1963. 18: p. 134-40.
12. Bergel, D. H. and W. R. Milnor, *Pulmonary Vascular Impedance in the Dog*. Circ Res, 1965. 16: p. 401-15.
13. van den Bos, G. C., N. Westerhof, and O. S. Randall, *Pulse wave reflection: can it explain the differences between systemic and pulmonary pressure and flow waves? A study in dogs*. Circ Res, 1982. 51(4): p. 479-85.
14. Maggiorini, M., et al., *Effects of pulmonary embolism on pulmonary vascular impedance in dogs and minipigs*. J Appl Physiol (1985), 1998. 84(3): p. 815-21.

15. Santana, D. B., et al., *Pulmonary artery smooth muscle activation attenuates arterial dysfunction during acute pulmonary hypertension.* J Appl Physiol (1985), 2005. 98(2): p. 605-13.
16. Greenwald, S. E., R. J. Johnson, and S. G. Haworth, *Pulmonary vascular input impedance in the newborn and infant pig.* Cardiovasc Res, 1985. 19(1): p. 44-50.
17. Leather, H. A., et al., *Effects of vasopressin on right ventricular function in an experimental model of acute pulmonary hypertension.* Crit Care Med, 2002. 30(11): p. 2548-52.
18. Wilcox, B. R. and C. L. Lucas, *Pulmonary input impedance in children with left-right shunt.* J Surg Res, 1980. 29(1): p. 40-9.
19. Murgo, J. P. and N. Westerhof, *Input impedance of the pulmonary arterial system in normal man. Effects of respiration and comparison to systemic impedance.* Circ Res, 1984. 54(6): p. 666-73.
20. Kussmaul, W. G., J. M. Wieland, and W. K. Laskey, *Pressure-flow relations in the pulmonary artery during myocardial ischaemia: implications for right ventricular function in coronary disease.* Cardiovasc Res, 1988. 22(9): p. 627-38.
21. Chen, Y. T., et al., *Aortic and pulmonary input impedance in patients with cor pulmonale.* Jpn Heart J, 1990. 31(5): p. 619-29.
22. Kussmaul, W. G., 3rd, et al., *Effects of pacing tachycardia and balloon valvuloplasty on pulmonary artery impedance and hydraulic power in mitral stenosis.* Circulation, 1992. 86(6): p. 1770-9.
23. Huez, S., et al., *Feasibility of routine pulmonary arterial impedance measurements in pulmonary hypertension.* Chest, 2004. 125(6): p. 2121-8.

The invention claimed is:

1. A method for non-invasively evaluating physiological properties of a blood vessel at a section thereof between a first point and along a direction of blood flow a second point in a subject, the method comprising:
   acquiring, non-invasively by a measuring device without injecting any exogenous agent into the subject, a first measurement and a second measurement respectively at the first point and the second point, wherein the first measurement comprises a first sequence of images, and the second measurement comprises a second sequence of images, wherein the first sequence of images and the second sequence of images are taken at different time points in one cardiac cycle of the subject, and each of the first sequence of images and the second sequence of images contains at least one of blood velocity information or blood flow information;
   generating, by a processing device, a first waveform and a second waveform from the first sequence of images and the second sequence of images, respectively; and
   obtaining, by the processing device, a transfer function configured to produce an output waveform given an input waveform, using the first waveform and the second waveform as the input waveform and the output waveform respectively, wherein the transfer function considers a pulsatile nature of the blood flow along the direction thereof and is implemented in a time domain as an autoregressive moving average (ARMA) model:

$$Y_k = X_k + \sum_{i=1}^{p} b_i Y_{k-i} + \sum_{i=1}^{q} a_i X_{k-i};$$

where k is a sample index, $X_k$ are samples of the first measurement, $Y_k$ are samples of the second measurement, p is a number of moving average terms, q is a number of autoregressive terms, and $a_i$ and $b_i$ are coefficients; and
   determining the physiological properties of the section of the blood vessel based on the transfer function and parameters p, q, ai, and bi.

2. The method according to claim 1, wherein each of the first waveform and the second waveform is blood velocity waveform or blood flow waveform.

3. The method according to claim 1, wherein the subject is a human or an animal.

4. The method according to claim 1, wherein the measuring device comprises a magnetic resonance imaging (MRI) scanner or a Doppler ultrasound device.

5. The method according to claim 4, wherein the measuring device comprises an MRI scanner, and the MRI scanner is phase contrast based or cine-based.

6. The method according to claim 1, wherein the blood vessel is an artery or a vein.

7. The method according to claim 6, wherein the blood vessel is a pulmonary artery, and the section of the blood vessel is between a main pulmonary artery (MPA) and a right pulmonary artery (RPA) proximal to a bifurcation; between the MPA and a left pulmonary artery (LPA) proximal to the bifurcation; between the RPA proximal and distal to the bifurcation; or between the LPA proximal and distal to the bifurcation, wherein the method further comprises:
   determining, based on the physiological properties of the section of the blood vessel, whether the subject has a pulmonary hypertension (PH) or a chronic obstructive pulmonary disease (COPD).

8. The method according to claim 6, wherein the blood vessel is a pulmonary artery, and the section of pulmonary artery is between a right pulmonary artery (RPA) proximal and distal to a bifurcation, wherein the method further comprises:
   determining, based on the physiological properties of the section of the blood vessel, whether the subject has an abnormal pulmonary artery (PA) impedance.

9. The method according to claim 1, wherein the first sequence of images in the first measurement and the second sequence of images in the second measurement are acquired in synchronization to the subject's electrocardiogram signal and at equally spaced time points in the one cardiac cycle.

10. The method according to claim 9, wherein the one cardiac cycle comprises a total of at least 20 time points.

11. The method according to claim 10, wherein the one cardiac cycle comprises a total of 20-32 time points.

12. A system for non-invasively evaluating physiological properties of a section of a blood vessel in a subject, comprising a measuring device and a processing device, wherein:
   the measuring device is configured, non-invasively and without injecting any exogenous agent into the subject, to acquire a first measurement at a first point and a second measurement at a second point, wherein the first point and the second point are along a blood flow direction within the section of the blood vessel, the first measurement comprises a first sequence of images, and the second measurement comprises a second sequence of images, wherein the first sequence of images and the second sequence of images are taken at different time points in one cardiac cycle of the subject, and each of the first sequence of images and the second sequence of images contains at least one of blood velocity information or blood flow information; and the processing device is configured to generate a first waveform and a second waveform from the first sequence of images and the second sequence of images respectively, and then to calculate a transfer function configured to produce an output waveform given an input waveform, with the first waveform and the second waveform as the input waveform and the output waveform respectively, wherein:

the transfer function considers a pulsatile nature of the blood flow along the direction thereof, is in a time domain, and is calculated based on an autoregressive moving average (ARMA) model:

$$Y_k = X_k + \sum_{i=1}^{p} b_i Y_{k-i} + \sum_{i=1}^{q} a_i X_{k-i};$$

where k is a sample index, $X_k$ are samples of the first measurement, $Y_k$ are samples of the second measurement, p is a number of moving average terms, q is a number of autoregressive terms, and $a_i$ and $b_i$ are coefficients;

and the processing device is further configured to determine the physiological properties of the section of the blood vessel based on the transfer function and parameters p, q, ai, and bi.

13. The system of claim 12, wherein each of the first sequence of images and the second sequence of images is blood velocity waveform or blood flow waveform.

14. The system of claim 12, wherein the blood vessel is an artery or a vein.

15. The system of claim 12, wherein the subject is a human or an animal.

16. The system of claim 12, wherein the measuring device comprises a magnetic resonance imaging (MRI) scanner or a Doppler ultrasound device.

17. The system of claim 16, wherein the measuring device comprises an MRI scanner, and the MRI scanner is phase contrast based or cine-based.

18. The system of claim 12, wherein the measuring device is configured to acquire the first sequence of images in the first measurement and the second sequence of images in the second measurement in synchronization to the subject's electrocardiogram signal and at equally spaced time points in the one cardiac cycle.

19. The system of claim 18, wherein the one cardiac cycle comprises a total of at least 20 time points.

20. The system of claim 19, wherein the one cardiac cycle comprises a total of 20-32 time points.

* * * * *